(12) United States Patent
Charlton et al.

(10) Patent No.: US 6,640,034 B1
(45) Date of Patent: Oct. 28, 2003

(54) OPTICAL PHOTONIC BAND GAP DEVICES AND METHODS OF FABRICATION THEREOF

(75) Inventors: Martin David Brian Charlton, Southampton (GB); Gregory Jason Parker, Brockenhurst (GB)

(73) Assignee: BTG International Limited, London (GB)

( * ) Notice: Subject to any disclaimer, the term of this patent is extended or adjusted under 35 U.S.C. 154(b) by 213 days.

(21) Appl. No.: 09/910,014

(22) Filed: Jul. 23, 2001

Related U.S. Application Data

(63) Continuation of application No. 09/663,443, filed on Sep. 15, 2000, now abandoned, which is a continuation of application No. 09/415,233, filed on Oct. 12, 1999, now abandoned, which is a continuation of application No. PCT/GB98/01429, filed on May 18, 1998.

(30) Foreign Application Priority Data

May 16, 1997 (GB) .............................. 9710062

(51) Int. Cl.[7] .......................... G02B 6/04; H01L 21/00; H04J 14/02
(52) U.S. Cl. .......................... 385/122; 385/24; 385/15; 385/129; 385/130; 385/37; 385/141; 438/31; 438/32; 359/130
(58) Field of Search .......................... 385/1, 2, 24, 14, 385/129, 130, 131, 132, 32, 43, 122, 37; 437/15, 16, 20, 21, 51; 359/130; 438/31, 32

(56) References Cited

U.S. PATENT DOCUMENTS

| | | | |
|---|---|---|---|
| 4,894,726 A | 1/1990 | Steinhardt et al. ........... 358/298 |
| 5,526,449 A | 6/1996 | Meade et al. .................. 385/14 |
| 5,651,079 A | 7/1997 | Goorjian ....................... 385/16 |
| 5,682,401 A | * 10/1997 | Joannoopoulos et al. ..... 372/96 |
| 5,748,057 A | 5/1998 | De Los Santos ............ 333/134 |
| 5,751,466 A | 5/1998 | Dowling et al. ............. 359/248 |
| 5,802,236 A | 9/1998 | DiGiovanni et al. ......... 385/127 |
| 5,963,683 A | 10/1999 | Goorjian ....................... 385/16 |
| 5,973,823 A | 10/1999 | Koops et al. ................ 359/322 |
| 5,978,530 A | 11/1999 | Russell et al. ................ 385/37 |
| 5,987,208 A | 11/1999 | Gruning et al. ............. 385/146 |

(List continued on next page.)

FOREIGN PATENT DOCUMENTS

| | | | |
|---|---|---|---|
| EP | 0 836 112 A2 | 4/1998 | .................. 385/129 |
| EP | 1 024 378 A2 | 8/2000 | .................. 385/24 |
| EP | 1 168 008 A2 | 1/2002 | .................. 385/24 |
| EP | 1 205 788 A1 | 5/2002 | .................. 385/123 |
| WO | 94/16345 A | 7/1994 | .............. 385/14 X |
| WO | WO 02/14913 A1 | 2/2002 | .................. 385/129 |
| WO | WO 02/25781 A2 | 3/2002 | .................. 385/129 |

OTHER PUBLICATIONS

Kosaka et al, "Photonic Crystals for Micro Lightwave Circuits Using Using Wavelength–Dependent Angular Beam Steering" *Applied Physics Letters*, vol. 74, No. 10, Mar. 1999, pp.1370–1372.

(List continued on next page.)

*Primary Examiner*—Brian Healy
(74) *Attorney, Agent, or Firm*—Nixon & Vanderhye P.C.

(57) ABSTRACT

An optical device includes a waveguide bounded by a region containing a photonic band gap the properties of which determined the transfer characteristic of the waveguide. Such a device may serve as a component of, for example a wavelength division multiplexer, a monochromatic laser or a chemical sensor. It may serve as an optical bus for an electronic component such as a microprocessor. These devices are particularly suitable for incorporation in optical and opto-electronic integrated circuits as they permit the fabrication of waveguides having right-angle bends with a radius of the order of 2 $\mu$m.

26 Claims, 47 Drawing Sheets

U.S. PATENT DOCUMENTS

| | | | | |
|---|---|---|---|---|
| 6,028,693 | A | 2/2000 | Fork et al. | 359/248 |
| 6,134,043 | A | 10/2000 | Johnson et al. | 359/237 |
| 6,134,369 | A | 10/2000 | Kurosawa | 385/132 |
| 6,175,671 | B1 | 1/2001 | Roberts | 385/14 |
| 6,278,105 | B1 | 8/2001 | Mattia | 250/214.1 |
| 6,310,991 | B1 * | 10/2001 | Koops et al. | 385/14 |
| 6,334,017 | B1 * | 12/2001 | West | 385/123 |
| 2002/0021878 | A1 | 2/2002 | Allan et al. | 385/129 |

OTHER PUBLICATIONS

Agio et al, "Impurity Modes in a Two–Dimensional Photonic Crystal: Coupling Efficiency and Q Factor" *J. Opt. Soc. Am*, vol. 17, No. 12, Dec. 2000, pp. 2037–2042.

Kosaka et al, "Superprism Phenomena in Photonic Crystals: Toward Microscale Lightwave Circuits" *Journal of Lightwave Technology*, vol 17, No. 11, Nov. 1999.

Mogilevtsev et al, "Group–Velocity Dispersion in Photonic Crystal Fibers" *Optics Letters*, vol. 23, No. 21, Nov. 1998, pp. 1662–1664.

O'Brien et al, "Lasers Incorporating 2D Photonic Bandgap Mirrors" *Electronics Letters*, vol. 32, No.24, Nov. 1996.

Lee et al, "Microvities, Photonic Bandgaps and Applications to Lasers and Optical Communications" IEEE, 1999.

Kosaka et al, "Superprism Phenomena in Photonic Crystals" *Physical Review B*, vol. 58, No. 16, Oct. 1998.

Hosomi et al, "A Dispersion Compensator Using Coupled Defects in Photonic Crystal" *IEEE Journal of Quantum Electronics*, vol. 38, No. 7, Jul. 2002, pp. 825–829.

Meltz et al, "Bragg Grating Formation and Germanosilicate Fiber Photosensitivity" International Workshop on Photoinduced Self–Organization Effects in Optical Fiber, SPIE vol. 1516, Oct. 1991, pp. 185–199.

Gaponenko et al, "Spotaneous Emission of Dye Molecules, Semiconductor Nanocrystals, and Rare–Earth Ions in Opal–Based Photonic Crystals" *Journal of Lightwave Technology*, vol. 17, No. 11, Nov. 1999, pp. 2128–2137.

Bensity et al, "Radiation Losses of Waveguide–Based Two–Dimensional Photonic Crystals: Positive Role of the Substrate" *Applied Physics Letters*, vol. 76, No. 5, Jan. 2000, pp. 532–534.

Koops et al, "Two–Dimensional Photonic Crystals Produced by Additive Nanolithography with Electron Beam–Induced Deposition Act as Filters in the Infrared" *Microelectric Engineering*, 57–58, 2001, pp. 995–1001.

Krauss et al, "Photonic Crystals in the Optical Regime — Past, Present and Future" *Progress in Quantum Electronics*, vol. 23, 1999, pp. 51–96.

Cao et al, "Microlaser Made of Disordered Media" *Applied Physics Letters*, vol. 76, No. 21, May 2000, pp. 2997–2999.

Jin et al, "Band Gap and Wave Guiding Effect in a Quasiperiodic Photonic Crystal" *Applied Physics Letters*, vol. 75, No. 13, Sep. 1999, pp.1848–1850.

XP–002226009, "466/OFC 2002/Thursday/Morning" 3/2002, pp. 466–468.

* cited by examiner

OPTICAL PHOTONIC BAND GAP DEVICES AND METHODS OF FABRICATION THEREOF

This application is a continuation of application Ser. No. 09/663,443, filed Sep. 15, 2000, now aband., which is a continuation of Ser. No. 09/415,233, filed Oct. 12, 1999, now aband., which is a continuation of PCT/GB98/01429, filed May 18, 1998, the entire content of which is hereby incorporated by reference in this application.

BACKGROUND OF THE INVENTION

This invention relates to method of controlling the propagation characteristics of radiation in waveguides by means of photonic band gaps, to optical devices and, in particular, to optical devices which influence the transmission of radiation by means of photonic band gaps. Such devices may be formed by etching a substance which supports propagation of radiation at a wavelength of interest. Although the embodiments described herein are concerned with visible radiation, the principles involved are equally applicable to techniques for controlling the propagation of other forms of electromagnetic radiation such as ultra-violet, infra-red, terahertz and microwave radiation. In this specification, the term "optical" includes such other forms of radiation.

For some periodic dielectric structures, the propagation of electromagnetic radiation can become forbidden in certain lattice directions. These structures are known as photonic band gap structures. Structures based upon a cubic or triangular lattice of deep air rods in a background dielectric material can exhibit a photonic band gap (PBG). The size and position of the band gap is dependent upon the wave polarisation state, direction of wave propagation, dimensions of the photonic crystal, and the dielectric contrast. The frequency extent of the band gap is of the order of the lattice spacing. Semiconductor materials are ideal for the fabrication of PBGs because of their large dielectric constant. It has also been shown that two-dimensional photonic lattices can have a three dimensional band gap, that is to say, the band gap remains open even when there is a large out of plane wave component.

Photonic band structures with band gaps at optical frequencies have several interesting applications. An important property of photonic band gaps is the ability to enhance or inhibit spontaneous emission within the band gap energy range. This has important implications for direct band gap optoelectronic devices such as semiconductor lasers and light-emitting diodes (LEDs).

Photonic band gap structures can also be fabricated in fluorescent (including laser) materials. The PBG can make these active materials useful as sensors, or to make one transition (or group of transitions) more likely to occur than others.

As a sensor, the PBG may be fabricated to fluoresce at a specified wavelength when the air holes in the structure are filled with air. If however the air holes fill with a different gas, such as pure carbon dioxide, or carbon monoxide, the different refractive index of the gas (compared to ordinary air) could be made to tune the PBG off the fluorescent line which would be easily detected. The PBG structure may be used in a similar way for liquid sensing.

Some laser glasses emit at several different wavelengths (example neodymium-doped GLS glass). Frequently, it is desirable to choose preferentially to amplify just one line. This line may be the weakest transition of the group of lines. A PBG structure in the glass may be employed to prevent the fluorescence of the unwanted lines and promote the transmission of the required wavelength.

A particularly important application would be to make a high energy laser transition in a glass favourable by preventing direct transitions from lower lying radiative levels. In a typical laser system, the lower lying transitions are stronger and more likely to occur. However, there may be useful higher energy levels (for example in the blue region of the spectrum) that could be used, but that are unusable because the lower energy transitions are taking all the energy. A suitably engineered PBG in such a laser system could prevent the lower energy transitions from occurring, thus allowing lasing at the higher energy level.

PCT patent application No. WO 94/16345 (Massachusetts Institute of Technology) discloses low-loss optical and optoelectronic integrated circuits with light guides fabricated in a structure having a photonic band gap. This publication does not disclose methods for the determination of the transmission characteristics of such waveguides, other than the centre frequency of the band gap. Furthermore, it describes embodiments which would not operate in the manner described therein, due to adverse interaction between a photonic band gap and a dielectric waveguide. Another disclosed embodiment would not produce the promised advantage due to the influence of back reflection in a tapered dielectric waveguide.

An etched silicon structure is disclosed by V. Lehmann in *J. Electrochem. Soc.* Vol. 140, No. 10, page 2836, October 1993. However, use of the etched silicon structure as an optical device is not discussed. The etched silicon structure disclosed is formed by etching an homogeneous slab of bulk silicon by placing it in an acid bath. Etching is achieved by establishing an electric field across two opposite, substantially planar, faces of the silicon slab, and illuminating the rear surface. The resultant structure has an array of substantially equally spaced holes or pores formed therein. These holes or pores are referred to as macro pores and occur as a result of an electro chemical reaction in conjunction with the phenomenon of a self adjusting charge distribution at a tip of a macro pore.

Krauss T.F. et al., in Nature 1996 Oct. 24, 1996) Vol. 383 at pages 699–702, describe a photonic bandgap (PBG) device. The device is a two-dimensional lattice in the form of an homogeneous array of holes formed in a semiconductor waveguide of high refractive index silicon. Krauss notes that radiation from a tunable source, incident on the structure at certain angles, is detected as it emerges from a waveguide positioned on a substantially opposite side to where the radiation is incident.

SUMMARY OF THE INVENTION

According to the present invention there is provided an optical device including a waveguide formed in a first region of a first optically-transmissive material bounded by a second region or regions having an array of sub-regions arranged therein to create a photonic bandgap at least partially non-transmissive to radiation of a predetermined frequency or frequencies wherein the frequency transmission characteristics of said waveguide are at least partially determined by the transmission characteristics of said second region or regions.

There is also provided an optical transfer device having a first plurality of input ports and a second plurality of output ports coupled by a waveguide at least partially bounded by a photonic band gap wherein at least one of said first plurality of ports is adapted to pass an optical signal having a first range of frequencies and at least one of said second plurality of ports is adapted to pas an optical signal having a second range of frequencies, said first and second range of frequencies being defined by said photonic band gap.

There is also provided an active optical device having a waveguide comprising a region of optically-transmissive material bounded by a photonic band gap and containing a dopant adapted to induce quasi-stable energy levels in said material.

The invention further provides a hybrid optoelectronic signal translation device having a first region adapted to transfer a signal by means of movement of electrical charge carriers and a second region adapted to transfer a corresponding signal by means of electromagnetic radiation and electro-optic transducer means disposed between said first and second regions to convert said signal from or to said corresponding signal wherein said second region includes a third region at least partially bounded by a photonic band gap.

The invention further provides a coupler to a waveguide defined by a photonic band gap having an input or output port for the transfer of radiation to or from said waveguide wherein said input or output port includes a region having a graded refractive index to enhance the transfer of radiation to or from said waveguide.

There is also provided a method of fabricating an optical device comprising the steps of forming a waveguide in a first region of a first optically-transmissive material by creating in a second region or regions an array of sub-regions having a photonic bandgap at least partially non-transmissive to radiation of a predetermined frequency or frequencies wherein the radiation transmission characteristics of said waveguide are at least partially determined by the transmission characteristics of said second region or regions.

According to an aspect of the present invention there is provided an optical device comprising a substrate supporting a waveguide, an input channel and at least two output channels in optical connection with said waveguide, the waveguide being formed from a material of a first refractive index and having an array of regions formed therein, the regions having a different refractive index to that of the waveguide, so that a beam of radiation incident on the device is split into at least two output beams.

Preferably, the intensities of the output beams are substantially equal.

According to a particular aspect of the present invention, the optical device may be used as a WDDM. The WDDM may be used as a wavelength multiplexer.

According to a particular aspect of the present invention, the optical device is adapted to separate a group of information channels from a plurality of input channels encoded by wavelength.

According to another aspect of the present invention there is provided a device comprising an etched semiconductor substrate, characterised in that a plurality of holes or perforations are formed in the substrate the holes or perforations are of a non-uniform nature and/or have a non-uniform inter-hole spacing.

According to another aspect of the invention, there is provided a method of manufacturing an optical device comprising the steps of forming a waveguide on a substrate the waveguide having a first refractive index and forming an array of regions in the waveguide, said regions having a different refractive index to the waveguide.

Preferably the optical device is formed from an etched semiconductor comprising a silicon substrate and at least one overlying layer.

According to another aspect of the invention there is provided a method of multiplexing, or demultiplexing, a plurality of signals comprising combining, or splitting, said signals using an optical device as hereinbefore described.

According to a yet further aspect of the invention there is provided a method of exposing electromagnetic signal(s) to an array of regions having a first dielectric constant disposed within a waveguide formed from a second dielectric constant and varying at least one of said dielectric constants so as to vary a characteristic of said signal(s).

An example of an optical device which may advantageously be made in accordance with one aspect of the present invention is a wavelength division demultiplexer (WDDM). A WDDM splits a single incident beam of radiation, carrying data, into two or more beams of different wavelength. Each of the split beams carries different data from that carried by another beam. Wavelengths are selected such that data transmitted at one wavelength does not interfere with data transmitted at another wavelength. The result is that one data channel, such as an optical fibre, is capable of carrying several different data signals encoded by the wavelength of the carrier signal. Thus, the data carrying capacity of the fibre is increased.

Prior WDDM's suffer from the disadvantage that the minimum bandwidth of a channel can be large. Also these devices are discrete components, are difficult to align, and are not robust. They are also polarisation insensitive.

A wavelength multiplexer is a device which transfers a Wavelength Division Multiplexer (WDM) encoded input signal to a plurality of output channels, whilst simultaneously routing a selected group of wavelength signals to a predetermined group of output channels. A wavelength multiplexer which includes the optical device of the present invention therefore has the added feature of wavelength selectivity.

A splitter separates a single incident beam of radiation carrying data, into two or more beams, of reduced power. Each of the split beams carries identical information. The result is that a single data channel can be distributed to several different destinations simultaneously. An input channel may consist of a plurality of data channels, each encoded according to the wavelength of a carrier signal, or by Time Division Multiplexing (TDM). In such an arrangement all data signals input to the device from the input data channel are routed simultaneously to all of the output channels.

Wavelength Division Multiplexers (WDM) are able selectively and simultaneously to route a given wavelength encoded input data channel to a pre-defined sub-group of output channels. A sub-group of output channels may be different for each wavelength encoded input data channel. In addition, the sub-group of output channels may be further reduced or increased according to the electromagnetic polarisation state of the original input data channel.

The input channel may also be encoded by electromagnetic polarisation state. This doubles the capacity of the input channel. However, prior grating beam splitters or multiplexers suffer from the disadvantage that beams split from a single channel may have widely varying intensities or powers. Another problem suffered by existing splitters and multiplexers is that the maximum number of output channels is also quite small. The present invention overcomes these problems, providing an optical device suitable for use with data carrying channels.

An example of an optical device in accordance with another aspect of the present invention is an optical signal cross-connect. A cross connect allows simultaneous bi-directional communication between a plurality of data channels so that data signals input to the device from any single channel are distributed simultaneously to all other channels. Input channels may carry data signals encoded by carrier wavelength, electromagnetic polarisation state, or by Time Division Multiplexing (TDM). A single device then allows simultaneous bi-directional communication between several sets of transceivers, maintaining high channel separation between them all. Present cross connects may be 'mode dependent' resulting in a significant variation in power between the output channels. In addition wavelength selectivity can be incorporated in to this exchange to route a group of wavelength signals to a group of destinations.

Preferably the array of regions formed in the waveguide is in the form of regular hexagonal pattern with the axes of holes being orthogonal to the surface of the waveguide. In this arrangement a single input beam may be split into a plurality of output beams.

Preferably the input beam is split into six output beams.

The optical device may be used as part of a combiner, in which case a plurality of input beams incident on the device may be combined into a single output beam.

Preferably the depth of the waveguide is substantially constant. The array may be disposed in three-dimensional pattern, throughout the volume of the waveguide.

An optical device which may be made in accordance with yet another aspect of the present invention is an integrated optical polarisation controller. A randomly polarised input beam of arbitrary wavelength is separated into TE and TM polarisation states. The invention may be used with such a device, so that a sub-group of channels may be polarisation multiplexed as well as multiplexed as described above.

If a defect, such as a line defect, is introduced into the device, sharp bends may be created into an optical path in an integrated planar waveguide. At present this is impossible to achieve by other methods.

Yet further optical devices may be used as part of a photonic band pass filter. In such an arrangement, the inclusion of 'defects' within the otherwise periodic lattice improves the performance of the device, creating a narrow passband within the wavelength range of a stopband.

The array may be in the form of another shape such as, for example, a square or it may be 'quasi periodic'. This gives a different number of output beams (e.g. 4 or 2 for a square lattice). By quasi-periodic, in this instance, what is meant is a structure which may be composed of a superposition of two regular lattices which then result in a non uniform lattice. It may also be in the form of a lattice the spacing and/or packing arrangement of which changes along a given dimension in a predetermined manner.

According to another aspect of the present invention there is provided a device comprising an etched semiconductor substrate, characterised in that a plurality of holes or perforations are formed in the substrate the holes or perforations are of a non-uniform nature and/or have a non-uniform inter-hole spacing.

The etching technique has made possible the fabrication of waveguide beam splitters and 90° bends. The bend radius (with zero loss) is ~50 $\mu$m as opposed to the current state of the art ~10 mm using other techniques. The possible limit for 633 nm radiation is ~2 $\mu$m. This makes feasible an optical interconnect in chip-scale integration for computing and communications applications.

The holes or perforations are disposed in an array through a semiconductor substrate so that the inter-hole spacing varies in a predetermined manner.

In accordance with one aspect of the invention, the variation in the inter-hole spacing or diameter of holes is such that a physical characteristic of radiation incident on the optical device is varied. Thus, for example, between first and second adjacent rows, along an edge of the array, the inter-hole or perforation spacing may be 10 $\mu$m; and between a second and a third row of holes in the array, the inter-hole spacing may be 100 $\mu$m.

The spacing between adjacent rows may increase by a regular amount from one pair of adjacent rows to the next. Holes or perforations may be grouped into rows and columns, or may be arranged in a circular, triangular, square, spiral or any other shaped pattern.

This variation in inter-row (or column) spacing of an array may increase linearly or non-linearly. For example an inter-hole or perforation spacing may be defined as 'd' and a relationship between spacing of adjacent rows I may be expressed as $I_{n+1}=I_n+$ kd where k is any positive number. This simple linear relationship is discussed in greater detail below. It will be appreciated that the spacing may increase non-linearly.

For WDDM, most appropriate defects are where the relative diameter of a fraction of the holes is increased or reduced.

The set of defects may be arranged in a regular fashion or perhaps superimposed randomly throughout a regular lattice. The quantity of defective holes may determine the efficiency of the effect.

A medium of variable refractive index may be disposed in the holes or perforations. Means may be provided for varying the refractive index of the medium. Additionally, nonlinearity may be introduced by the presence of dopants, creating quasi-stable energy levels which absorb or emit radiation.

The refractive index of the medium in the holes or perforations may be varied by exposing the medium to an electric or magnetic field which is changed by way of a controller. Such a modified device provides a selectively variable optical switch. Alternatively the medium of variable refractive index may comprise a multi-layered structure formed by etching or crystal growth.

Photonic band gap structures can be fabricated in fluorescent (including laser) materials. The PBG can make these active materials useful as sensors, or to make one transition (or group of transitions) more likely to occur than others.

As a sensor, the PBG may be fabricated to fluoresce at a specified wavelength when the air-holes in the structure are filled with air. If however the air holes fill with a different gas, such as pure carbon dioxide, or carbon monoxide, the different refractive index of the gas (compared to air) could be made to tune the PBG off the fluorescent line which would be easily detected. The PBG structure could be used in a similar way for liquid sensing.

Some laser glasses emit at several different wavelengths (example neodymium doped GLS glass) and we may want to choose to preferentially amplify just one line, and often that line is the weakest transition of the group of lines. A PBG structure in the glass can prevent the fluorescence of the unwanted lines and promote the transmission of the required wavelength.

A particularly important application would be to make a high energy laser transition in a glass favourable by preventing direct transitions from lower lying radiative levels. In a typical laser system, the lower lying transitions are stronger and more likely to occur. However, there may be useful higher energy levels (for example in the blue region of the spectrum) that could be used, but that are unusable because the lower energy transitions are taking all the energy. A properly engineered PBG in such a laser system could prevent the lower energy transitions from occurring, thus allowing lasing at the higher energy level.

Photons lying near the edge of the band gap in energy will be considerably reduced in velocity through the PBG structure (within the band gap itself they stop, they are standing waves). By fabricating a PBG region which is close to the transmitted (information carrying) photon energy, the photon stream can be slowed down—the wave velocity is reduced. This would allow signal processing of the data to occur in more reasonable time scales (in exactly the same way that delay lines are used in signal processing electrical signals).

BRIEF DESCRIPTION OF THE INVENTION

Embodiments of the invention will now be described, by way of example only, and with reference to the accompanying drawings in which.

Figure 9A:
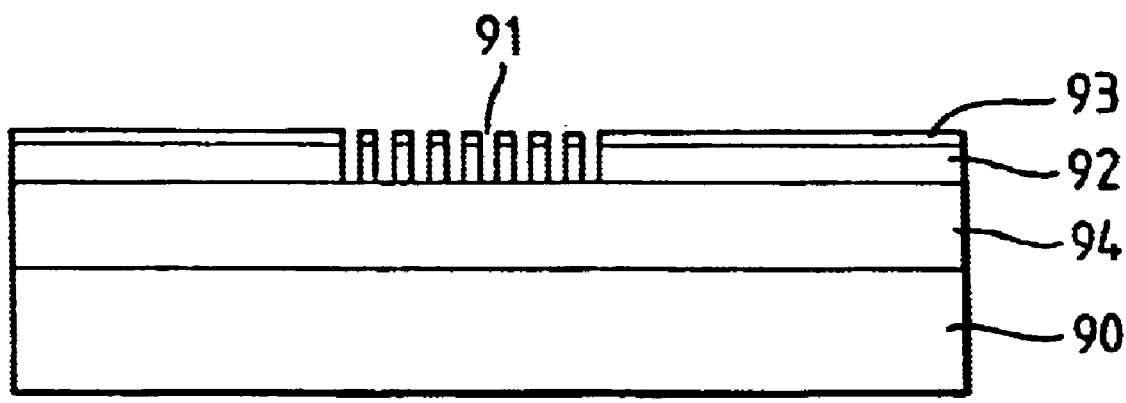
Figure 9B:
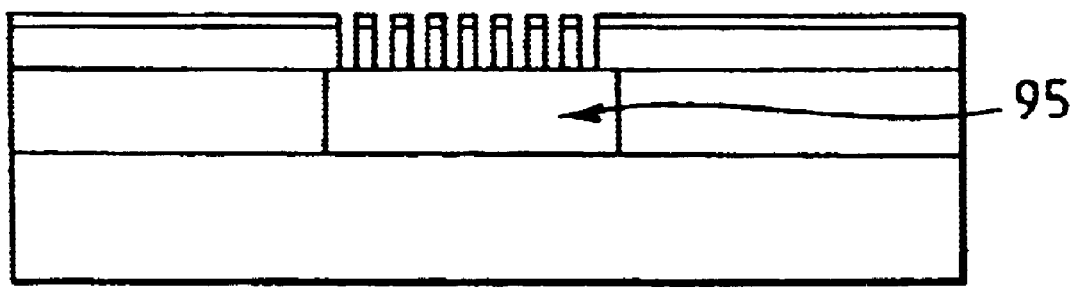
Figure 9C:
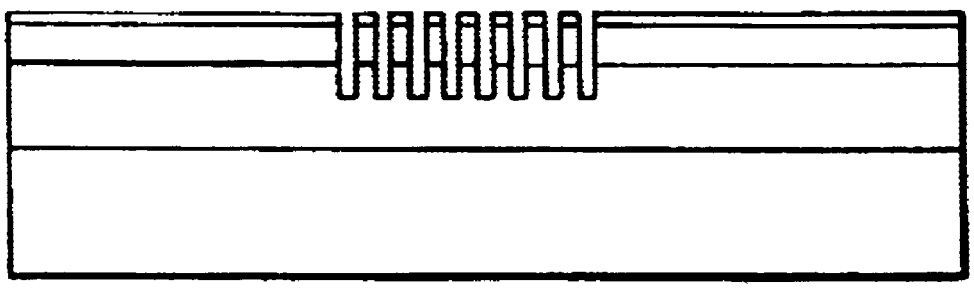
Figure 10:
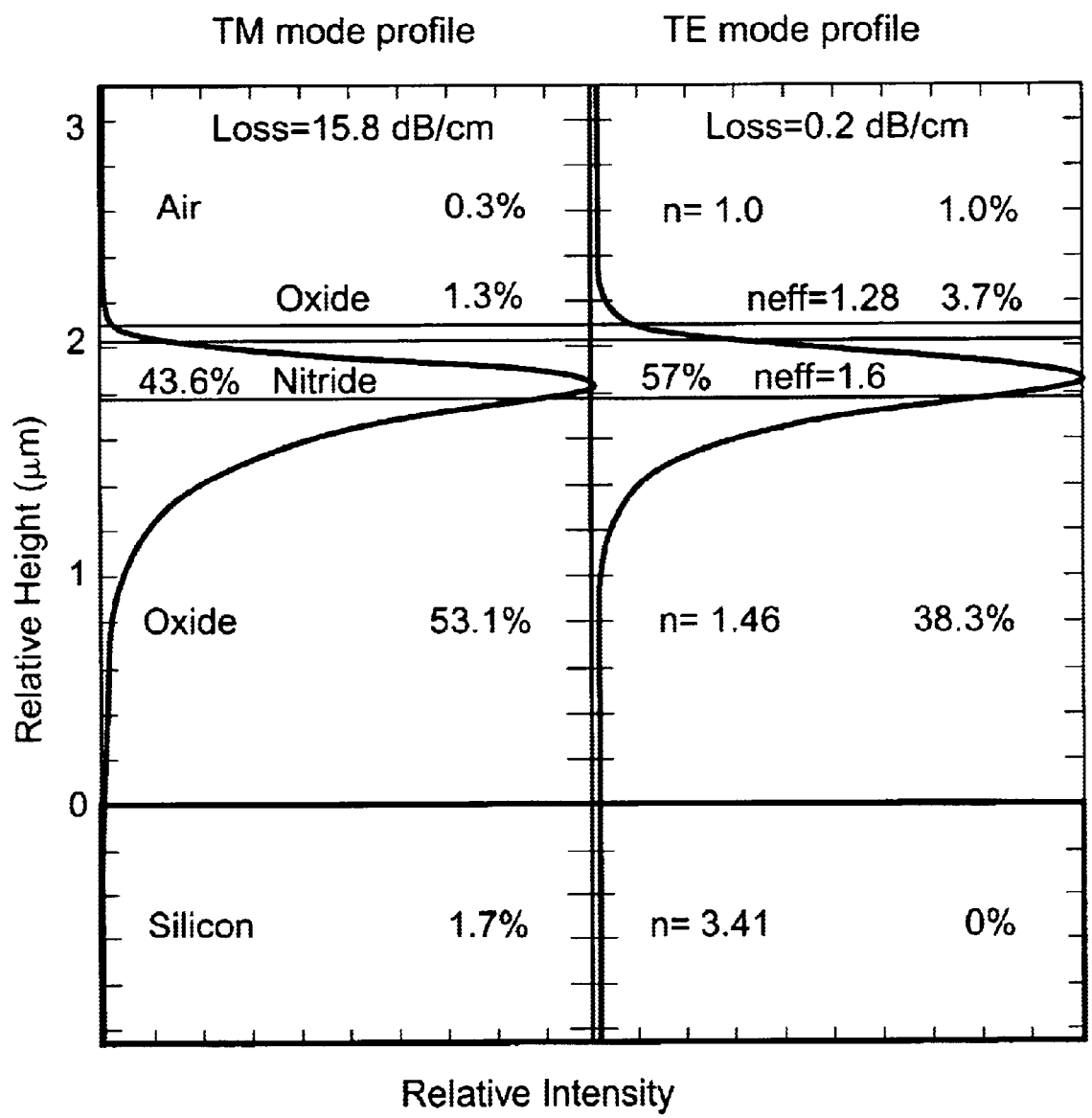
Figure 11:
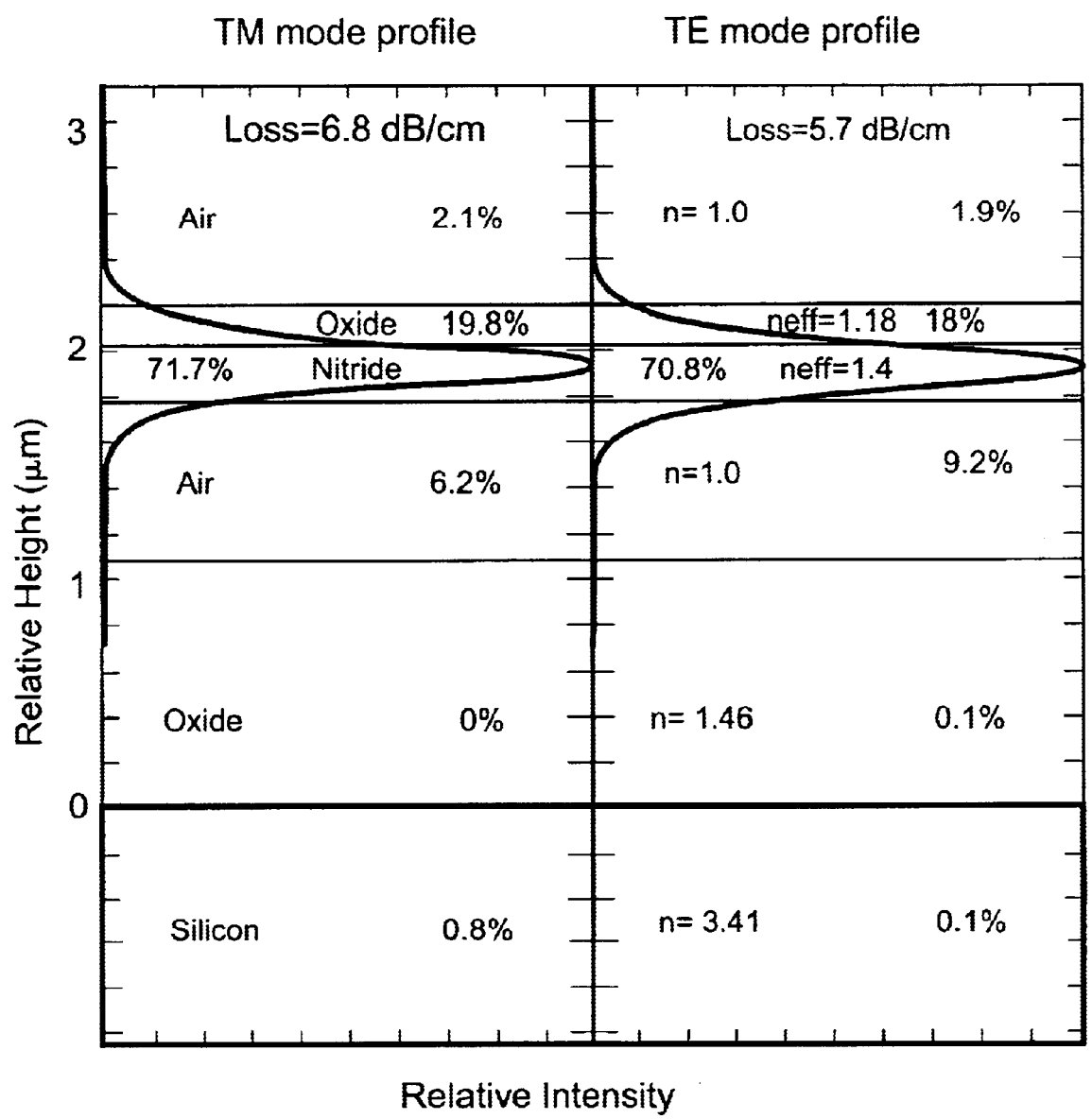
Figure 12:
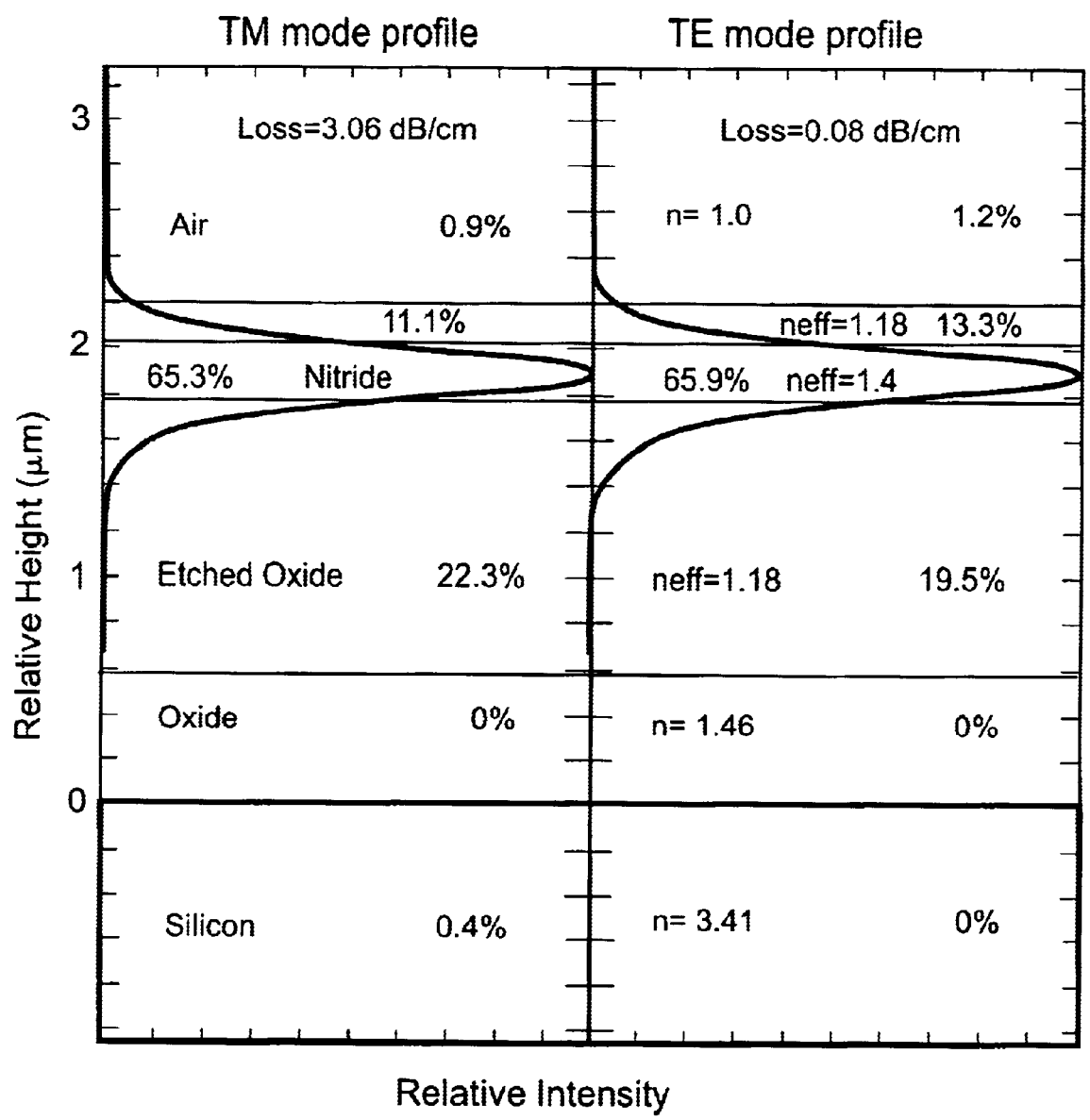
Figure 13:
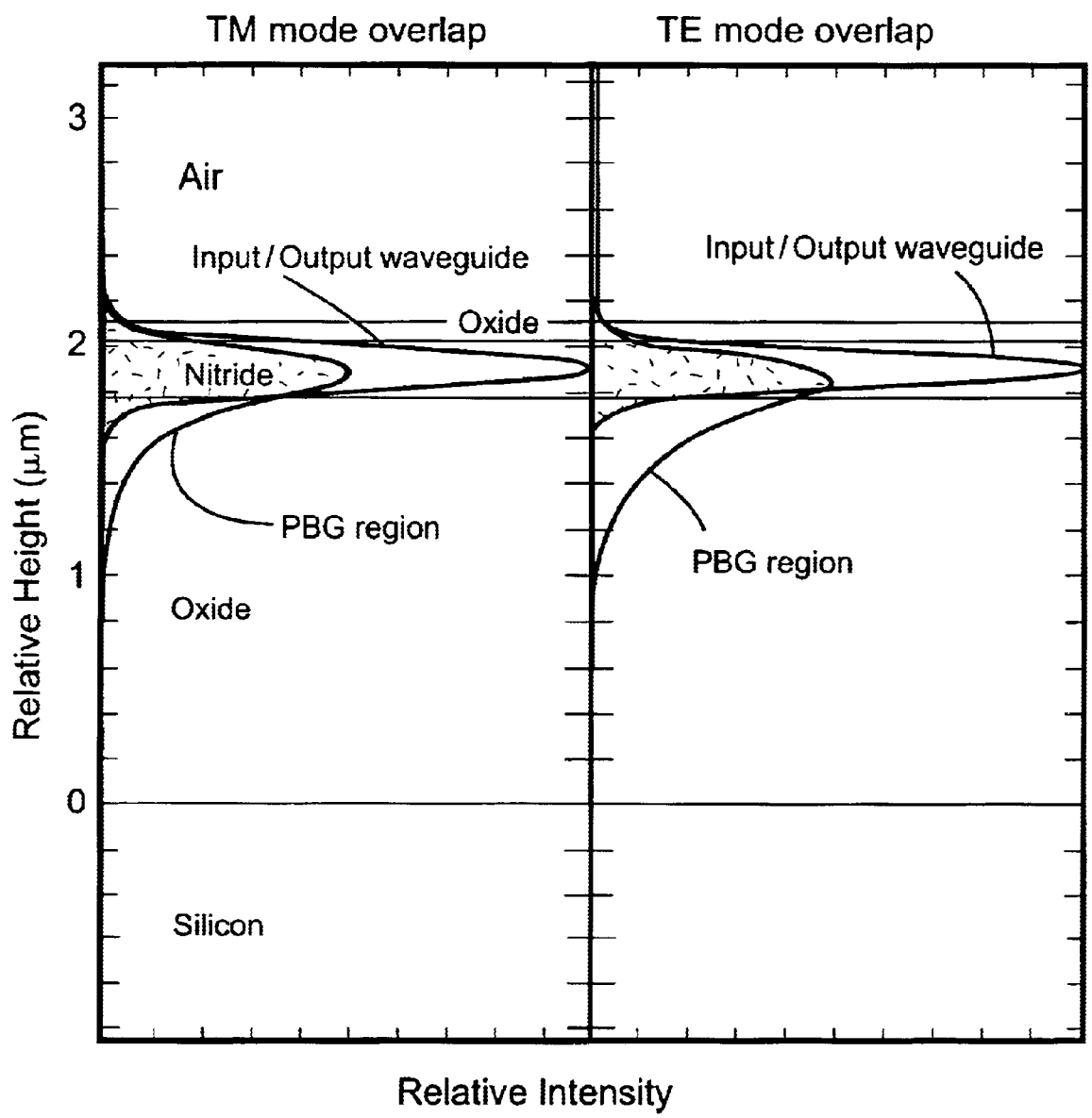

FIG. 9a to c shows the structure of various devices;

FIGS. 10 to 12 illustrate guided mode profiles;

FIG. 13 illustrates mode coupling in waveguides;

FIGS. 14 to 18 are scanning electron micrographs of different structures; and

Figure 1:
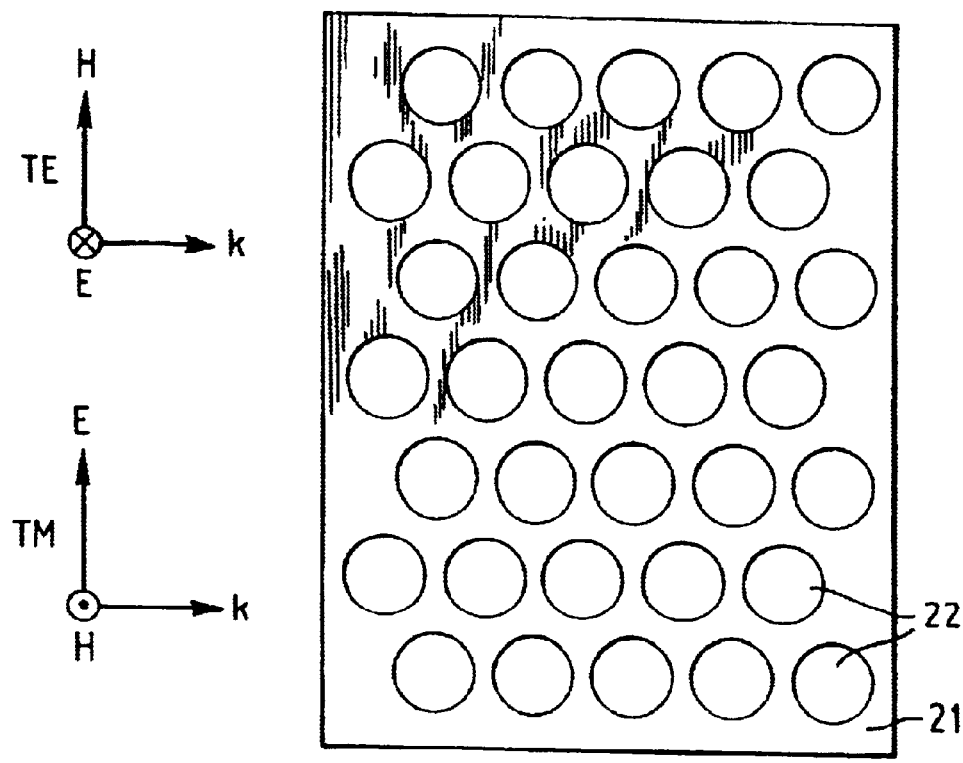
FIGS. 1 and 2 are explanatory diagrams used in wave propagation analysis
Figure 8:
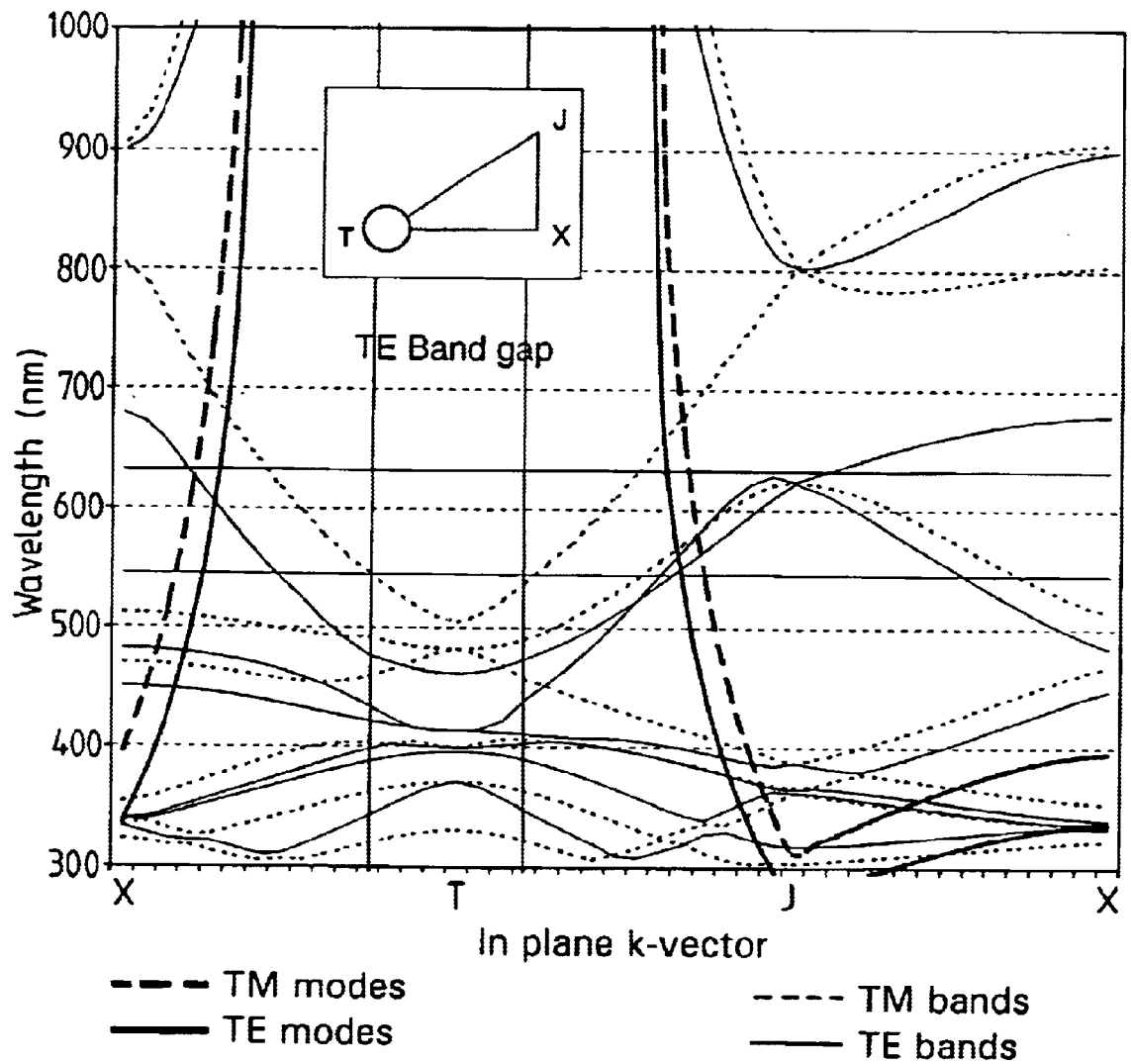
Figure 19A:
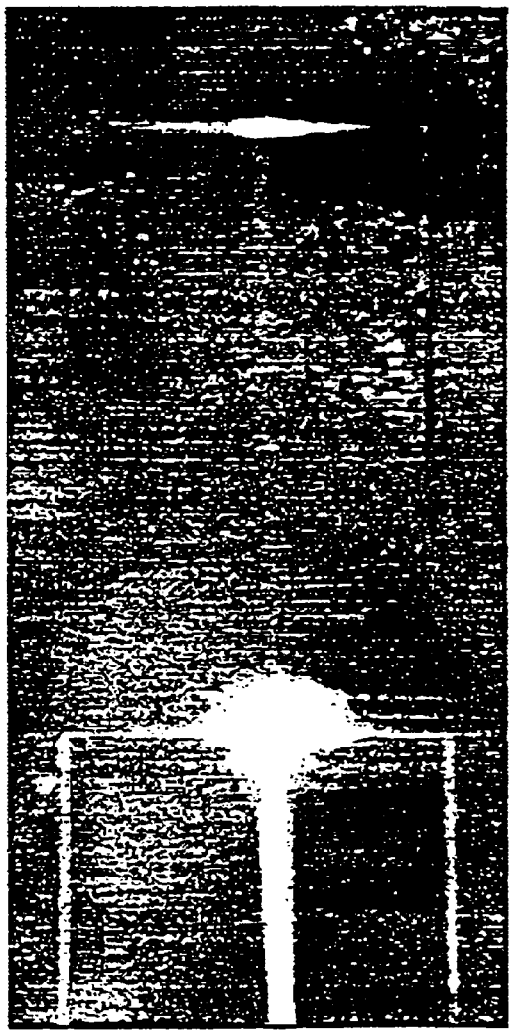
Figure 19B:
Figure 20:
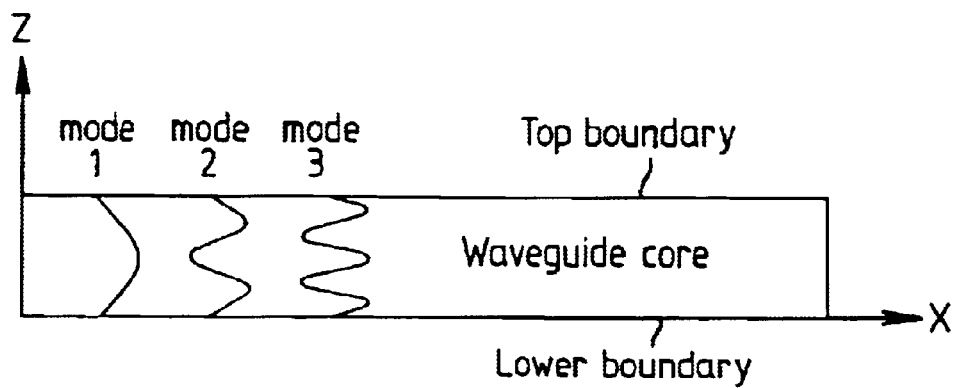
Figure 21:
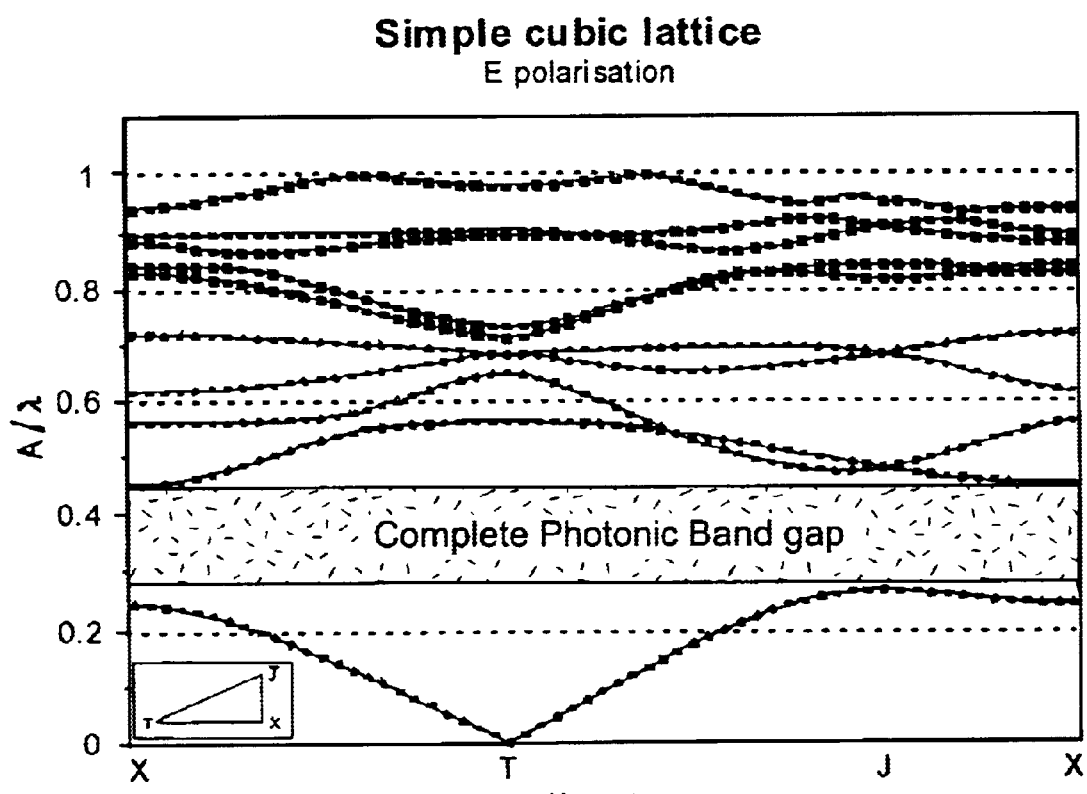
Figure 22:
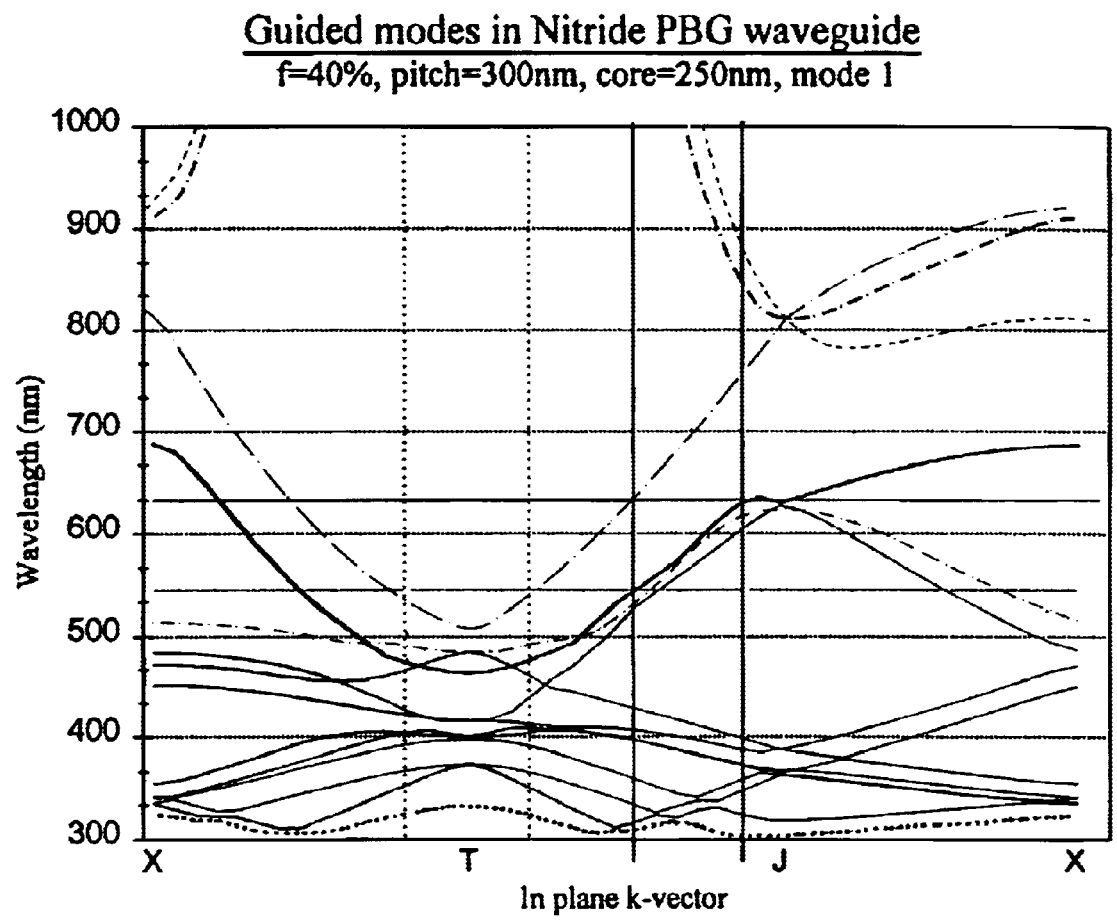
Figure 23A:
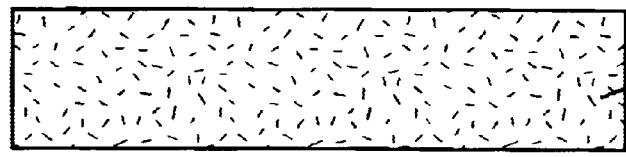
Figure 23B:
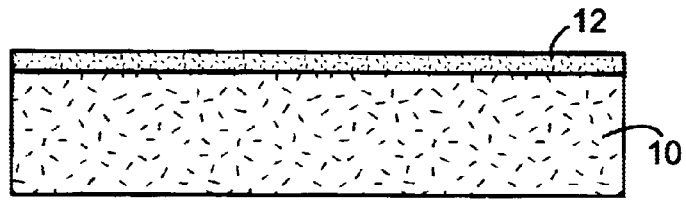
Figure 23C:
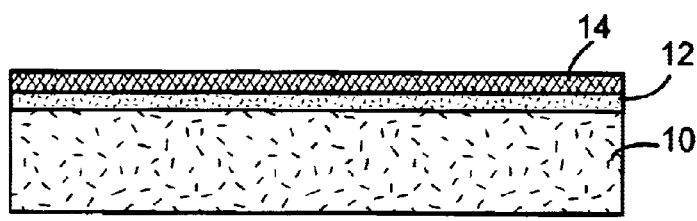
Figure 23D:
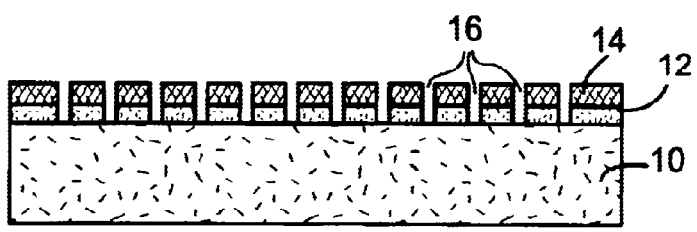
Figure 23E:
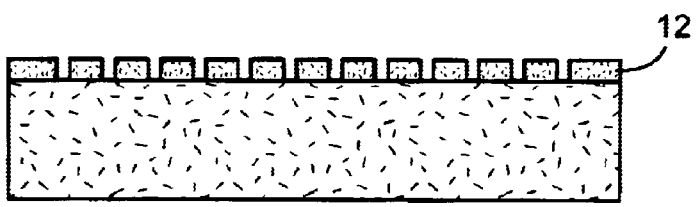
Figure 23F:
Figure 23G:
Figure 23H:
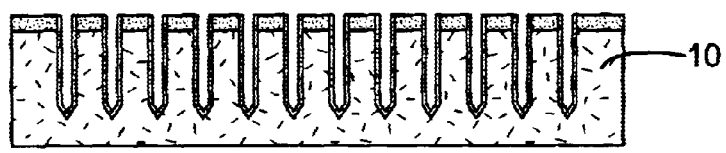
Figure 23I:
Figure 23J:
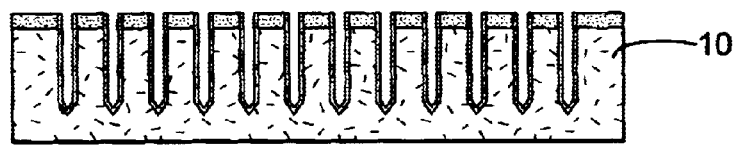
Figure 23K:
Figure 23L:
Figure 23M:
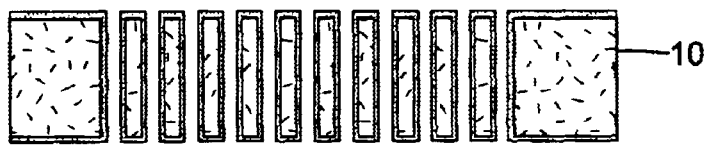
Figure 23N:
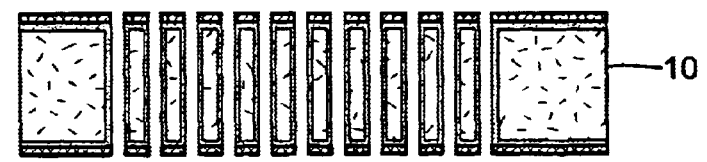
Figure 24:
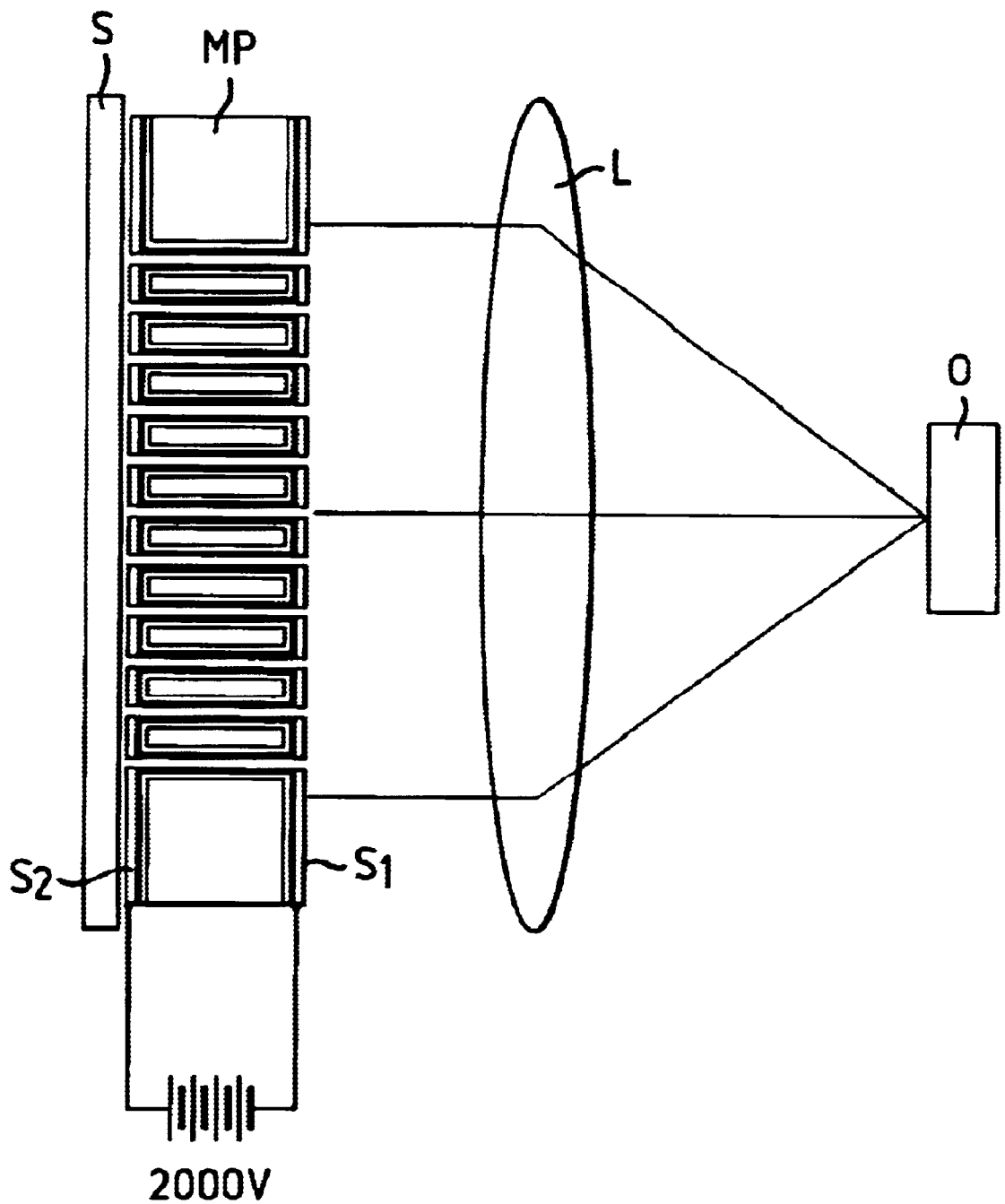
Figure 25:
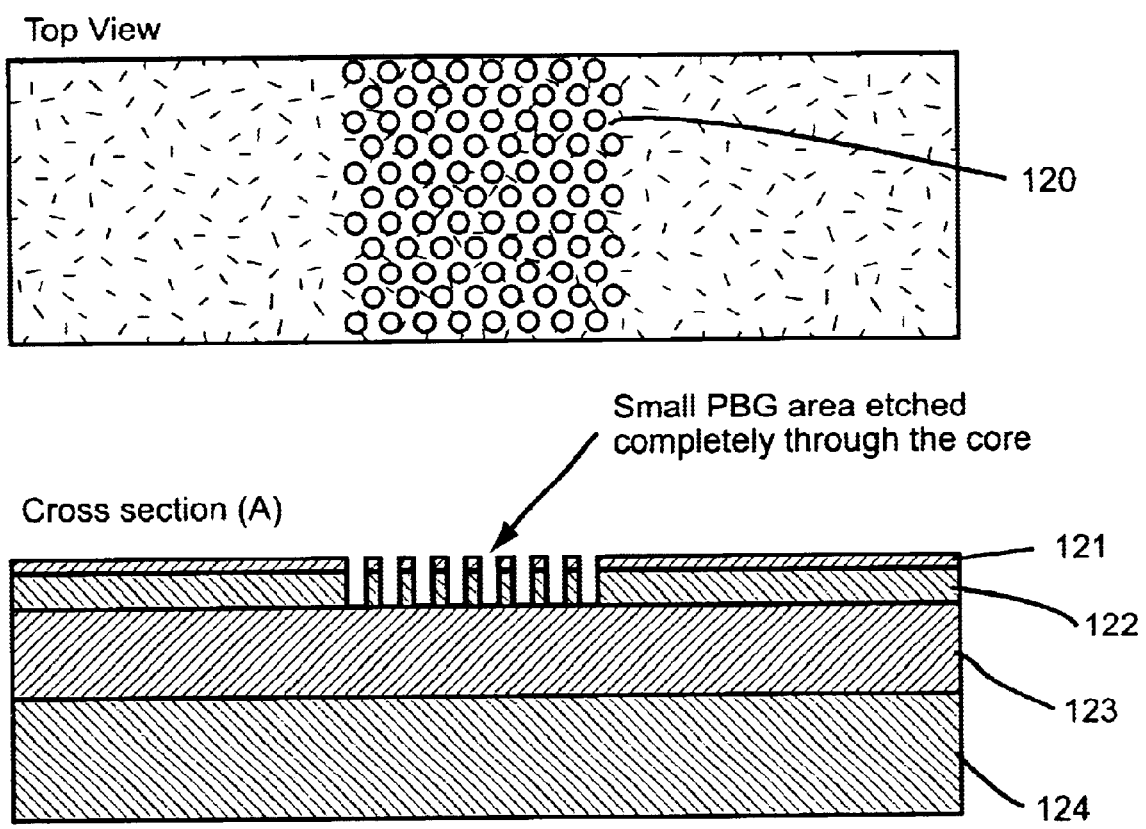
Figure 26:
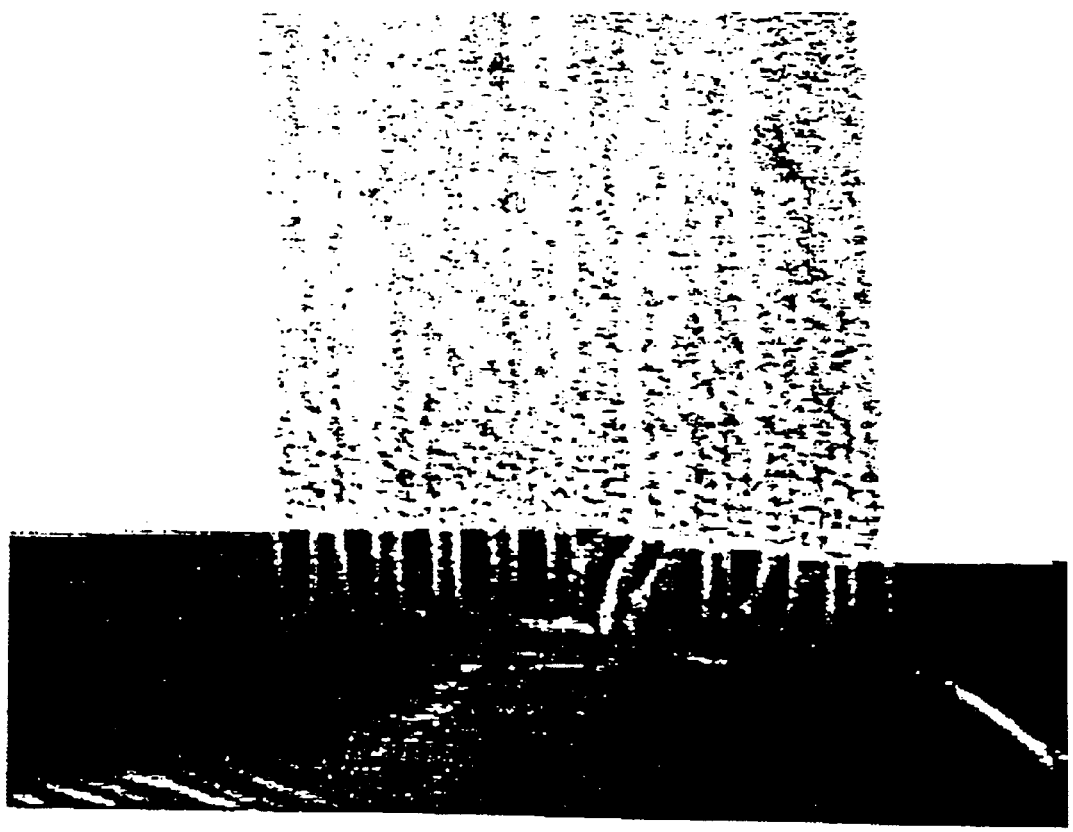
Figure 27:
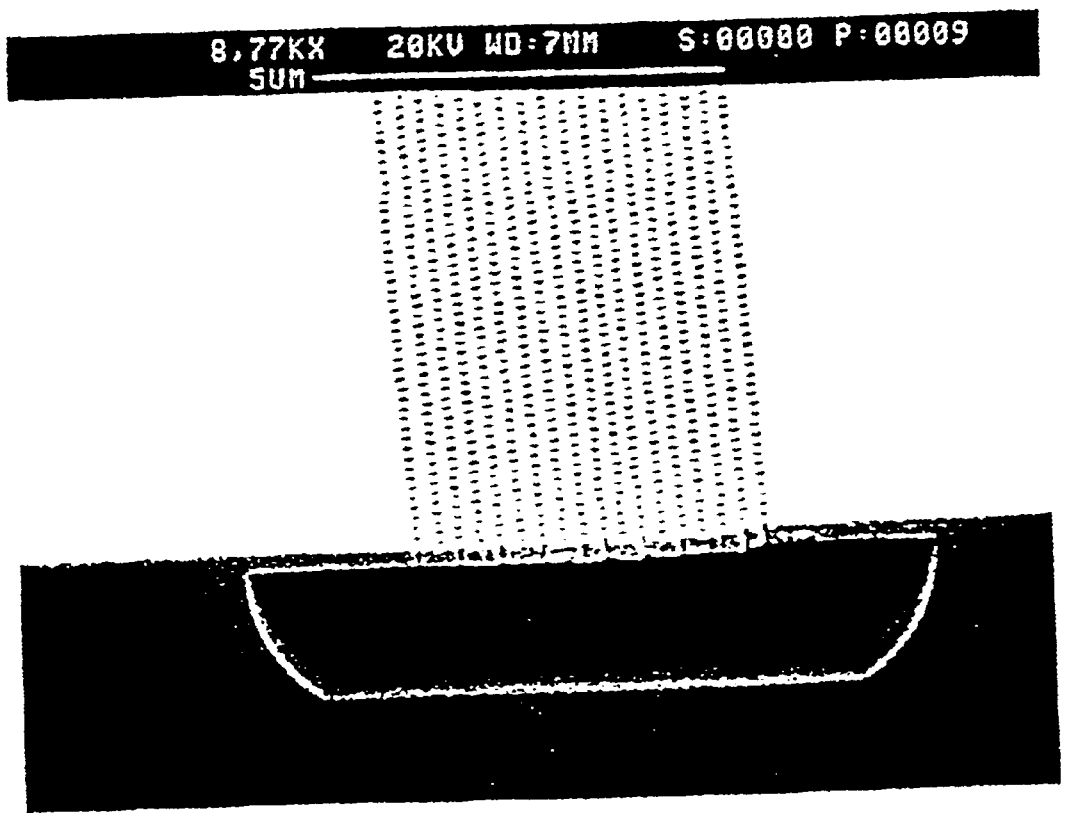
Figure 33:
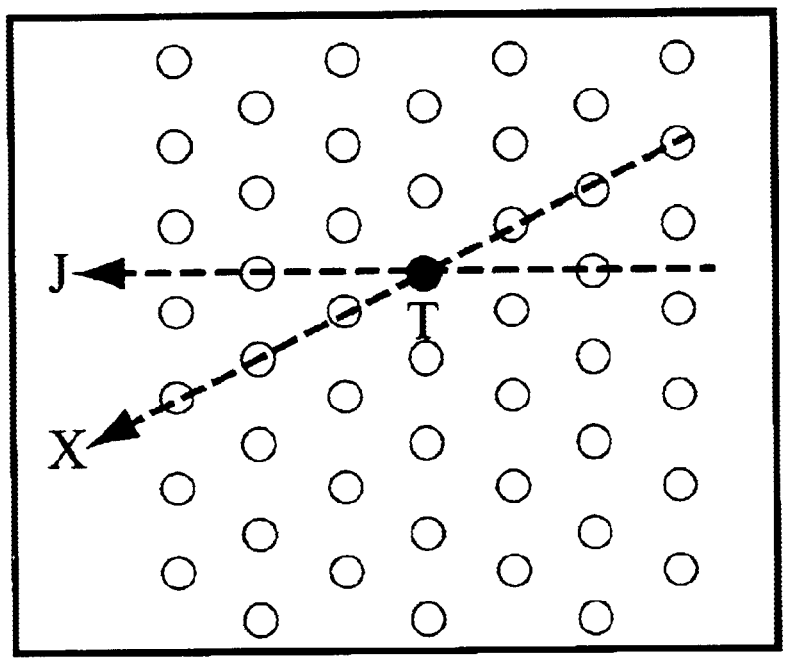
Figure 34:
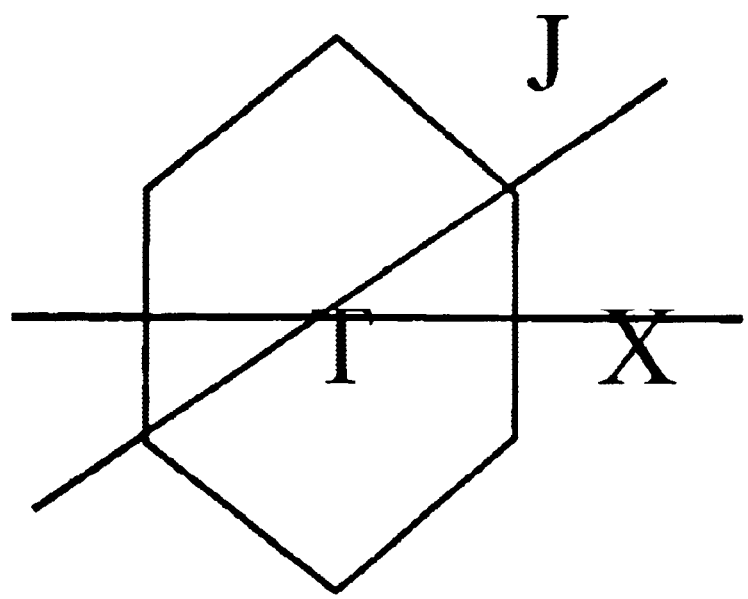
Figure 35:
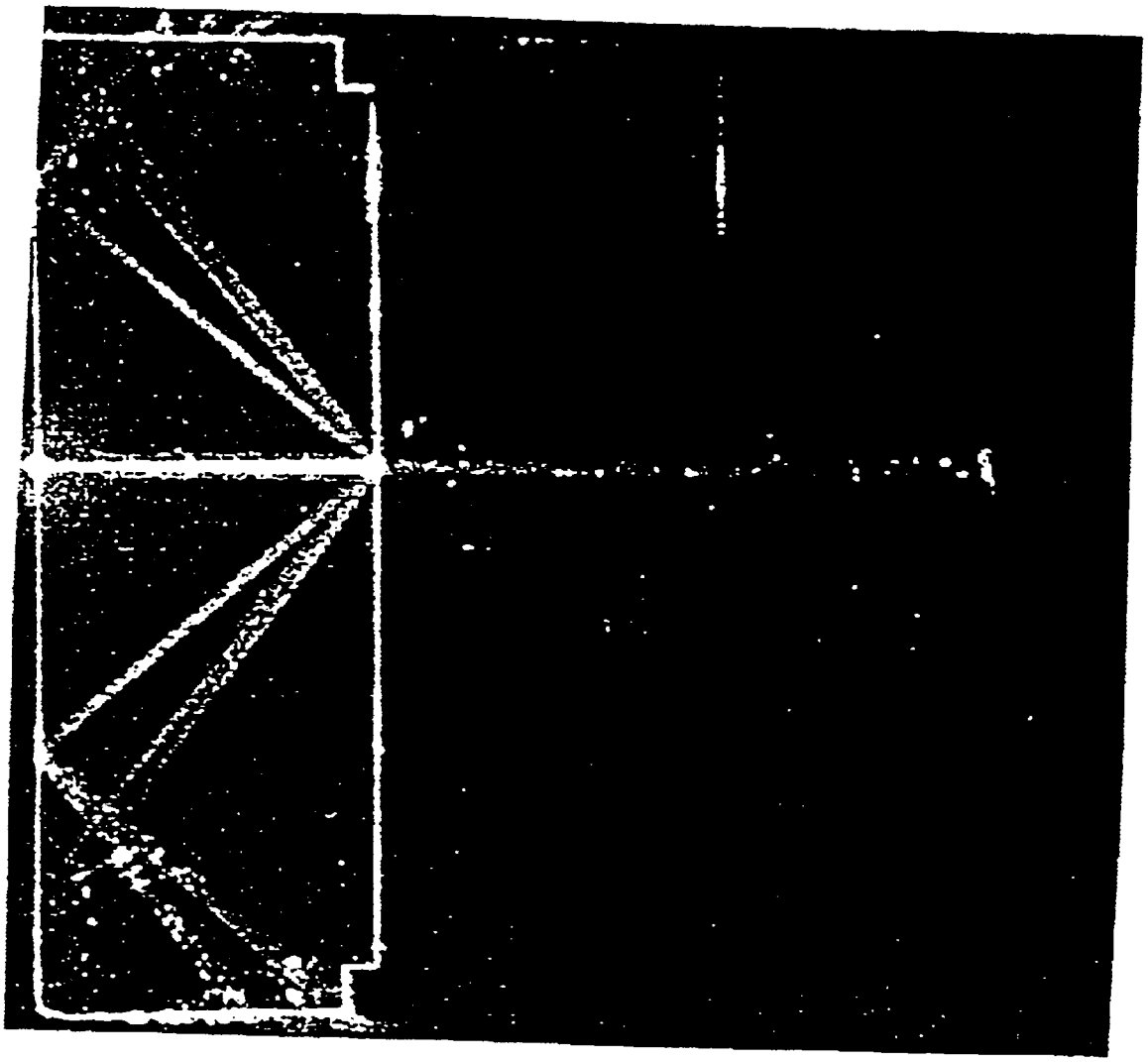
Figure 36A:
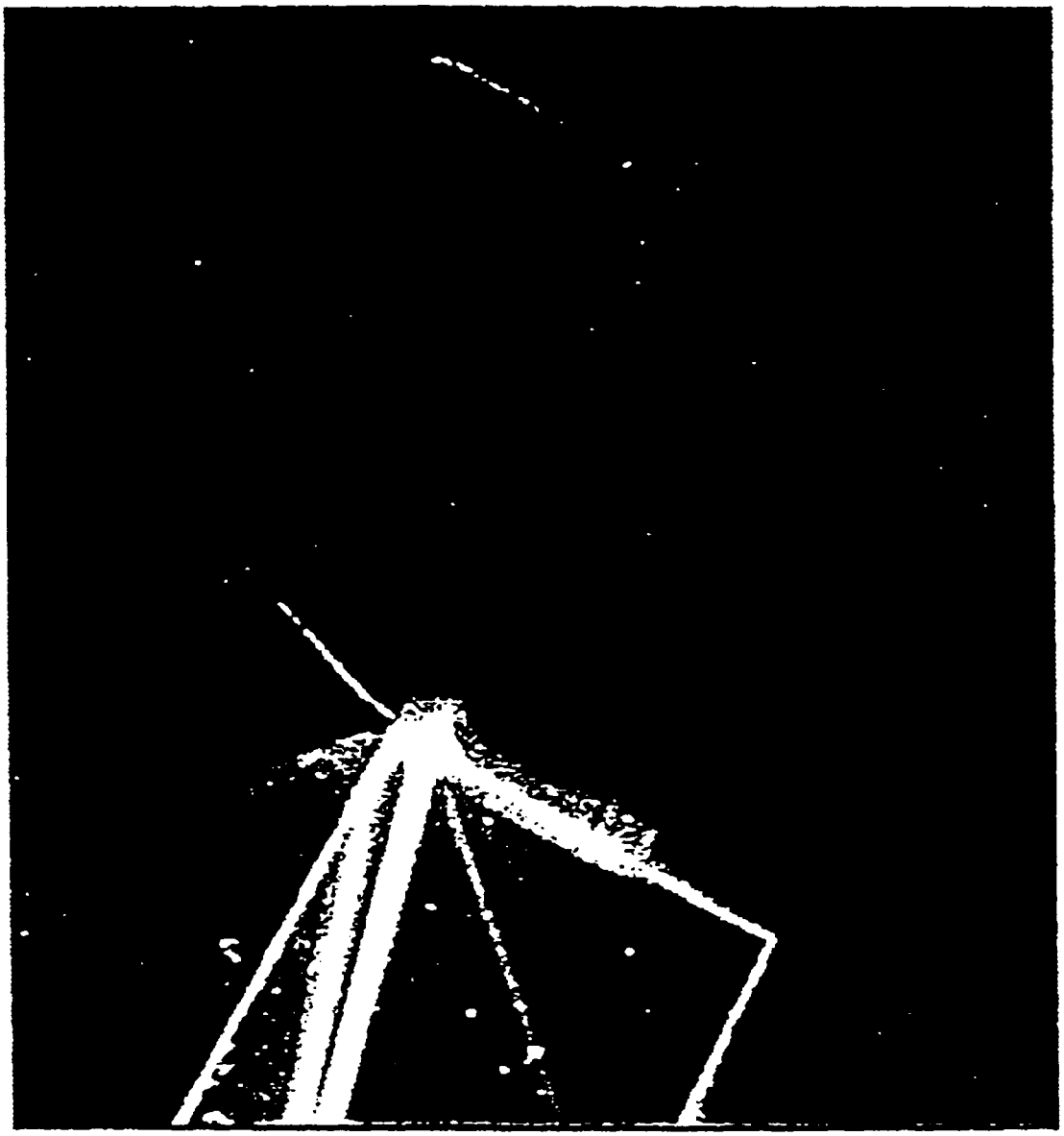
Figure 36B:
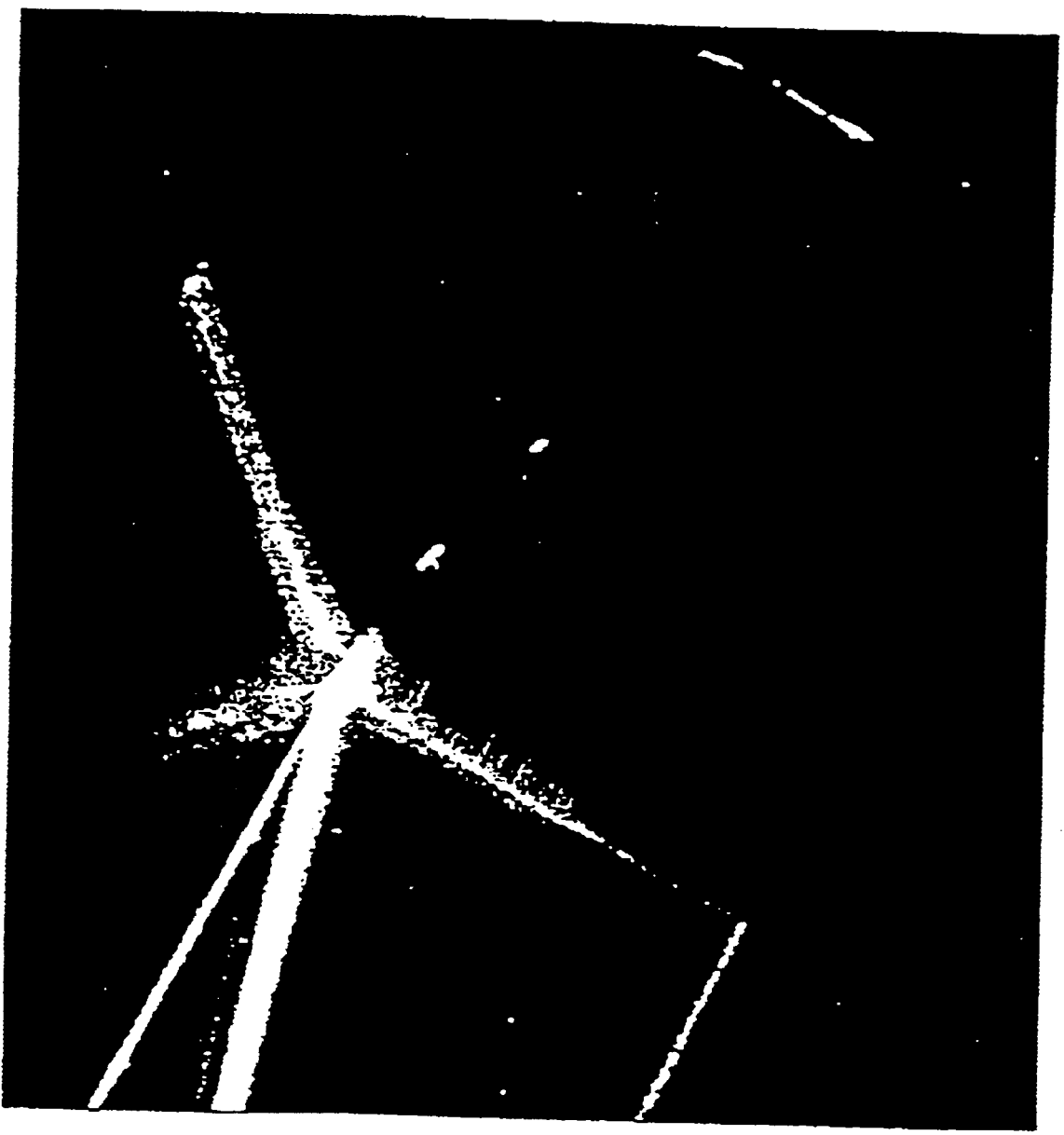
Figure 37A:
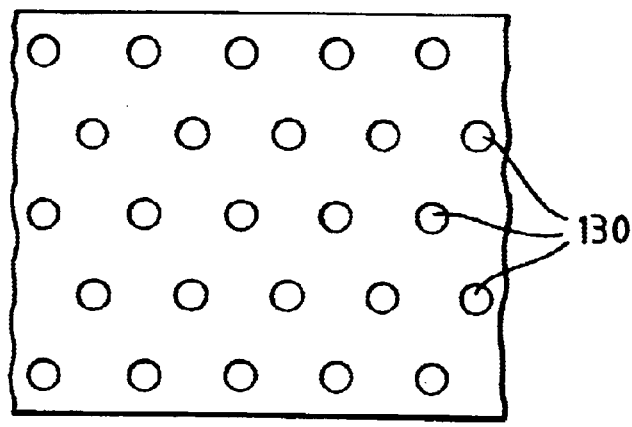
Figure 37B:
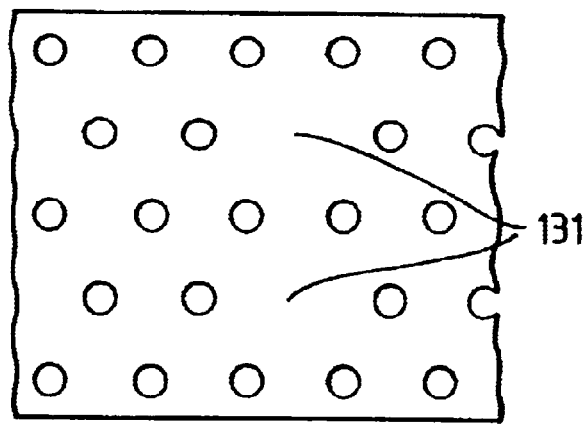
Figure 37C:
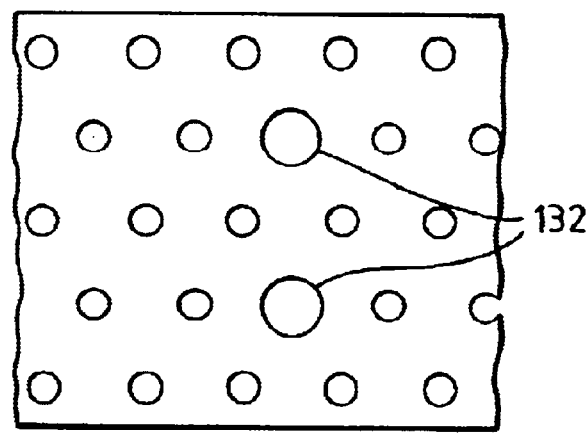
Figure 38:
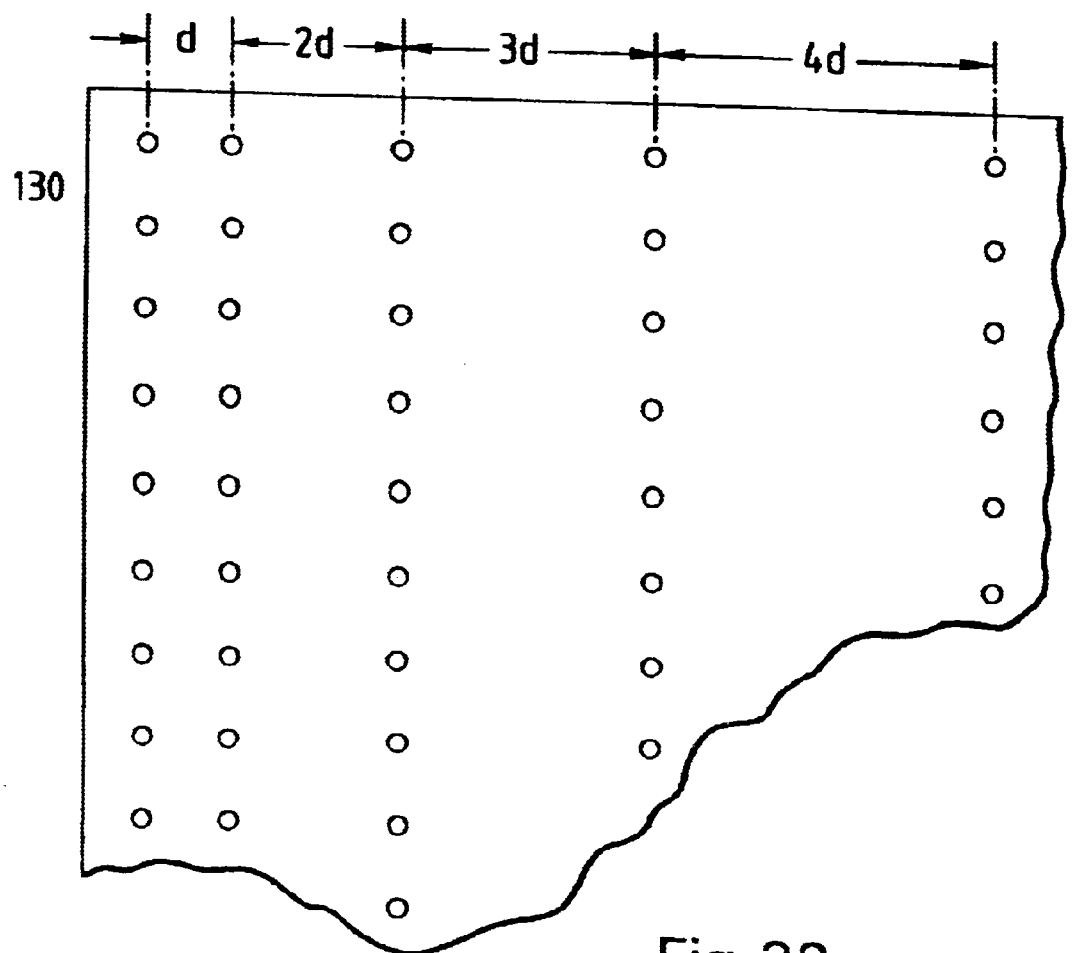
Figure 39:
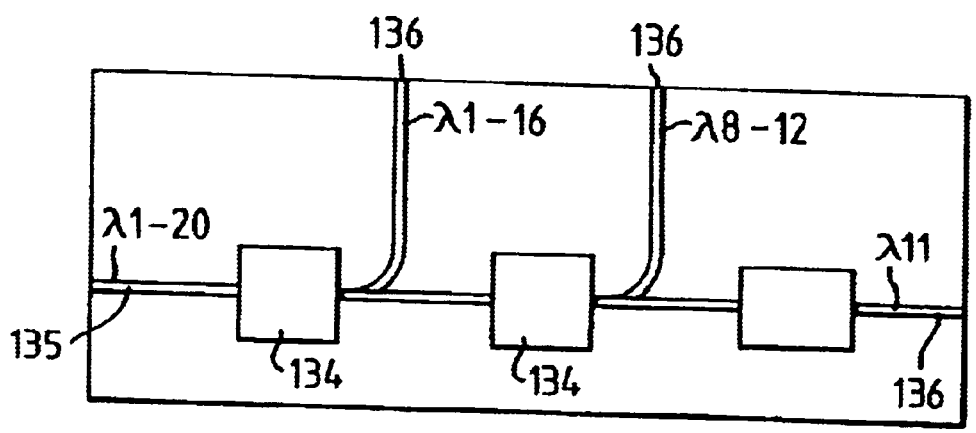
Figure 40A:
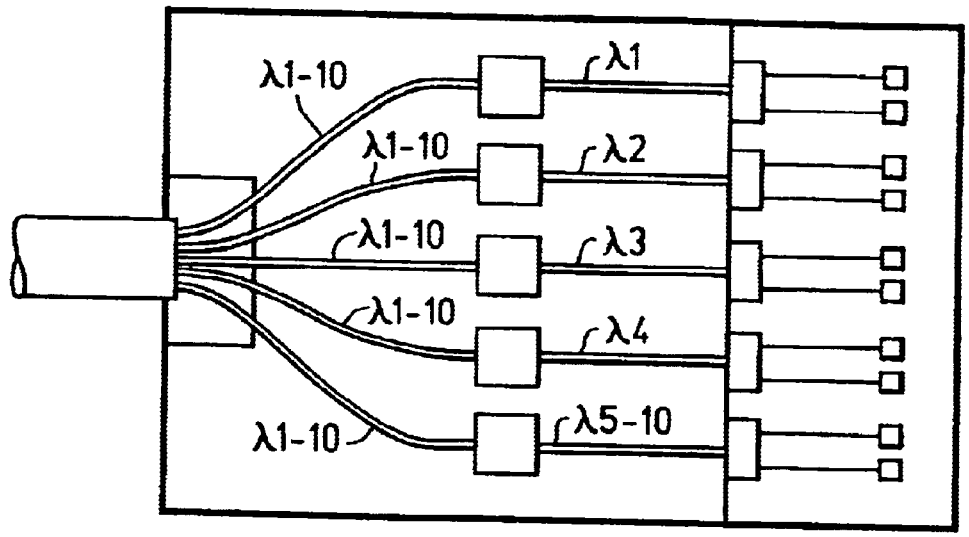
Figure 40B:
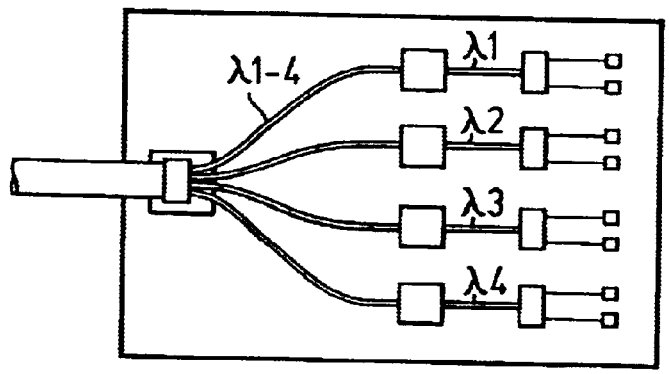
Figure 40C:
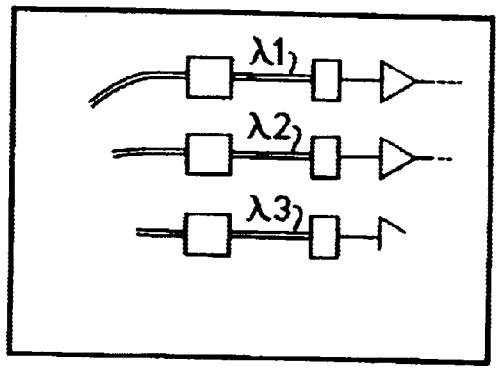
Figure 41A:
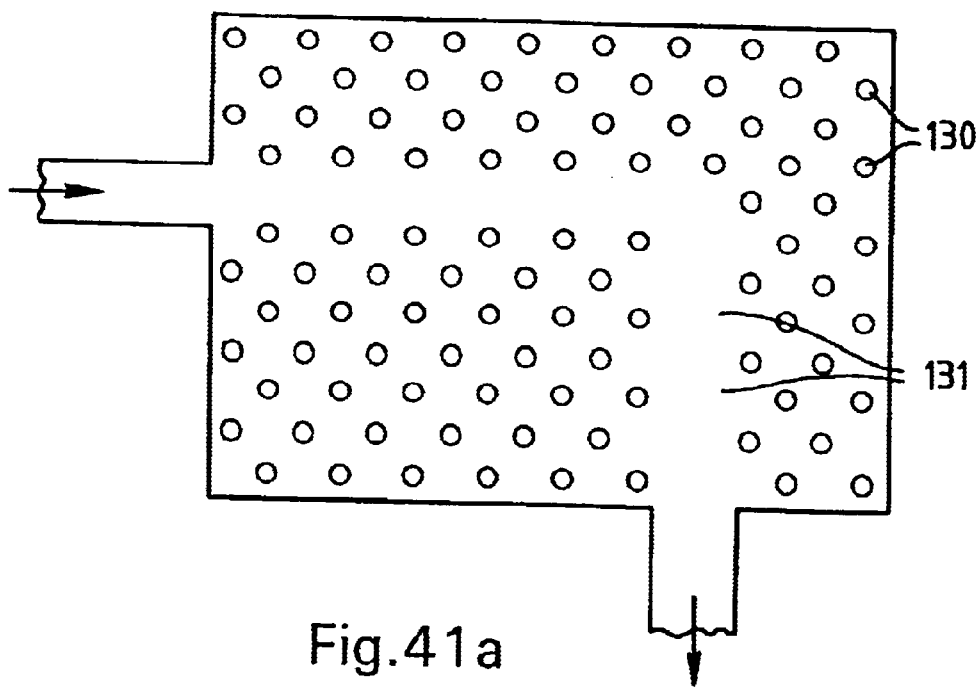
Figure 41B:
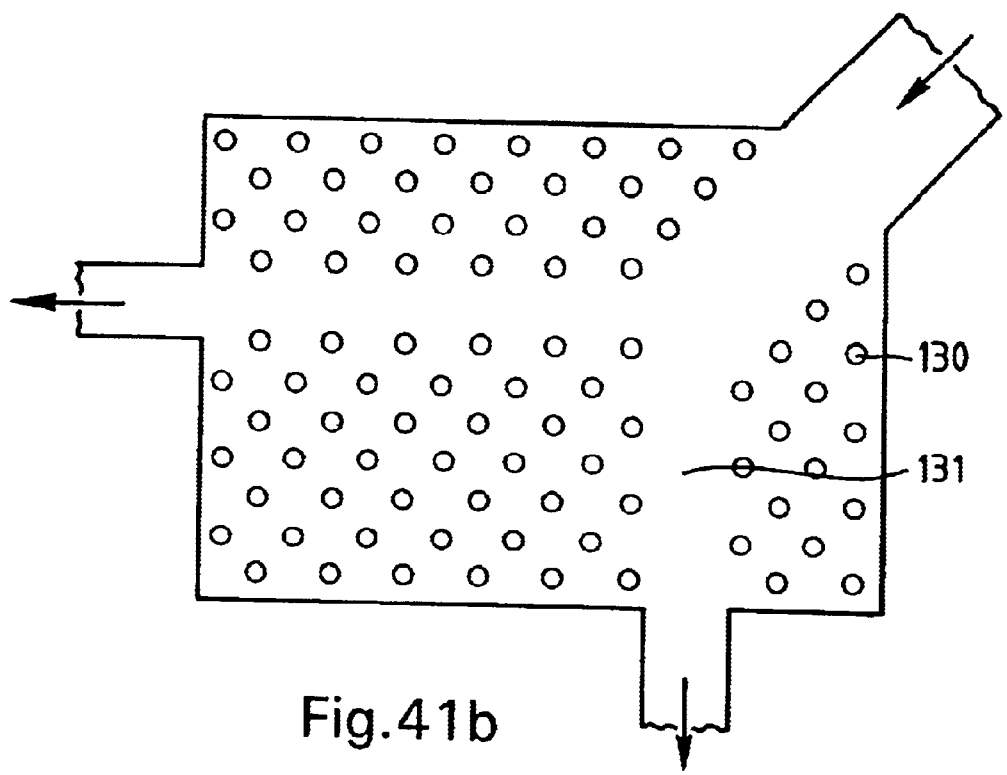
Figure 42A:
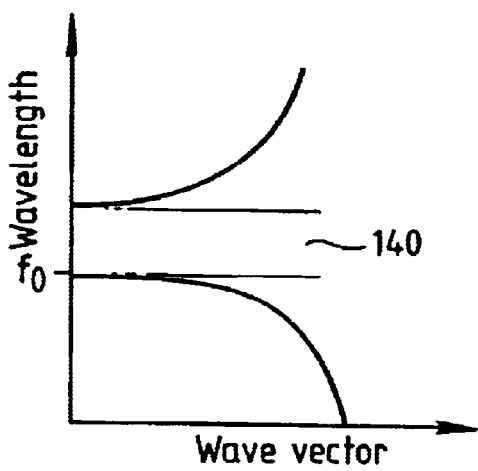
Figure 42B:
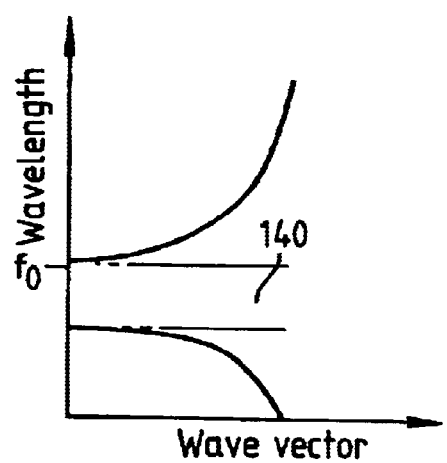
Figure 42C:
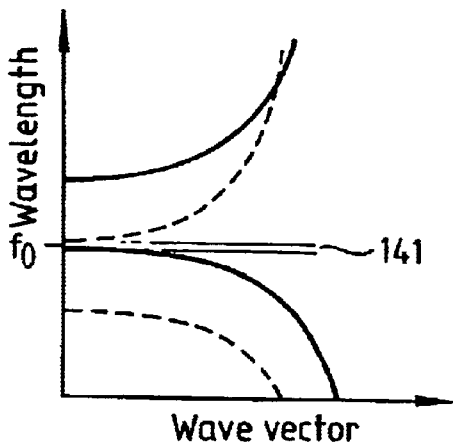
Figure 42D:
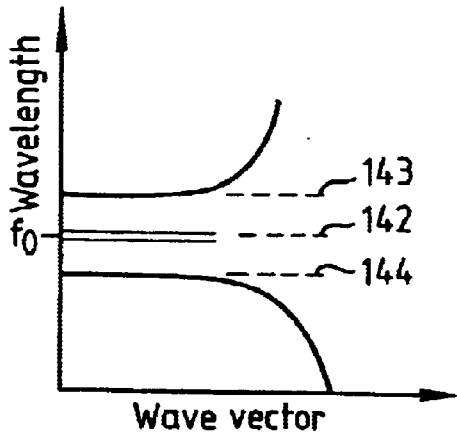
Figure 43:
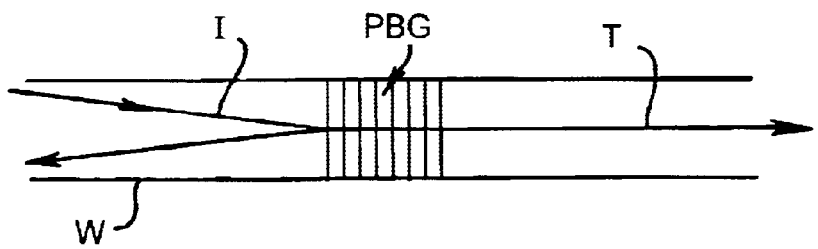
Figure 44A:
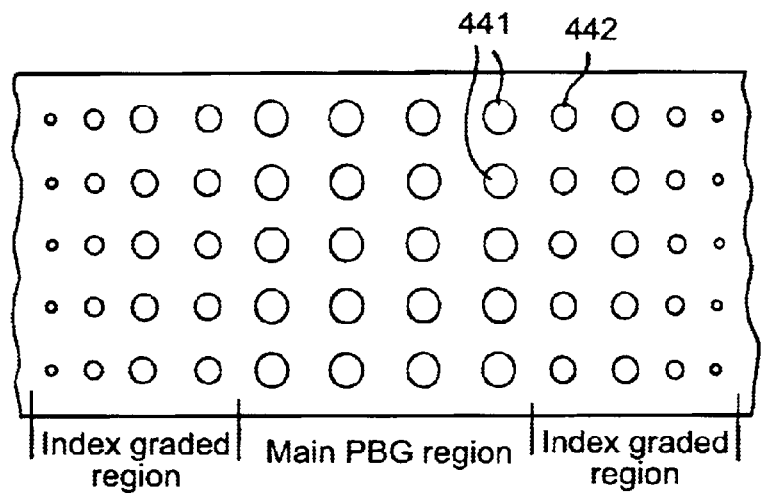
Figure 45:
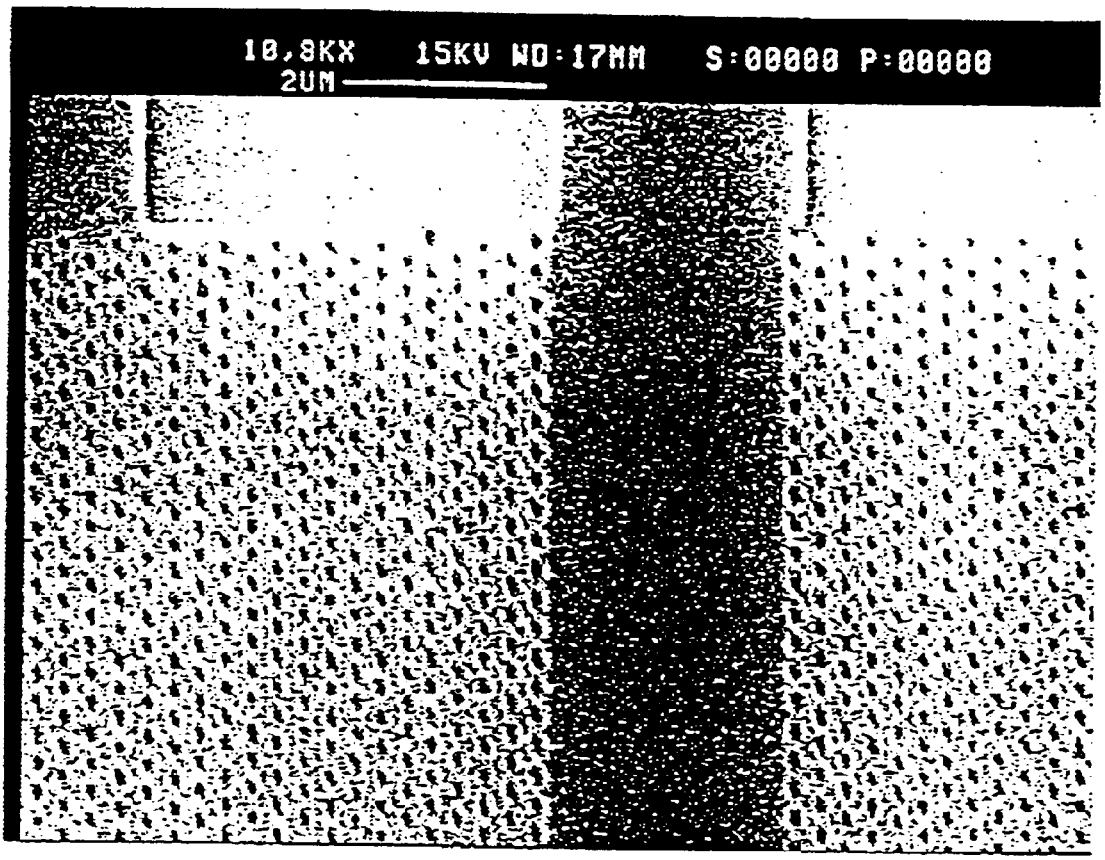
Figure 46:
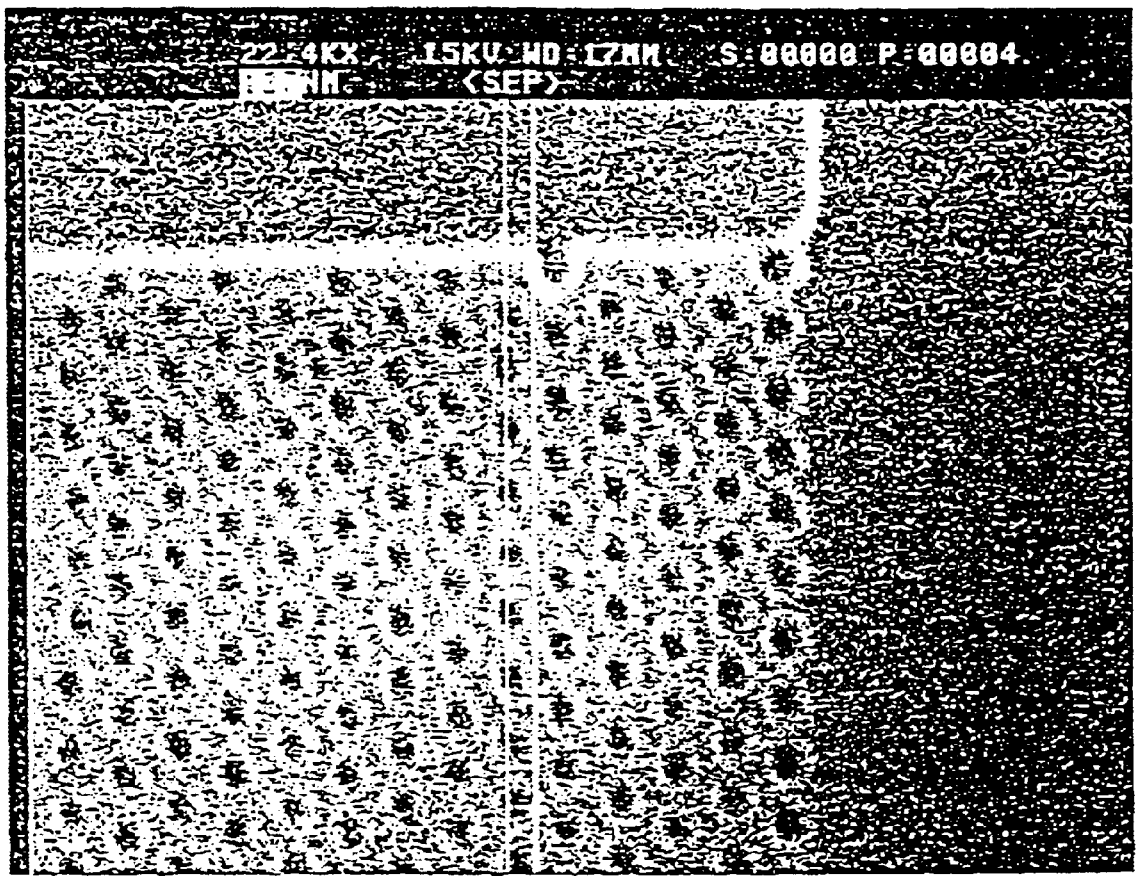
Figure 47:
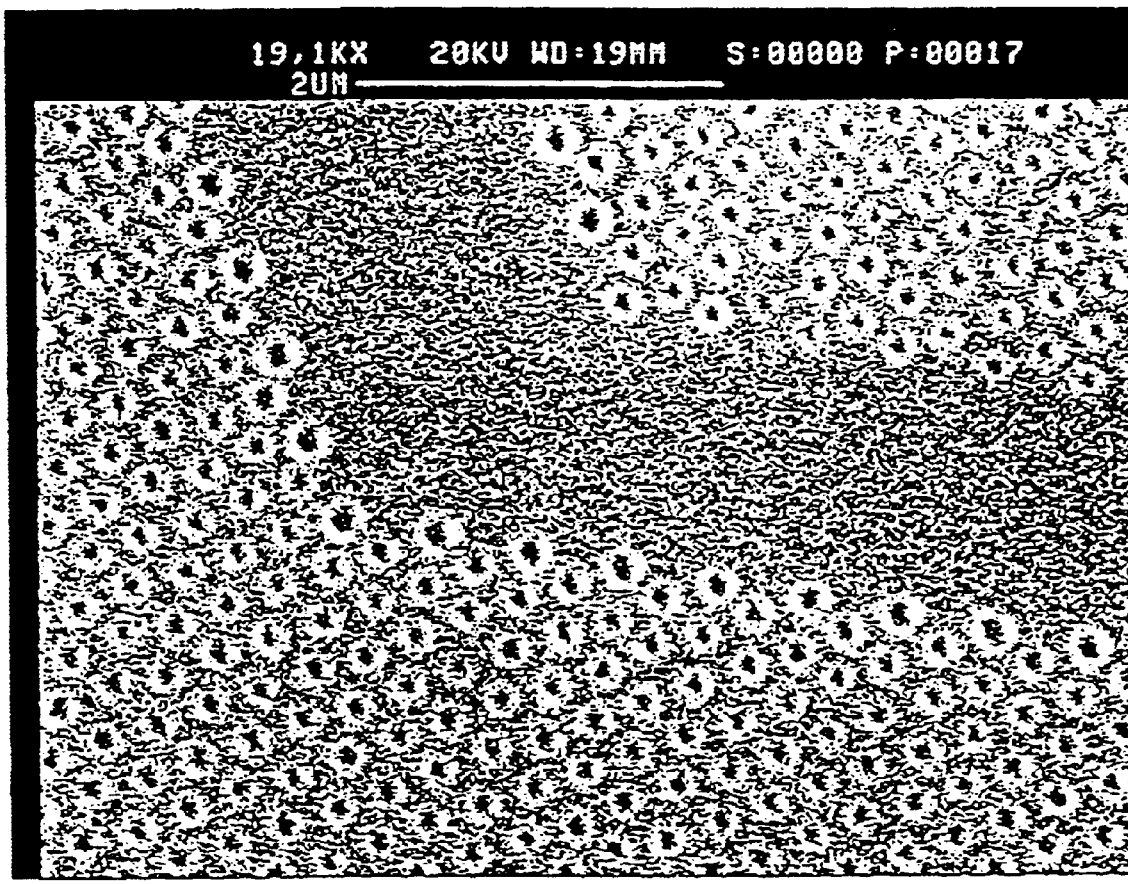
Figure 48:
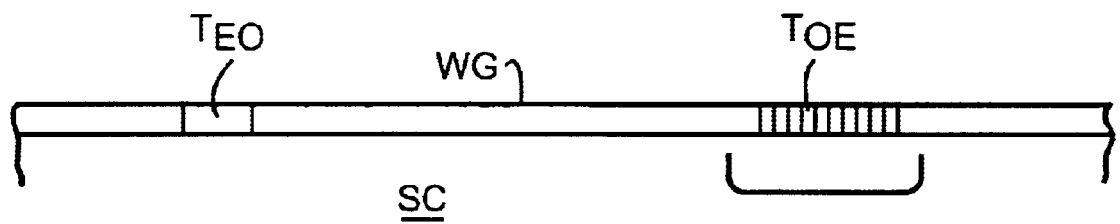
Figure 49:
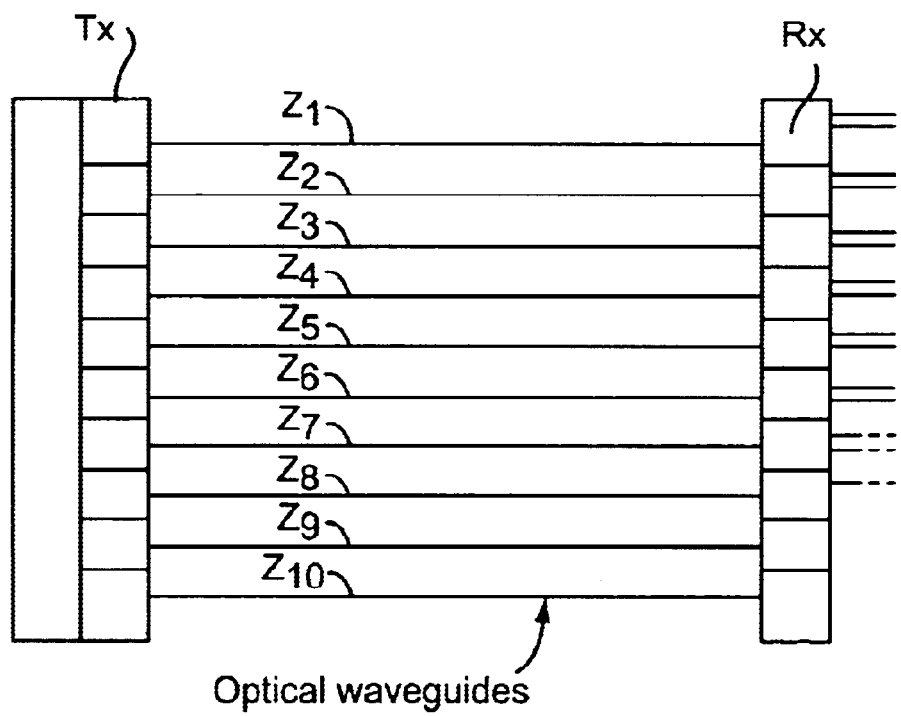

FIGS. 19a and b are photographs showing transmission of red and green light respectively;

FIG. 20 illustrates the propagation of different radiation modes in a waveguide;

FIG. 21 is a photonic band gap explanatory diagram;

FIG. 22 is another explanatory diagram illustrating guide mode propagation;

FIGS. 23a to 23n shows diagrammatically steps in fabricating a face plate;

FIG. 24 shows a face plate made by the method illustrated in FIG. 8;

FIG. 25 is a schematic view of a PBG device;

FIGS. 26 and 27 are scanning electron micrographs of PBG structures;

FIGS. 28–32 and 35–36a and b are photographs showing propagation of light through PBG structures;

FIGS. 33 and 34 are explanatory diagrams;

FIGS. 37 and 38 are schematic views of PBG structures;

FIGS. 39–41 are optical components using PBG structures;

FIG. 39 is a diagrammatic view of three cascaded band gap devices for 'group' demultiplexing, or for band gap narrowing;

FIG. 40a is an overall diagrammatic view of a complete wavelength demultiplexer (WDM) incorporating several optical devices of a type shown in FIG. 1. In this arrangement the demultiplexer is composed of two separate substrates, one supporting the optical devices, and the other supporting an opto-electronic detector array. The substrates are butted together to allow optical coupling between the two. The device has a single integrated optical input waveguide channel, which is then split to route the signal to several optical devices. The reduced bandwidth output signals from the optical devices are then routed to individual optoelectronic detectors via integrated optical waveguides;

FIG. 40b is a diagrammatic plan view of a hybrid or monolithic device. Further to the description of FIG. 40a, in a hybrid arrangement, the optoelectronic detectors may be fabricated from a completely different material, and are inserted into recesses fabricated into the substrate, which supports the optical devices. The recesses are designed so that there is good optical coupling from the integrated optical waveguides to the optoelectronic detectors. In a monolithic arrangement, the optoelectronic detectors are fabricated on the same substrate with optically compatible materials. This removes the coupling interface between the optical device and the opto-electronic detector, improving the efficiency of the device further;

FIG. 40c is a diagrammatic representation of part of an advanced monolithic or hybrid device, where further electrical amplification or signal processing circuitry is fabricated on the substrate supporting the optical devices. Again, the detectors may be monolithically integrated as well, or inserted into recesses on the substrate;

FIG. 41a shows a diagrammatic plan view of an arrangement of the optical device, which allows a sharp bend to be incorporated along the length of an integrated planar waveguide. This may be part of a complicated VLSI optoelectronic circuit. In this arrangement, large-scale integration of optoelectronic devices upon a single substrate is made possible;

FIG. 41b shows a diagrammatic plan view of an optical device acting as an integrated optical waveguide splitter. This may be part of a more complicated VLSI optoelectronic circuit;

FIG. 42a to d are graphs of frequency response of different pass band gap materials;

FIG. 42a and 42b show a broad stop band characteristic, which may be achieved by the geometry shown in FIG. 37a. By cascading devices with these characteristic as depicted in FIG. 39, a device with a narrower stop band shown in FIG. 7c may be achieved;

FIG. 42d shows a narrow pass band characteristic, which may be obtained by the inclusion of lattice defects examples of which are shown in FIGS. 37b and 37c;

FIG. 43 shows an interface between media of different refractive indices in a waveguide;

FIGS. 44a and b are diagrammatic representations of embodiments of the invention;

FIGS. 45 to 47 are scanning electron micrographs illustrating features of the invention;

FIGS. 48 and 49 are diagrammatic representations of further embodiments; and

FIGS. 50 to 57 are graphical representations used in relation to computer simulation of embodiments of the invention.

DETAILED DESCRIPTION OF THE INVENTION

Photonic band structures are useful in a host of passive applications as integrated optical devices for optical computing and optical communications. For example, arrays of PBG filter devices can be arranged to function as a fully integrated monolithic WDM demultiplexer. Whilst most active applications require a complete photonic band gap for both TE and TM polarisation states simultaneously, polarisation dependence may be usefully exploited in a passive optical device.

An important requirement for many passive integrated optical applications is low transmission loss away from the primary band gap region. We have devised a method which enables us to determine the mode structure and broadband transmission characteristics of a waveguiding PBG device to ensure strong transmission over a selected wavelength range. This method uses a three dimensional plane wave analysis [M. Plihal, A. A. Maradudin, *Physical Review B*, 44, 8565, (1991) and A. A. Maradudin, A. R. McGurn, *Journal of Modern Optics*, 41, 275, (1994)] to calculate the photonic dispersion relations for electromagnetic waves propagating within an infinitely thick slab of dielectric material, with a matrix of air rods etched through it. Standard waveguide theory may then be used to calculate the guided modes supported by a low dielectric lattice structure confined within a waveguide, by solving the electromagnetic (EM) boundary conditions at each layer, assuming an average refractive index for each etched layer. This three dimensional approach takes into account the finite wave propagation vector component aligned along the direction of the air rods, associated with the guided mode angle. This finite 'through plane' wave vector component can significantly modify the calculated dispersion relations. Since waveguide devices are in fact three-dimensional devices, the extra degree of freedom should, preferably, not be ignored.

While the energy eigenvalues associated with TE and TM polarised waves are inextricably linked as far as the calculations are concerned in the three dimensional plane wave analysis, the dispersion curves may be associated with a particular polarisation state once calculated.

Whilst there will be no photonic band gap for TM polarised waves in a low dielectric material, a relatively low dielectric material can support a significant photonic band gap for TE polarised waves, even for very low air filling fractions.

Figure 2:
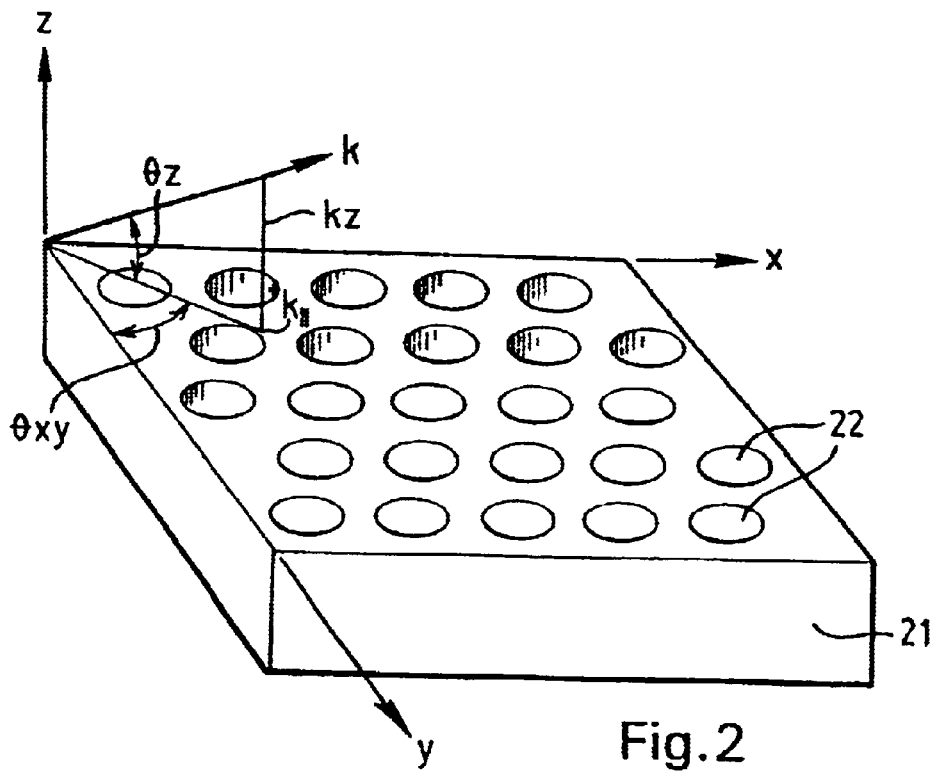

Referring to FIGS. 1 and 2 of the drawings, one embodiment of the invention comprises a waveguiding photonic crystal 21 which has a polarisation dependent optical band gap centred at 632.8 nm in the visible region of the spectrum. This structure consists of an array of air pores 22 arranged on a triangular lattice, etched through the core and cladding layers of a single mode silicon nitride waveguide grown on a silicon substrate (not shown). This device shows strong transmission for both polarisation states well below the lower band edge down to 545 nm, whilst completely inhibiting transmission of TE polarised red light at 632.8 nm. TM polarised red light is strongly transmitted.

Consider a planar photonic crystal lying in the x-y plane, the height of which extends in the z-direction. For the case when light propagates perpendicular to the air rods (so that the wave propagation vector k has no component in the z-direction), the wave can be resolved into two distinct polarisation states according to the orientation of the electromagnetic (EM) field components (FIG. 1). In this case Maxwell's field equations for the magnetic and electric field vectors may be solved separately to generate two independent photonic band diagrams [M. Plihal, A A Maradudin, *Physical Review B*, 44, 8565, (1991)]. This scenario will be referred to as 'in plane' wave propagation.

If the wave propagates at some angle with respect to the plane of the lattice (FIG. 2) so that there is a finite wavevector component resolved in the z-direction ($k_z$) then both the electric and magnetic field vectors will have some component resolved within the plane of the lattice. (This scenario will be referred to as 'through plane' wave propagation). In this case, the wave equations for the electric and magnetic field vectors are inextricably linked and we must solve a three-dimensional eigenvalue problem to derive the dispersion relations. However, the solutions for the E and H field vectors eventually converge to the same values. Consequently it is necessary to solve only one of the field equations to derive the full band structure.

For a three dimensional plane wave analysis, the propagation of a single mode wave $E(r)e^{i\omega t}$ of frequency $\omega=\omega(k)$ through a periodic dielectric structure can be expressed:

$$\nabla \wedge \nabla \wedge E(r,t) = \varepsilon(r)\frac{\omega^2}{c^2}E(r,t) \qquad \text{eqn 1}$$

r is a three dimensional position vector, k is the three dimensional wave vector.
c is the vacuum velocity of light, and $\in$ is a dielectric function.

In the Fourier domain (known as reciprocal lattice space in connection with solid state physics), the electric field vector may be represented by a Bloch expansion:

$$E[r,t] = \sum_G a(k,G)\exp[i(k+G)\cdot r] \qquad \text{eqn 2}$$

G 2 dimensional Reciprocal lattice vectors.
k 3 dimensional wave propagation vector.
r 3 dimensional position vector.
a(k,G) 3 dimensional Bloch vector coefficients The dielectric function can be represented by a Fourier series.

$$\frac{1}{\varepsilon(r)} = \sum_G C_G \exp(i\,G\cdot r) \qquad \text{eqn 3}$$

The Fourier coefficients $C_G$ are given by:

$$C_G = \frac{1}{\Omega}\int \varepsilon(r)\exp(-i\,G\cdot r) \qquad \text{eqn 4}$$

Employing Ho's matrix optimisation method [C. T. Chan, K. M. Ho, C. M. Soukoulis, *Europhysics Letters*, 16, 563 (1991)], the Fourier coefficients for a two dimensional lattice of rods of radius R, arranged in an equilateral triangular lattice, are given by the expression:

$$C_G = \begin{cases} f\varepsilon_a + (1-f)\varepsilon_b & G=0 \\ 2f(\varepsilon_a-\varepsilon_b)\dfrac{J1(|G|R)}{|G|R} & G\neq 0 \end{cases} \qquad \text{eqn 5}$$

$$f = \frac{2\pi}{\sqrt{3}}\left(\frac{R}{a}\right)^2 \qquad \text{eqn 6}$$

where a is the lattice pitch, $\in_a$ is the dielectric constant of the rod, $\in_b$ is the dielectric constant of the background dielectric, J1(x) is a first order Bessel function, and f is the volume air filling fraction.

Resolving eqn 1 along the cartesian co-ordinate axes x,y,z and substituting the expansions (eqns 2,3), the following set of wave equations describes the electric field vector in reciprocal lattice space.

x-component:

$$\sum_{G'} C_{(G_\parallel - G'_\parallel)} \left[ [(k_y + G'_y)^2 + k_z^2] a_{(k_\parallel + G'_\parallel)_x} - \right.$$

$$\left. (k_x + G'_x)(k_y + G'_y) a_{(k_\parallel + G'_\parallel)_y} - k_z(k_x + G'_x) a_{(k_\parallel + G'_\parallel)_z} \right] = \frac{\omega^2}{c^2} a_{(k_\parallel + G_\parallel)_x}$$

eqn 7a y-component:

$$\sum_{G'} C_{(G_\parallel - G'_\parallel)} \left[ -(k_x + G'_x)(k_y + G'_y) a_{(k_\parallel + G'_\parallel)_x} + \right.$$

$$\left. [(k_x + G'_x)^2 + k_z^2] a_{(k_\parallel + G'_\parallel)_y} - k_z(k_y + G'_y) a_{(k_\parallel + G'_\parallel)_z} \right] = \frac{\omega^2}{c^2} a_{(k_\parallel + G_\parallel)_y}$$

eqn 7b z-component:

$$\sum_{G'} C_{(G_\parallel - G'_\parallel)} \left[ -k_z(k_x + G'_x) a_{(k_\parallel + G'_\parallel)_x} - \right.$$

$$\left. k_z(k_y + G'_y) a_{(k_\parallel + G'_\parallel)_y} + (k_\parallel + G'_\parallel)^2 a_{(k_\parallel + G'_\parallel)_z} \right] = \frac{\omega^2}{c^2} a_{(k_\parallel + G_\parallel)_z}$$

eqn 7c

The E-field vector has been resolved along each cartesian co-ordinate axes x,y,z.

$k_\parallel$ are wave propagation vector components resolved within the plane of the lattice $G_\parallel$ are reciprocal lattice vectors, $\omega^2/c^2$     are scalar energy eigenvalues $a_{(k_\parallel + G_\parallel)_{x,y,z}}$     are 3 dimensional Bloch vector coefficients, $C_{(G_\parallel - G'_\parallel)}$     are scalar Fourier coefficients.

Together these expressions take the form an inseparable, three dimensional, eigenvector problem (eqn 8) which can be constructed and solved by computer, taking each k vector in turn.

$$\begin{bmatrix} Mx(y,z) & Mx(x,y) & Mx(z,x) \\ My(x,y) & My(x,z) & My(z,y) \\ Mz(z,x) & Mz(z,y) & Mz(x,y,z) \end{bmatrix} \cdot \begin{bmatrix} a_{(k_\parallel + G_\parallel)_x} \\ a_{(k_\parallel + G_\parallel)_y} \\ a_{(k_\parallel + G_\parallel)_z} \end{bmatrix} = \frac{\omega^2}{c^2} \cdot \begin{bmatrix} a_{(k_\parallel + G_\parallel)_x} \\ a_{(k_\parallel + G_\parallel)_y} \\ a_{(k_\parallel + G_\parallel)_z} \end{bmatrix}$$

eqn 8

Mx–Mz are numerical functions of the cartesian variables shown in brackets. Each function constructs a square submatrix addressed by the reciprocal lattice vectors G and G'. This expression may be solved for a triangular lattice of air holes ($\in_a=1$) in a silicon nitride background dielectric ($\epsilon_b=4$), with a lattice pitch $\Lambda$. The primitive translation vectors are:

$a=\Lambda(1,0)$ and $b=\Lambda(\frac{1}{2},\sqrt{3}/2)$.

The corresponding primitive reciprocal lattice vectors are:

$$A = \frac{2\pi}{\Lambda}\left(1, -\frac{\sqrt{3}}{3}\right) \text{ and } B = \frac{2\pi}{\Lambda}\left(0, \frac{2\sqrt{3}}{3}\right).$$

A sample set of reciprocal lattice vectors is given by:

$G=mA+nB$ (m,n are addressing integers).

k vector samples are taken around a reduced Brillouin zone segment defined by lattice symmetry points to construct a photonic band diagram. By repeating the calculations for various values of $k_z$ the behaviour of the dispersion curves is mapped as a function of mode angle $\theta_z$ for a fixed air filling fraction.

Figure 4:
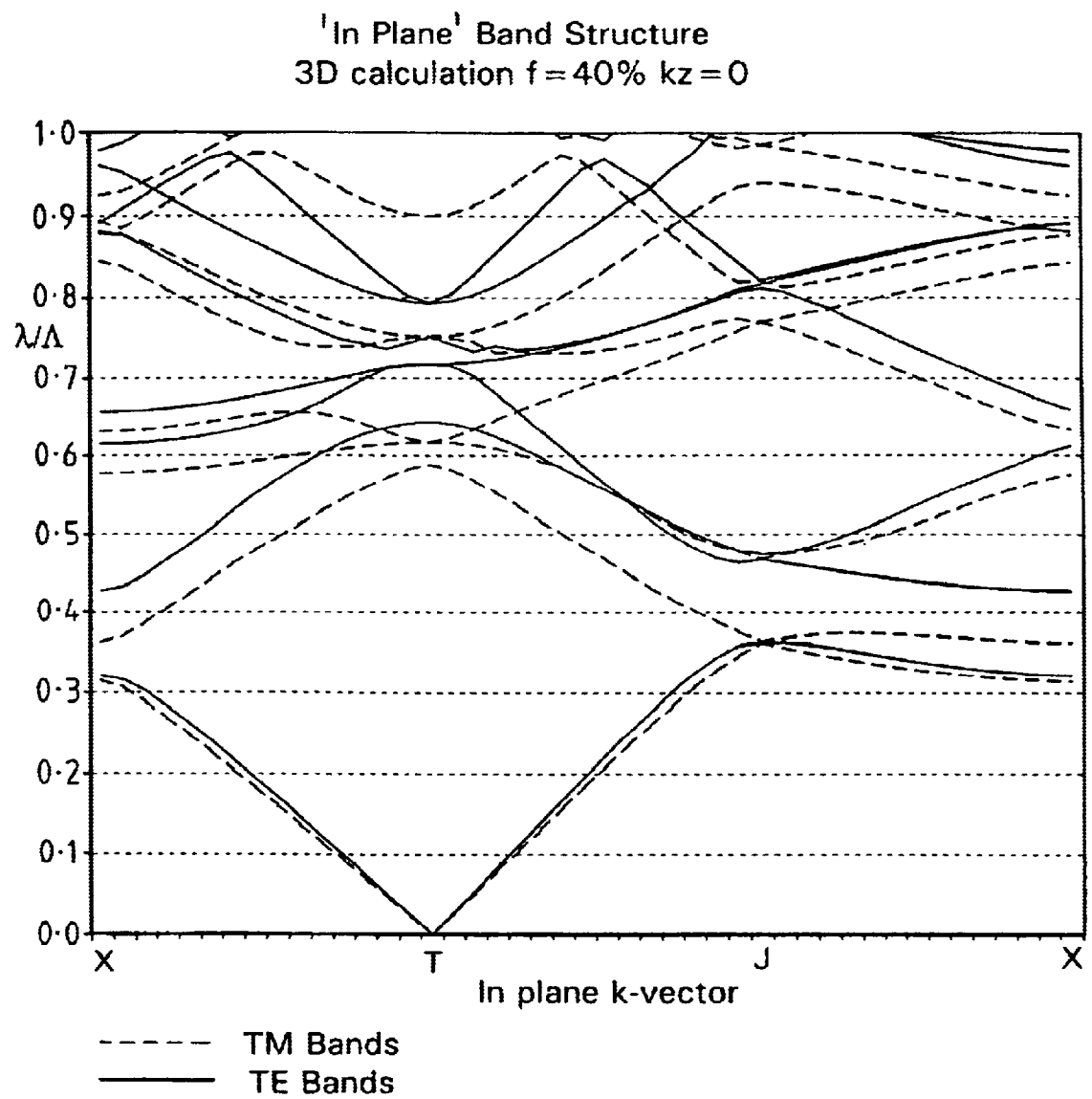
Figure 5:
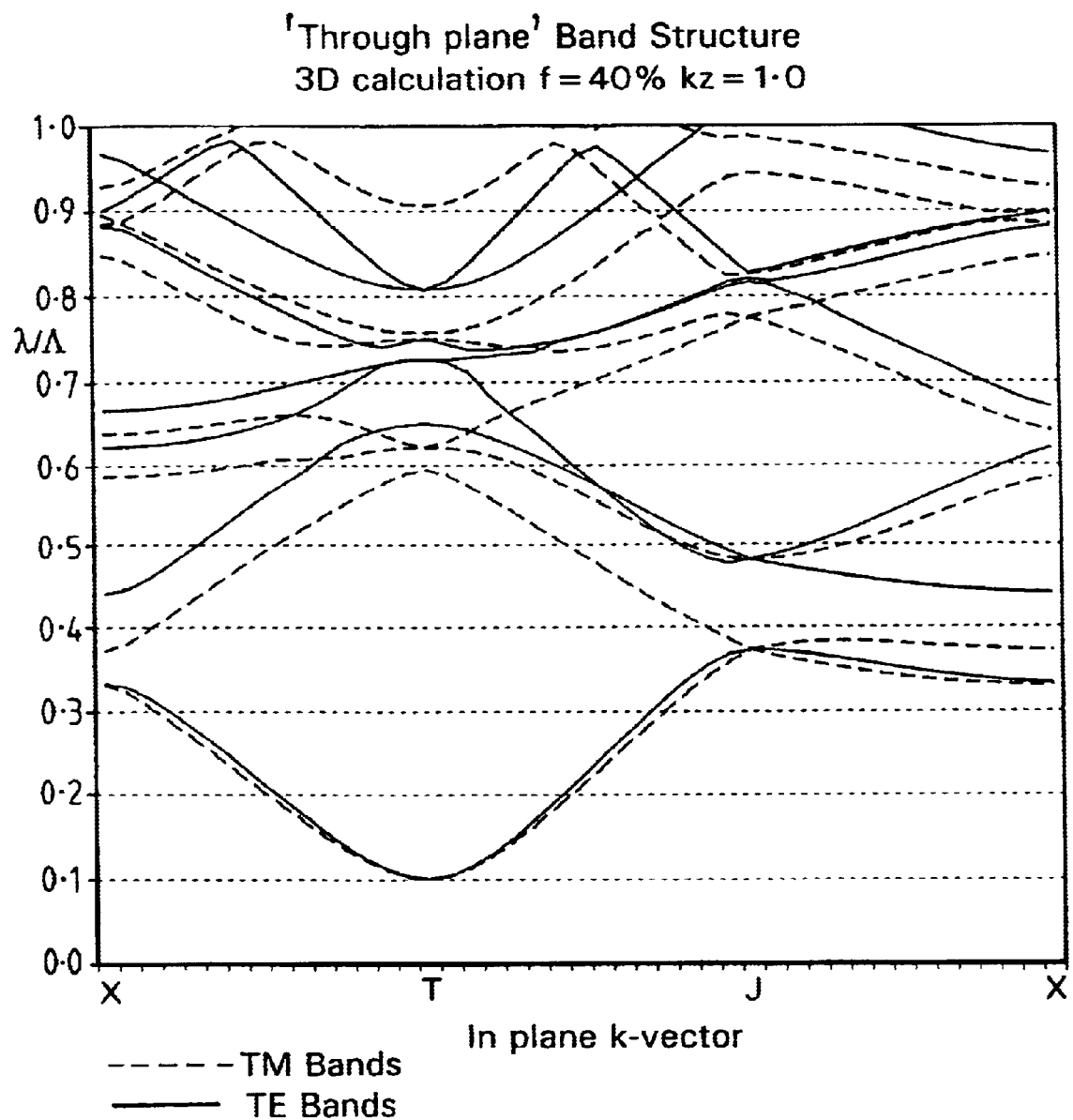

The evolution of the dispersion curves as the mode angle is increased from 0° (in plane wave propagation) to 90° (normal incidence or 'through plane' wave propagation), indicates that, while the energy eigenvalue solutions for the TE and TM polarised states are inextricably linked as far as the calculation problem is concerned, each dispersion curve may be associated with a particular polarisation state once calculated. This is illustrated by FIGS. 3 to 5.

Figure 3:
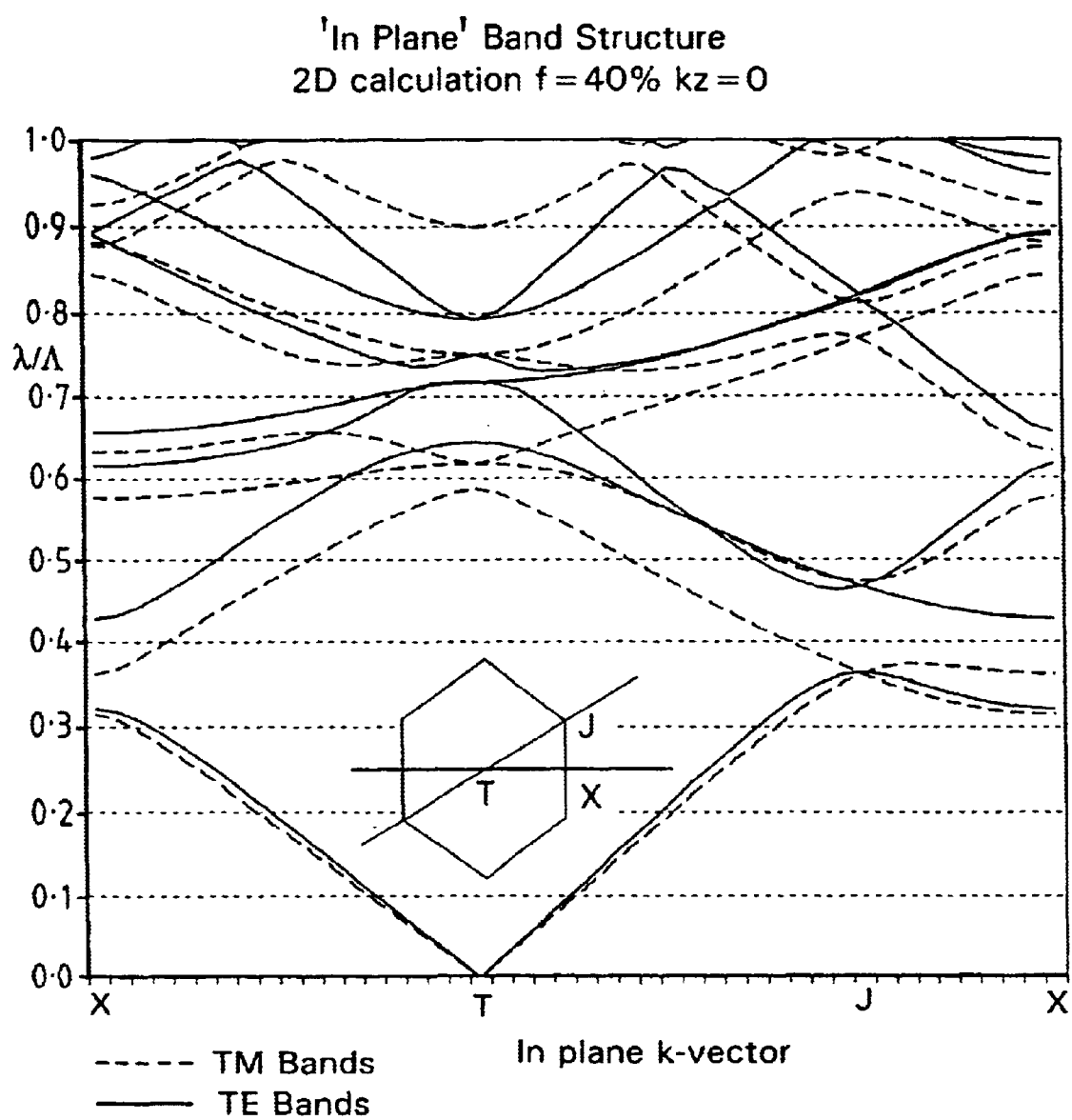
FIGS. 3 to 5 show energy band structures of materials.

FIG. 3, shows the band structure for a lattice of air rods in a silicon nitride background dielectric with a volume air filling fraction of 40%, calculated using a conventional two dimensional plane wave analysis using 81 plane waves in conjunction with Ho's inverse transform matrix method. The dispersion relations for the two polarisation states have been superimposed for ease of comparison. FIG. 5, shows the 'in plane' band structure calculated using the three-dimensional plane wave analysis with $k_z=0$. The dispersion relations are identical. Consequently, each dispersion curve in FIG. 4 can be associated with a particular polarisation state by comparison with FIG. 3. As the 'through plane' component $k_z$ is increased (FIG. 5), a gap appears below the first two dispersion curves at the T point, the dispersion curves rise and becomes slightly compressed. However, the shape and degenerate points of the curves remain unchanged, and each dispersion curve can again be associated with a particular polarisation state.

Figure 6:
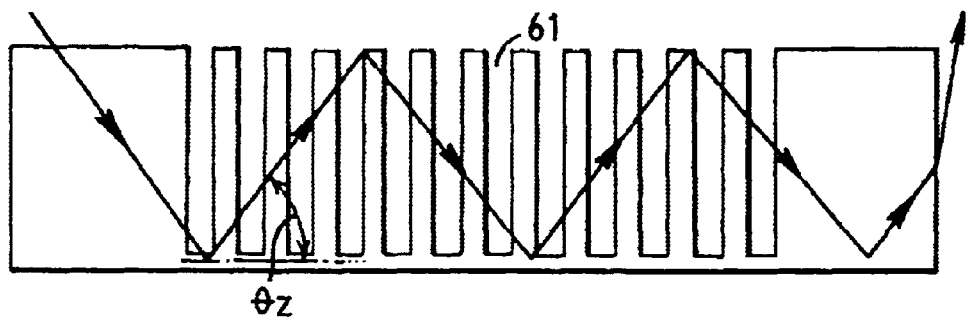
FIG. 6 is a diagrammatic representation of a simple 3-layer planar waveguide.

The mode structure of a simple 3-layer planar waveguide (FIG. 6) can be derived by solving two principle boundary conditions. The first condition is that the mode angle at the boundary must be less than the critical angle $\theta_{crit}$ for total internal reflection, otherwise the light will quickly leak out of the waveguide.

$$\theta crit = \cos^{-1}\left(\frac{n}{nc}\right)$$

eqn 9 n=refractive index of cladding, nc=refractive index of core

Since the dimensions of the holes 61 are of the order of $\lambda/4$ to $\lambda/2$ near the band gap, they cannot be resolved by the propagating waves. Instead, the etched layers will appear to have a reduced refractive index given by the average refractive index.

$n_{avg}=(nb-na)\cdot(1-f)+na$ eqn 10 na=refractive index of holes nb=refractive index of dielectric

Secondly, a transverse phase matching condition must be met in order for a resonant guided wave to build up.

$m\cdot\lambda=k_z\cdot\Lambda-\phi$ eqn 11 m=integer $\phi$=sum of phase changes at boundaries.

$\Lambda$=lattice pitch,

Making substitutions for $k_z$, the transverse resonance condition may be re-arranged to give the wavelength of a guided mode as a function of mode angle.

$$\lambda = \text{Re}\left[-\frac{4\cdot\cos(\theta_z)\cdot n_{avg}\cdot d\cdot\Lambda\cdot\pi}{(-\phi(\theta_z, n_b) - \phi(\theta_z, n_c) + 2\cdot\pi\cdot m)}\right]$$

eqn 12

$\theta_z$=mode angle $n_{avg}$=average refractive index of core.

$\phi(\theta_z,n)$=p hase change at boundary $n_b$=average refractive index of buffer layer $n_c$=average refractive index of cladding layer d=core thickness m=mode number $\Lambda$=lattice pitch The phase change upon reflection from a waveguide boundary is different for each polarisation state. This causes the separation of the polarisation states as unpolarised light propagates along a planar waveguide.

Phase change for TM modes:

$$\phi(\theta z, n, nc) = \left[\tan^{-1}\left[\frac{\sqrt{\sin(\theta z)^2 - \frac{n^2}{nc^2}}}{\cos(\theta z)^2}\right]\right] \quad \text{eqn 13 a}$$

Phase change for TE modes:

$$\phi(\theta z, n, nc) = \left[\tan^{-1}\left[\frac{\sqrt{\sin(\theta z)^2 - \frac{n^2}{nc^2}}}{\cos(\theta z)^2 \cdot \frac{n^2}{nc^2}}\right]\right] \quad \text{eqn 13 b}$$

n=refractive index of cladding nc=refractive index of core $\phi z$=mode angle

Figure 7:
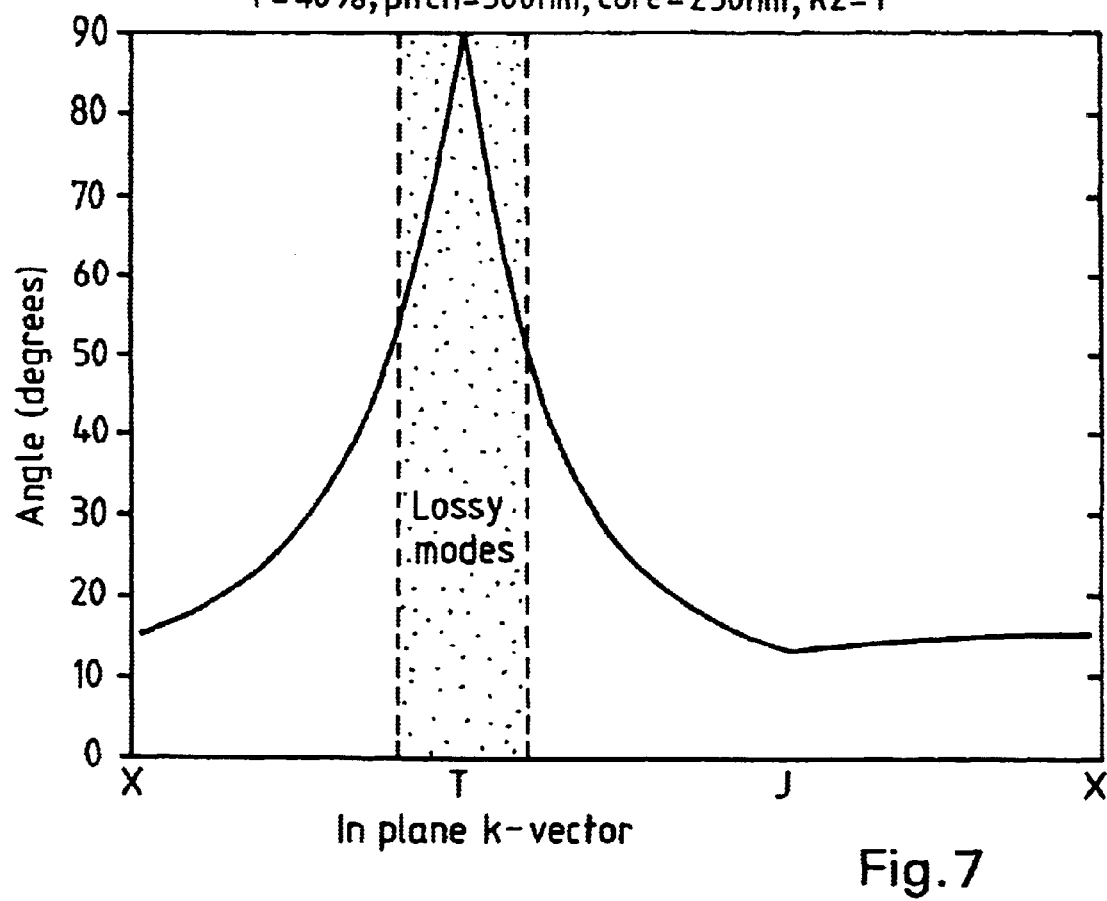
FIGS. 7 and 8 show guided mode propagation in a silicon nitride PBG waveguide.

The wave-guide model may now be combined with the plane wave analysis. If $k_z$ is greater than zero, then a waveguide mode angle can be associated with each k-vector along the x-axis of the photonic band diagram (FIG. 7). The mode angle for the zero momentum k-vector at the T point however, remains ambiguous.

$$\sin\theta_z = \frac{k_z}{|k|}$$

"Through plane" mode angle      eqn 14

The wavelength of the guided mode is now calculated as a function of mode angle for a fixed waveguide geometry and superimpose this upon the three dimensional band diagram. (FIG. 8). The points where the guided mode lines intersect the dispersion curves indicate the solutions of the guided Bloch modes supported by the PBG structure [D. M. Atkin, P. St. J. Russel, T. A. Birks, *Journal of Modern Optics*, 43, 1996, (1035)]. These show which wave vectors must be excited to obtain transmission across the PBG structure at a particular wavelength. Whether or not guided modes can exist at a particular wave length, may be determined by studying the evolution of the dispersion curves for a range of values of $k_z$. This may be achieved graphically by animating a series of band diagrams, looking for points of intersection between dispersion curves and the guided mode lines at a particular test wave length. If there are no guided Bloch modes for any value of $k_z$, then a photonic band gap exists at that wavelength, and that the normal waveguide mode has been suppressed by the band structure. In performing this analysis, it should be borne in mind that each dispersion curve can be associated with a particular polarisation state. The field intensity profile for a guided Bloch mode throughout the lattice structure may be constructed by returning to the eigenvector problem, and solving the eigenvectors for the guided Bloch wave vector.

FIG. 8 is an example of a 'three dimensional' band diagram for a silicon nitride structure showing the existence of a TM polarised guided mode at 545 nm along the T-J symmetry direction, and a TM polarised guided mode at 600 nm along the T-X direction. Wave-vectors centred about the zero momentum point T, correspond to modes at near normal incidence to the structure (FIG. 7). These are leaky modes exceeding the critical angle for total internal reflection. Consequently, the guided mode lines are discontinuous at these boundaries. The vertical lines in FIG. 7 indicate the limit for total internal reflection.

The group velocity of a wave propagating in a waveguide is given by:

$$V_g = \frac{\partial\omega}{\partial k} \quad \text{eqn 15}$$

This indicates that Bloch waves at points of inflection on the dispersion relations (mostly at the symmetric points) will, astonishingly, have zero group velocity. By coupling light directly into these modes then a high quality-factor, standing wave would build up.

In a conventional waveguide, light is confined by total internal reflection within a high dielectric region, surrounded by a lower dielectric medium. The refractive index contrast required to maintain a guided mode can be extremely small. This principle may be employed in association with PBG waveguides. (FIG. 9) For example, by etching small holes 91 through a waveguide structure, the effective index of the etched layers may be reduced. This modifies the mode structure in the etched region of the waveguide. In order to confine the light within the photonic lattice, it is necessary to ensure that the effective index of the core 92 remains greater than that of the cladding 93 and buffer 94 layers. This condition is met at the core/cladding interface, by etching the holes through both the cladding and core layers, since the effective index of both layers is reduced in the same ratio (FIG. 9a). The main problem arises at the substrate buffer layer. For a silicon dioxide/silicon nitride material system, the maximum volume air-filling fraction is limited to 40%, which limits the maximum bandwidth of the PBG.

The maximum volume air-filling fraction may be extended by isolating the etched region of the waveguide from the buffer layer by means of an air cavity 95 (FIG. 9b). However, this may cause stress related structural problems in many material systems for more than a few lattice periods. Another solution is to over etch the holes 91 so that they extend well into the isolating buffer layer (FIG. 9c). Again, this reduces the effective index in the same ratio as the core.

FIGS. 10–12 show examples of the guided mode profile for silicon nitride waveguide structures in each mode of operation. The percentage figures indicate the proportion of the mode intensity within each layer. The estimated attenuation is also shown. The profile shown in FIG. 10 is the most usual mode of operation employed in such structures, close to the volume air filling fraction limit. A large proportion of the mode is within the buffer layer. It shows that these silicon nitride structures should be capable of supporting a waveguide mode for both polarisation states. This guided mode will be suppressed by the photonic lattice and this has been demonstrated with a PBG working in the visible spectrum.

FIG. 11 indicates that a totally isolated waveguide structure would give a well confined mode even for a very small isolating air gap. FIG. 10 indicates that the etch must extend a considerable distance into the buffer region to avoid creating an excessively lossy waveguide mode.

In practice, the waveguide devices consist of three separate monolithically integrated devices—an input waveguide, a PBG region and an output waveguide. For low loss transmission, there should, preferably, be strong mode coupling between the PBG region and the input and output waveguides, bearing in mind that there is a change in average refractive index at the boundary.

Although light will couple into any available mode within the PBG region at the boundary, coupling will be most efficient when there is a large mode overlap in the two regions (FIG. 13). Ideally the waveguide mode should refract directly into a PBG guided mode at the dielectric interface. Back reflections may also occur at the boundary causing loss. The input and output waveguide mode angles and profiles for. a particular wavelength of interest may be fine-tuned by reducing or increasing the relative thickness of the PBG core region.

Nanostructures, have been fabricated with a polarisation-dependent photonic band gap centred at 633 nm in the visible region of the spectrum. Devices constructed in accordance with the above embodiments have permitted the observation, with the naked eye, of the behaviour of light as it propagates through a PBG structure.

Devices in accordance with a particular aspect of the invention are based on a triangular lattice of air pores plasma etched through the cladding and core layers of a single-mode silicon nitride waveguide (FIG. 8). The waveguide consists of a thermally grown, 1.8 $\mu$m thick silicon dioxide substrate buffer layer (n=1.46), a 250 nm thick silicon nitride waveguiding layer (n=2.02) deposited by Low Pressure Chemical Vapour Deposition (LPCVD), and a thin (75–180 nm) silicon dioxide cladding layer, also deposited by LPCVD. The wafers are then patterned by direct-write electron beam lithography and plasma-etched to create wells extending down to the core/buffer interface. The wafers are finally cloven into individual devices for optical testing.

We have found that it is considerably easier to create extremely narrow pores than wider ones at a submicron pitch since the resist walls forming the narrow rib between adjacent pores tends to collapse as the diameter is increased. Pores with diameters in the range 50 to 120 nm were easily fabricated using standard processes. In order to create a photonic band gap however, a volume air-filling fraction of over 20% is required. Our solution was to develop a well-controlled process to permit the lateral expansion of the pores after an initial isotropic plasma etch. This permits fine-tuning of the photonic band gap after initial fabrication.

Using lithography and plasma etching processes to facilitate the expansion of the pores, it is possible to fabricate good quality pores with diameters in the range 50 nm–200 nm at a pitch of 260 nm through waveguide structures well over 500 nm thick. Furthermore, the pore profile may be modified to create the isolated waveguide structures discussed above.

FIG. 23 is a scanning electron micrograph (SEM) which shows a cross section through a waveguiding PBG structure. This consists of a 260 nm pitch triangular lattice of air pores etched to a total depth of 475 nm. A two-stage dry etching process was employed to etch through the silicon nitride core and part way through the underlying silicon dioxide buffer layer, creating a reduced refractive index buffer layer below the main waveguide core. Half way down the pore, there is a clear step in pore diameter (from 150 nm to 75 nm) marking the point where the process was changed. Despite the minute pore diameter, the walls are extremely isotropic in both sections. This structure forms the starting point in the fabrication of a large air filling fraction device operating in the regime shown in FIG. 8.

Figure 15:

After the initial plasma etch, the pore diameter can be expanded in the silicon nitride layer only, by a material-specific wet etch process. SEM FIG. 15, shows a 300 nm pitch triangular lattice structure. In this case, the dry etch process transition occurred half way through the silicon nitride layer. The diameter step clearly visible in FIG. 15 has become rounded by the wet etch process giving an apparent taper to the pore. The thin cladding layer rests on top forming a protective cap. The pore diameter starts at 30 nm in the buffer layer then tapers from 115 nm to 173 nm in the nitride layer, with a reduced diameter of 95 nm in the cladding layer.

The isotropy of the pore walls may be greatly increased by a special pre-etch priming process used in conjunction with careful post-etch cleaning and drying. This ensures a rapid and uniform-etch start and stop. This can be seen in SEM FIG. 16. Again there is a step in pore diameter in the nitride layer (from 250 nm to 175 nm) due to the initial plasma etch process transition. The pore diameter starts at 120 nm in the cladding layer.

Figure 14:
Figure 16:
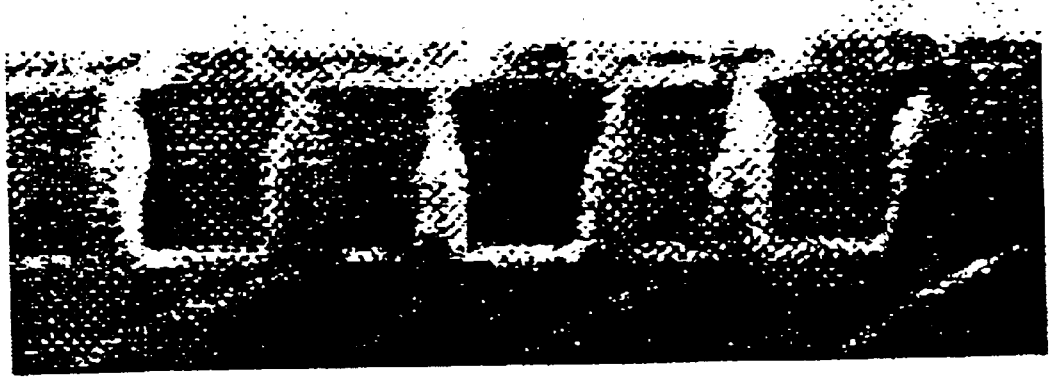
Figure 17:
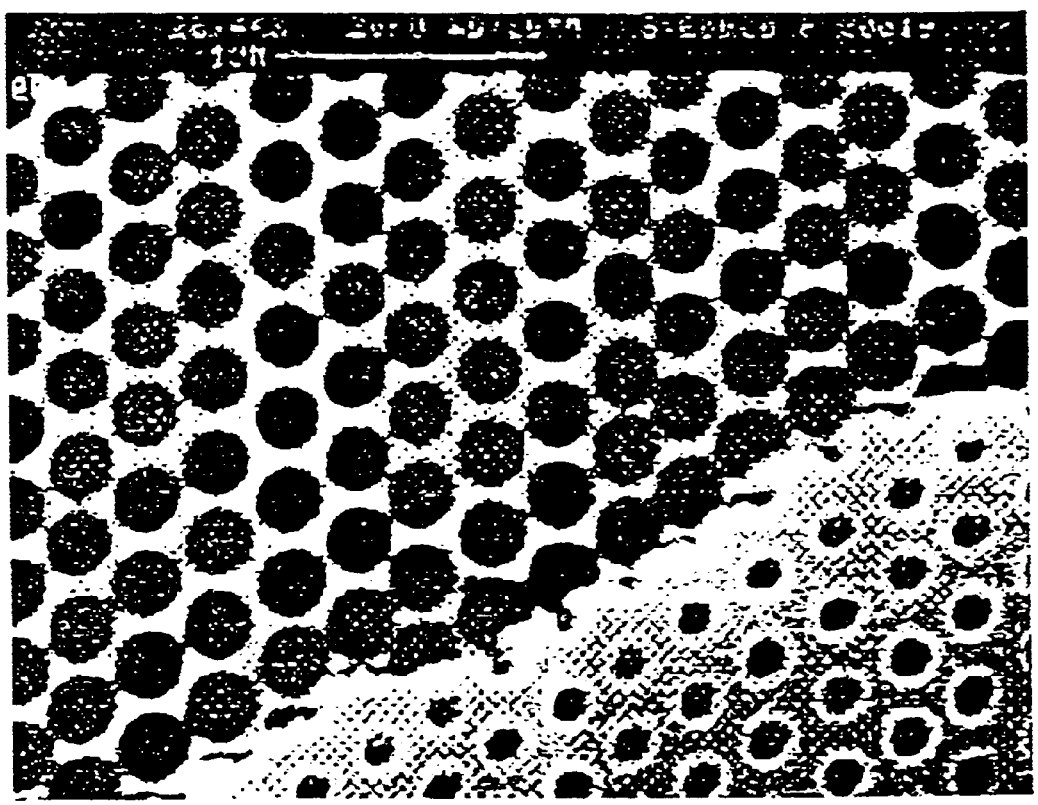
Figure 18A:
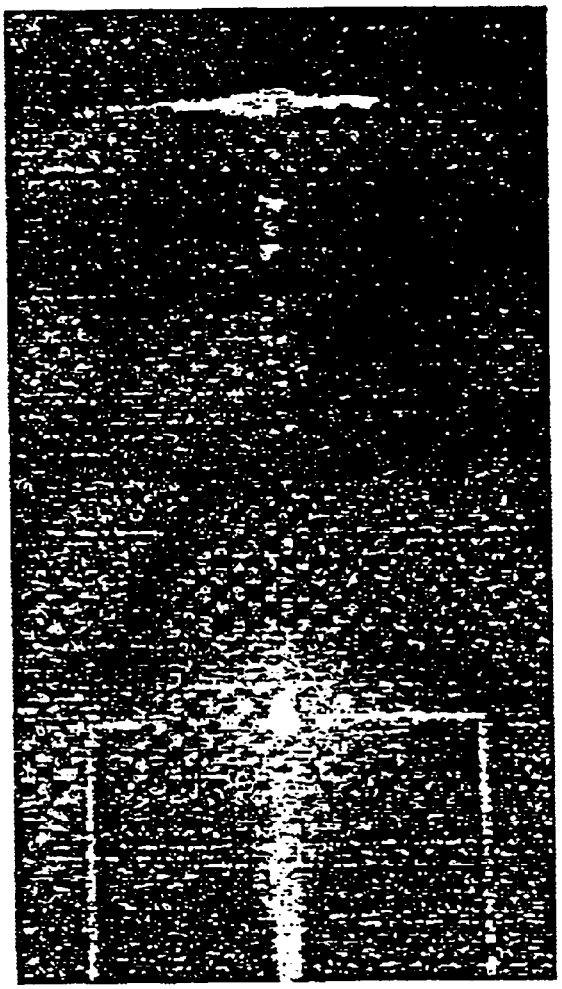
Figure 18B:
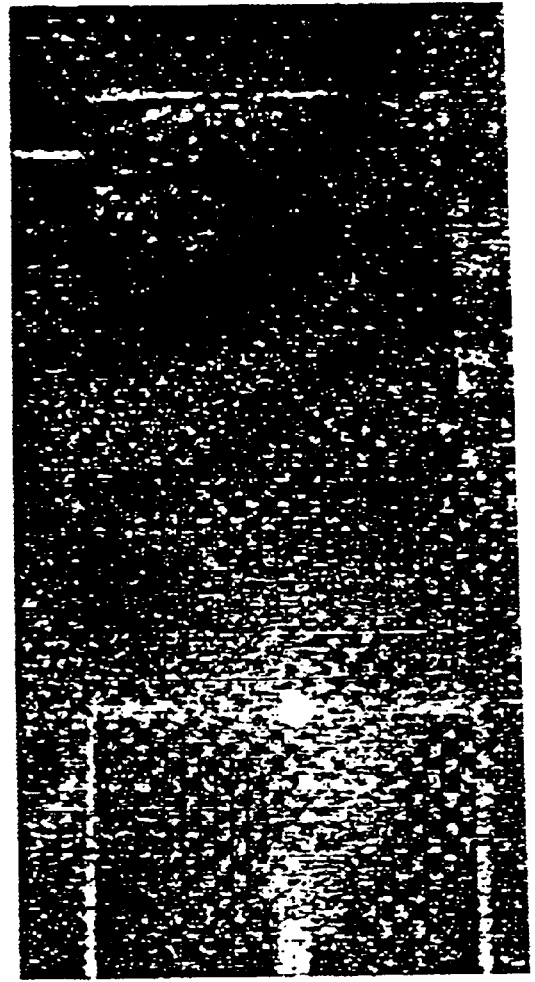

A similar process may be applied to the oxide buffer layer, to undercut the porous silicon nitride waveguide core once the desired pore diameter has been obtained, creating an air cavity as depicted in FIG. 9b. Unfortunately, this kind of structure is extremely fragile and may collapse due to stress induced by thermal cycling during original layer growth if more than a few lattice periods are required. This may be obviated by creating a honeycomb of very porous silicon dioxide, which. will still support the less porous waveguide core. This may be achieved by carefully expanding a narrow capillary etched part way into the silicon dioxide buffer layer (FIGS. 14 and 16). The end result is shown in SEM FIG. 17. Here the silicon dioxide cladding layer has been removed to reveal a section of silicon nitride wave guide core (at the lower right corner) resting on top of the porous silicon dioxide buffer layer. The pore diameters are 135 nm in the silicon nitride waveguide core and 250 nm in the silicon dioxide buffer layer. The quality of the pores is extremely good in the under-etched buffer layer, with surprisingly straight pore walls.

A test sample used in the development of the pore expansion process demonstrated the existence of a visible photonic band gap in a waveguide. This consisted of 2730 rows of air pores, arranged in a triangular lattice with a pitch of 300 nm, etched across a blanket waveguide layer. The pores had a diameter of 200 nm giving a volume air-filling fraction close to 40%.

In fabricating the holes there may be a need to compensate for optical scattering and edge effects. This may be achieved by associating a particular clock speed for each hole or line of holes. In some instances, to achieve the correct resist exposure it has proved necessary to de-focus the E-beam to avoid 'resist flipping' from positive to negative.

A device in accordance with a particular embodiment, shows strong transmission of TE and TM polarised green light (545 nm) for both polarisation states (FIGS. 19a,b). Although the beam track for TM polarised light is clearly visible on both sides of the PBG region, further confirmation of transmission for both polarisation states is given by a bright spot at the top edge of the wafer. This indicates the position of the emergent beam.

From a classical point of view, short wavelength guided modes might be expected to be strongly suppressed by Rayleigh scattering from even the smallest waveguide defects. On this scale, the air pores are absolutely massive. The transmission of green light across thousands of periods of holes, combined with the polarisation sensitive suppression of transmitted modes at 632.8 nm demonstrates the existence of an optical band gap in the red.

An alternative method of determining the structure of PBG waveguides is to solve the waveguide boundary conditions simultaneously with the photonic band structure using the plane wave method. Since the plane wave method involves a rigorous solution of Maxwell's equations at many sample points across the lattice, the results are absolute and non dependent upon an ambiguous value of effective refractive index.

For a metallised waveguide, the boundary conditions state that the x and y components of electric field must diminish to zero at the two waveguide boundaries, and consequently, (to preserve the propagating wave-vector) the z-component must be at a maximum.

$$E_x = E_y = 0 \text{ at both boundaries } (z=0,d) \qquad \text{eqn. 16}$$

For a dielectric waveguide, however, the boundary conditions are slightly different. In this case, there is an evanescent field penetrating into the cladding and substrate buffer layers. Consequently, all the field components must be continuous across the boundary. They will then diminish to zero some distance outside the waveguide core.

The general boundary conditions for any waveguide are expressed by the transverse phase matching condition.

$$k_z = \frac{(m\pi - \phi)}{d} \qquad \text{eqn. 17}$$

$\phi$ is the sum of the phase changes upon reflection from the waveguide boundaries.

m is an integer mode number $k_z$ is the magnitude of the propagating wave-vector resolved along the z-direction, measured within the waveguide core d is the waveguide core thickness This effectively states that the waveguide must allow an integer number of modes to exist in the transverse direction to the waveguide (across the thickness of the waveguide) as indicated in FIG. 20.

In order to modify the plane wave method to include the transverse phase matching condition, all that is necessary is to modify the Bloch expansion terms (resolved along the Cartesian co-ordinate axes) to include the transverse phase matching condition since these are the ones which describe the field components at all points within the structure.

Once the result filters through to the final set of equations which form the three dimensional Eigen-system, (solved to give the band structure), we see that all we need do is evaluate the band structure for values of $k_z$ which satisfy the phase match condition for the mode number of interest.

If we then solve the Eigen-system and construct a 3D band diagram for a given waveguide geometry and mode number m then the dispersion curves show the exact solution of the wave-vectors which correspond to propagating modes, as a function of free space wavelength. (In contrast to a simple waveguide structure, there may be several permitted modes at any given wavelength in a periodic structure. These are known as guided Bloch modes.)

Since the dispersion curves indicate the magnitude and direction of the permitted wave-propagation vectors within the structure at a given wavelength, we have all the information we require in order to calculate an exact value of effective index for each and every guided Bloch mode. Furthermore, if the true effective index for all the Bloch modes at a chosen wavelength is known, then the reflection coefficient and mode overlap at the interface between the input waveguide and PBG region may be calculated.

In the calculation of the effective mode index, the free space wave propagation vector and the wave propagation vector in the PBG lattice region are related by the vector equation:

$$k = k_x + k_y + k_z = k_0 n_{mode} \qquad \text{eqn. 18}$$

$k_0$ is the free space wave propagation constant.

$n_{mode}$ is the effective mode index for the PBG region as seen by the propagating waves.

Taking the gradient:

$$\frac{dk}{dk_0} = \frac{dk_x}{dk_0} + \frac{dk_y}{dk_0} + \frac{dk_z}{dk_0} = n_{mode} \qquad \text{eqn. 19}$$

Now consider a conventional 2-dimensional photonic band diagram. (FIG. 21) This is constructed by repeatedly solving an Eigenvalue problem for a sample set of 'in plane' wave propagation vectors ($k_{xy}$).

Sample k-vectors are related to the direction of wave propagation within the structure (in relation to planes of symmetry in the lattice structure), as well as the wavelength of the propagating wave within the host structure. The choice of sample k-vectors is completely arbitrary, although, by convention, we take k-vectors around the reduced Brillouin zone segment which encompasses all the points of symmetry. Noting that $$\frac{A}{\lambda} = \frac{k_0}{2\pi}$$

the solutions plotted along the y-axis are directly related to the permitted free-space wave vectors ($k_0$) of the propagating modes. Writing the effective mode index $$n_{mode} = |k| \frac{\lambda A}{2\pi A}$$

explicitly in terms of $A/\lambda$.

By evaluating the magnitude of each sample k-vector and dividing it by the free-space k-vector solutions indicated by the dispersion curves we can evaluate the effective mode index corresponding to each and every sample point on each and every dispersion curve.

Modes which have an effective index less than the refractive index of the cladding layer will be lost to the surrounding medium. These are known as radiation modes. Modes with an effective index less than that of the substrate buffer layer will leak into the substrate where they will again be lost. These are known as substrate modes.

The group velocity ($v_g$) of a guided mode within a PBG structure can be calculated with knowledge of the effective mode index and free space wavelength (λ) using the equation $$v_G = \frac{c}{\left(n_{mode} - \lambda \frac{d n_{mode}}{d \lambda}\right)}$$

c = speed of light in vacuo

The group velocity is dependent on the gradient of effective mode index with respect to wavelength. This can be calculated by evaluating the effective mode index associated with each and every k-vector sample point on each dispersion curve in turn. Using these data in conjunction with the wavelength indicated by the associated dispersion curve, we can construct curves showing effective mode index as a function of the guided mode wavelength. The required gradient is then given directly by the gradient of these curves about a particular sample point of interest. Alternatively:

$$v_G = \frac{\partial \omega}{\partial k}$$

where $$\omega = \frac{2\pi c}{\lambda}$$

This shows that the group velocity of the propagating wave is directly related to the gradient of the dispersion curves (plotted on the band diagram). Each sample point on a dispersion curve has a particular group velocity associated with it. We can therefore choose the speed of the propagating modes transmitted within the PBG structure, by controlling the mode coupling between the input waveguide and the PBG region.

For example, if the boundary between the input waveguide and PBG structure is designed correctly, light travelling in the input waveguide will couple into a guided Bloch mode with a k-vector positioned at a point of inflection on the dispersion curve. In this case the propagating waves will have zero group velocity, and standing waves will form inside the structure. If we couple into Bloch modes slightly away from the point of inflection on the dispersion curve, then the wave will propagate through the structure with a very small group velocity. Finally, if we couple into a guided Bloch mode whose k-vector lies at the point where the gradient of the dispersion curve is steepest, then the propagating wave will travel at maximum speed. In this way we can use a PBG structure to 'slow down' or trap light.

Alternatively, by changing the direction of the propagating waves within the PBG structure, we can alter both the speed of propagation, and the wavelength of the waves propagating within the structure. This may form the basis of an optical delay line.

The wavelength of the propagating waves within the PBG waveguide structure can be calculated with knowledge of the effective mode index and free space mode wavelength (indicated by the dispersion curves) using the relationship:

$$\lambda_{PBG} = \frac{\lambda_0}{n_{mode}}$$

alternatively it can be found from the magnitude of the wave-propagation vector within the PBG material:

$$\lambda_{PBG} = \frac{|k|}{2\pi}$$

Under certain conditions, consecutive rows of pores will be seen by the propagating waves to constitute strongly diffracting planes. Diffraction effects give rise to the multiple beam splitting which is utilised in the cross-port multiplexer.

With knowledge of the wavelength of the propagating wave within the structure, we can determine whether or not diffraction (such as first or second order multiple beam splitting) will be observed by applying the Bragg diffraction condition:

$$m\lambda_{PBG} = 2\Lambda \sin(\phi_d - \phi_i)$$

m is an integer number indicating the order of diffraction.

$P_u$ is the spacing between consecutive diffracting planes.

$\phi_d$ is the angle of diffraction, measured with respect to the normal to the diffracting planes.

$\phi_i$ is the angle of incidence, measured with respect to the normal to the diffracting planes.

In a conventional (1-dimensional) diffraction grating, the diffraction order, m gives us a direct measure of the number of diffracted beams. For example if m=0 (zero order diffraction) there will be a single beam. However, in a two dimensional lattice structure, there may be a set of beams for each diffraction order corresponding to the number of symmetry planes of the lattice. For example a triangular lattice with 6-fold symmetry, may give rise to a set of 6 beams for each diffraction order.

The direction of the diffracted beams may be calculated using the Bragg condition, with knowledge of the wavelength in the material. It should be noted that diffracted beams may couple into other Bloch modes within the lattice, with different effective indexes.

For the solution of guided Bloch modes and the corresponding effective indexes in a metallised waveguide containing a PBG, the first objective is to construct an accurate two dimensional band diagram which shows the wavelength of guided Bloch modes as a function of 'in plane' wave vector ($k_{xy}$), for a particular waveguide mode and polarisation state.

For a metallised waveguide (such as a microwave conduit) the transverse phase matching condition is given by:

$$k_z = \frac{m\pi}{d} \qquad \text{eqn. 22}$$

m is the mode number, d is the waveguide thickness.

This is a simple function independent of $k_{xy}$, and $k_0$. Consequently we can construct the required band diagram using a single value of $k_z$ for all in-plane k-vector sample points.

The guided mode solutions at a particular wavelength of interest are then indicated by the points of intersection between a horizontal wavelength line and the dispersion curves. Examples are indicated at 545 nm and 633 nm on the band diagram of guided modes in a silicon nitride PBG waveguide (FIG. 22). There may be several guided Bloch modes (corresponding to the number of dispersion curves intersected on that wavelength) for any wavelength or polarisation state.

To evaluate the effective index of the guided modes, more information than is shown on the band diagram is required.

Having found the 'in plane' wave-vectors which correspond to the points of intersection, the band structure calculation must be repeated using a slightly different value of $k_z$. In effect this forms a very small section of a three-dimensional dispersion surface. The gradient of the dispersion surface then gives the effective mode index.

For the solution of guided Bloch modes and the effective mode index in a dielectric waveguide containing a PBG, the transverse phase matching condition contains a polarisation dependent phase term. This reflects the fact that there is an evanescent wave penetrating a short distance into the substrate buffer and cladding layers:

$$k_z = \frac{(m\pi - \phi)}{d} \qquad \text{eqn. 23}$$

$\phi$ is the sum of the phase changes upon reflection from the two waveguide boundaries.

m is the mode number d is the core thickness

The phase term $\phi$ can be arranged in terms of the wave-propagation vector components $k_{xy}$ and $k_z$.

$$\phi_{TM} = \tan^{-1}\left(\text{real}\left(\sqrt{\frac{\left(k_{xy}^2 - \left(\frac{n_{clad/buff}|k|}{n_{mode}}\right)^2\right)}{k_z}}\right)\right) \qquad \text{eqn. 24}$$

$$\phi_n = \tan^{-1}\left(\text{real}\left(\sqrt{\frac{\left(k_{xy}^2 - \left(\frac{n_{clad/buff}|k|}{n_{mode}}\right)^2\left(\frac{n_{mode}}{n_{clad/buff}}\right)^2\right)}{k_z}}\right)\right) \qquad \text{eqn. 25}$$

$n_{clad/buff}$ is the refractive index of either the buffer layer of cladding layer as appropriate.

Each propagating wave-vector (Bloch wave-vector) must be three dimensional (e.g. $k=k_x+k_y+k_z$) dimensional if the PBG device has finite thickness. In certain special cases (such as was the case for the metallised waveguide) the solutions all have the same value of $k_z$ irrespective of wavelength. When plotting a conventional band diagram, the $k_x$ and $k_y$ vector components may be compressed on to one graph axis by choosing a well defined 'in plane' k-vector circuit between symmetric points of the Brillouin zone. This generates a single, more general, combined wave-vector $k_{xy}$. which can be plotted along one axis.

To perform a three-dimensional analysis, it is more appropriate to regard the dispersion relations as a 3-dimensional surface, rather than a two dimensional curve. The $k_z$-dependence is then preserved by mapping it on to the new axis. The $k_x$ and $k_y$ wave-vector components may be compressed onto a single axis ($k_{xy}$) as before.

In order to find the required set of values of $k_z$, we must first evaluate the eigenvalue problem over a two dimensional grid of sample values for $k_{xy}$ and $k_z$. This effectively constructs a set of three dimensional dispersion surfaces as opposed to the two-dimensional dispersion curves normally plotted on a conventional band diagram. Since the maximum deviation which can be incurred by the phase term is $-\pi$, it is sensible to sample $k_z$ over the range:

$$k_z = \frac{(m-1)\pi}{d} \to \frac{m\pi}{d}$$

Each sample point on each dispersion surface has a particular effective mode index, and mode number (m) associated with it. Re-arranging the transverse phase condition the mode number can be calculated using:

m=($k_z$d+$\phi$)/$\pi$

This effectively constructs a set of three dimensional mode number surfaces each related to a particular dispersion surface. Exact values of $k_z$ corresponding to an integer mode number are then found for each $k_{xy}$ sample point in turn by interpolating the mode surface data using polynomial expansions.

Once exact values of $k_z$ have been found, the exact effective mode index corresponding to each $k_{xy}$ sample point can then be found by interpolating the effective mode index data to the same value of $k_z$ in a similar way.

Depending on the resolution of the initial sample grid, and the order of the polynomial expansions, we can obtain extremely accurate solutions for the guided Bloch modes and the corresponding effective mode indexes.

Although guided modes may be supported by the PBG structure, it may not necessarily be possible to couple light from the input waveguide directly into them. There will be a certain degree of loss at the boundary between the input waveguide and PBG structure due to mode mismatch between the two regions. There will also be a back reflection due to the change in effective mode index at the boundary. The back reflection and transmission coefficient can be calculated using the Fresnel equations which in this case can be expressed:

$$R_{TM} = \frac{n_{core}\sin(\theta_{wg}) - n_{mode}\sin(\theta_{PBG})}{n_{core}\sin(\theta_{wg}) + n_{mode}\sin(\theta_{PBG})}$$

$$T_{TM} = \frac{2n_{mode}\sin(\theta_{PBG})}{n_{core}\sin(\theta_{wg}) + n_{mode}\sin(\theta_{PBG})}$$

$$R_{TE} = \frac{n_{core}\sin(\theta_{PBG}) - n_{mode}\sin(\theta_{wg})}{n_{core}\sin(\theta_{PBG}) + n_{mode}\sin(\theta_{wg})}$$

$$T_{TM} = \frac{2n_{mode}\sin(\theta_{wg})}{n_{core}\sin(\theta_{PBG}) + n_{mode}\sin(\theta_{wg})}$$

$\theta_{wg}$=waveguide mode angle (measured with respect to normal to waveguide boundaries.)

$\theta_{PBG}$=Bloch mode angle in PBG region (measured with respect to normal to waveguide boundaries the guided Bloch mode angle in the PBG structure is given by:

$$\sin(\theta_{PBG}) = \frac{k_z}{|k|}$$

The input waveguide mode angle $\phi_{wg}$ can be found by applying the transverse phase matching condition to the input waveguide, and solving as a function of mode number, wavelength and polarisation state. This can be expressed as:

m$\pi$=($k_z$d−$\phi_{clad}$−$\phi_{buff}$)

d=thickness of waveguide core, m=mode number substituting for $k_z$, and re-arranging as a function of wavelength, the phase condition can be written:

$$\lambda_{mode}(\theta_{wg}) = Re\left[\frac{2\cos(\theta_{wg})n_{core}d}{\phi_{buffer} + \phi_{clad} + m}\right]$$

where the phase terms $\phi_{buff}$ and $\phi_{clad}$ are given by:

$$\phi_{TE} = \tan^{-1}\left[Re\left(\sqrt{\frac{\sin(\theta_{wg})^2 - \left(\frac{n_{clad/buff}}{n_{core}}\right)^2}{\cos(\theta_{wg})^2}}\right)\right]$$

$$\phi_{TM} = \tan^{-1}\left[Re\left(\sqrt{\frac{\sin(\theta_{wg})^2 - \left(\frac{n_{clad/buff}}{n_{core}}\right)^2}{\cos(\theta_{wg})^2}}\left(\frac{n_{core}}{n_{clad/buff}}\right)^2\right)\right]$$

for the appropriate polarisation state, using the appropriate value for $n_{clad/buff}$. The following is a summary of the computational method.

1) The best practical approach to the computational problem is to create a 3-dimensional surface map containing the plane wave solutions for a range of values of $k_z$ close to that required to satisfy the basic boundary conditions, for the selected waveguide mode. There will be one dispersion surface map for each dispersion band.

2) By evaluating the magnitude of the sample k-vectors and the free space k-vector $k_0$ given by the eigenvalue solution, and dividing one by the other, the effective mode index can be found.

3) Using the relevant values of effective mode index for each dispersion surface, calculated by step 2, we can generate a map of mode number as a function of $k_{xy}$ and $k_z$ by solving the transverse phase matching condition at each sample point. There will be a separate mode index map for each polarisation state.

4) The relevant mode number map for each dispersion surface is then scanned, taking each $k_{xy}$ sample in turn, looking for mode values closest to the chosen modenumber. This will return the two closest values of $k_z$ each side of the chosen mode number. A polynomial expansion describing the curve over a range of sample points either side of known solution point is then constructed. The precise value of $k_z$ for the integer mode number is then found, by solving the polynomial. In this way, a precise list of new values of $k_z$ corresponding to each 'in plane' k-vector sample point ($k_{xy}$) is constructed. There will be one list for each dispersion band.

5a) There are now two choices. For a slightly less accurate result, we can go back to the dispersion surfaces (calculated in step 1) and extrapolate the wavelength solutions to the point addressed by $k_z$ for each in-plane k-vector sample point and dispersion curve in turn.

5b) Alternatively, (and more accurately), the photonic band structure may be recalculated using the precise new values of $k_z$, calculated for each 'in plane' k-vector sample point and dispersion curve. This will be quite a lengthy process since the entire band structure must be re-calculated twice for each dispersion curve of interest.

6) Using the final wavelength values, a conventional two-dimensional photonic band diagram may be plotted. This shows the exact wavelength of guided Bloch modes corresponding to the chosen waveguide mode, and the chosen 'in plane' sample wave-vectors $k_{xy}$. The precise position of band gaps can then be read from this diagram, as can the exact in-plane Bloch mode solution at a particular wavelength of interest 7) A final effective mode index table corresponding to all the sample points on the new corrected dispersion curves is calculated by extrapolating the effective mode index functions to the precise value of $k_z$, calculated for each 'in plane' k-vector sample point and dispersion curve.

8) The mode guided mode wavelength in the input waveguide is evaluated as a function of mode angle, 9) The reflection and transmission coefficient at the boundary between the input waveguide and PBG region, is calculated using the effective mode index table and guided Bloch mode angle.

10) The mode profile in the input waveguide and PBG waveguide region is calculated, followed by the mode overlap between the two regions.

Figure 50:
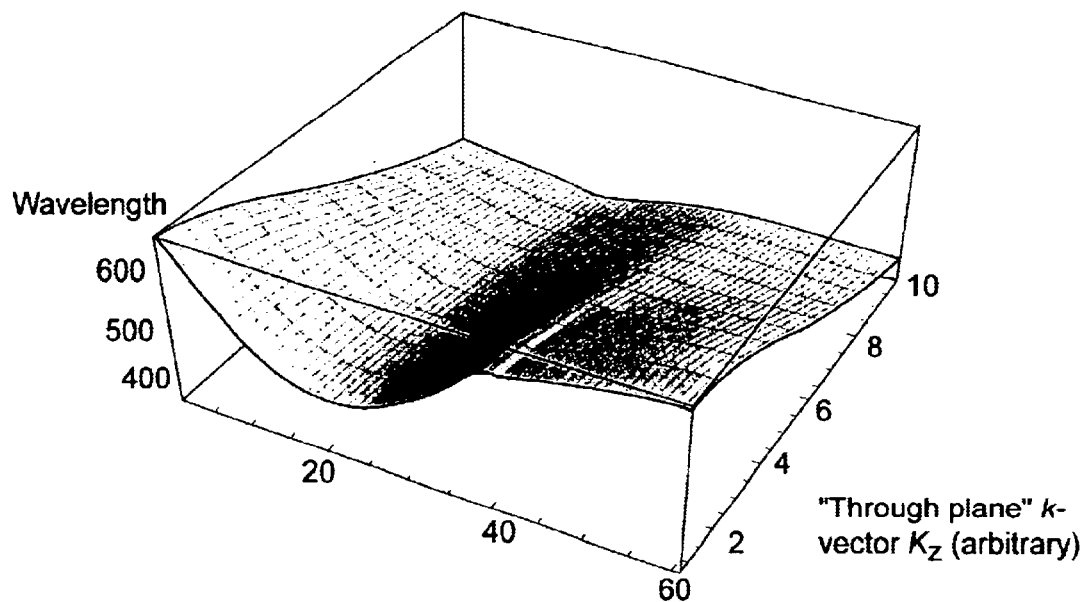
Figure 51:
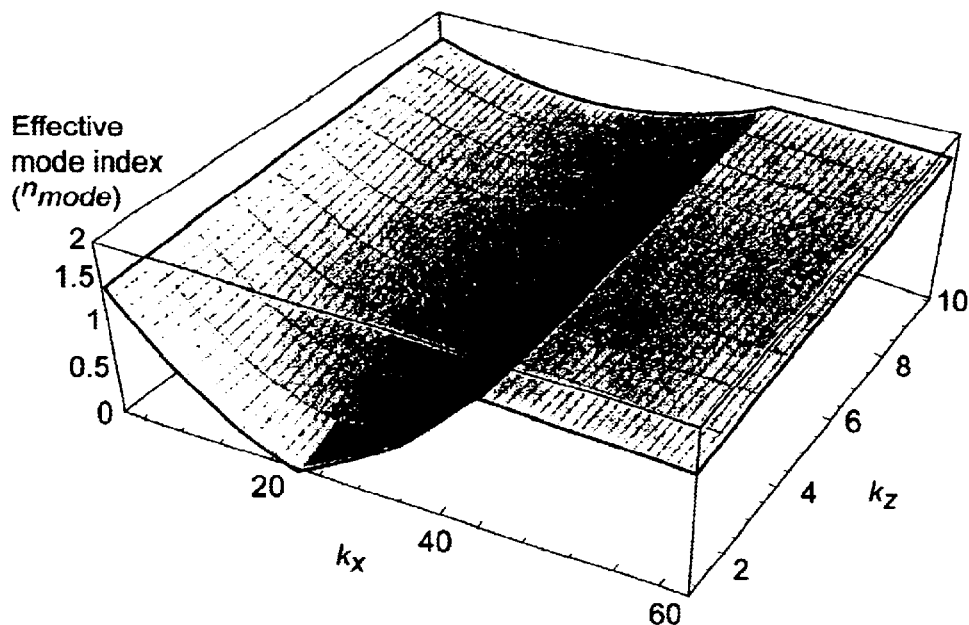
Figure 52A:
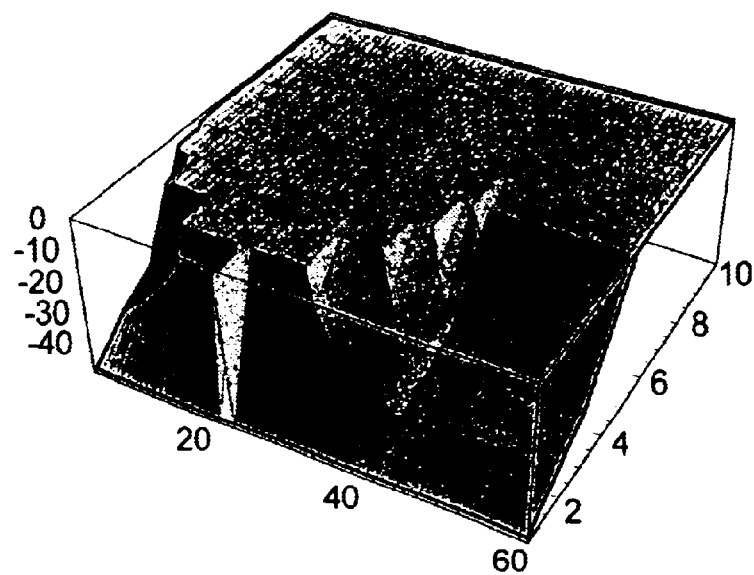
Figure 52B:
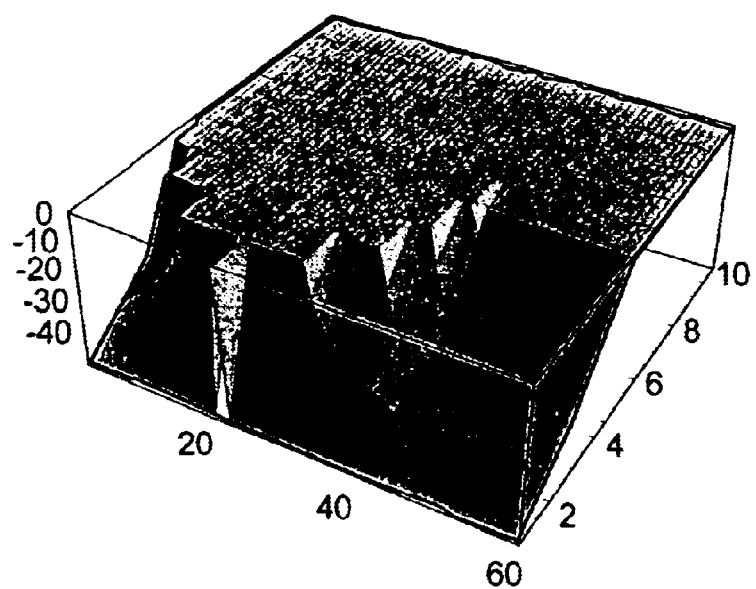
Figure 53A:
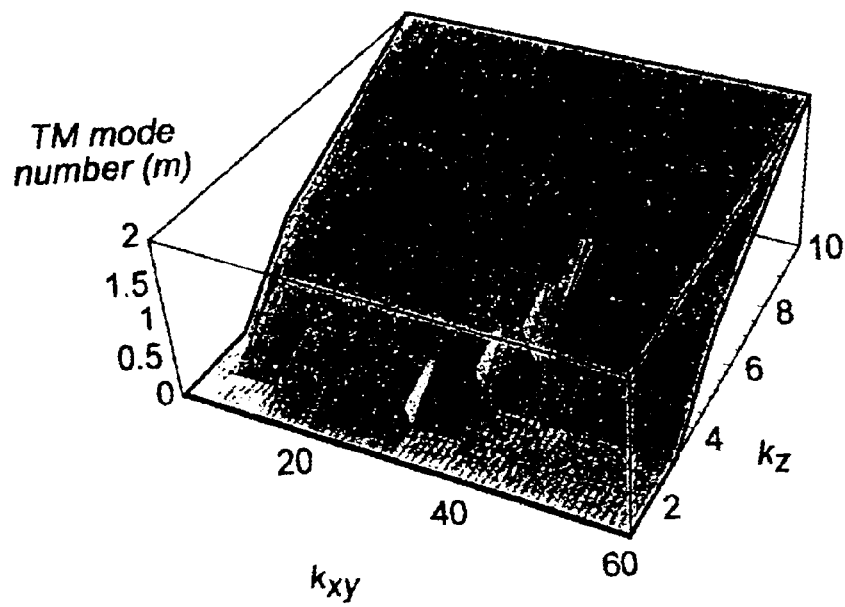
Figure 53B:
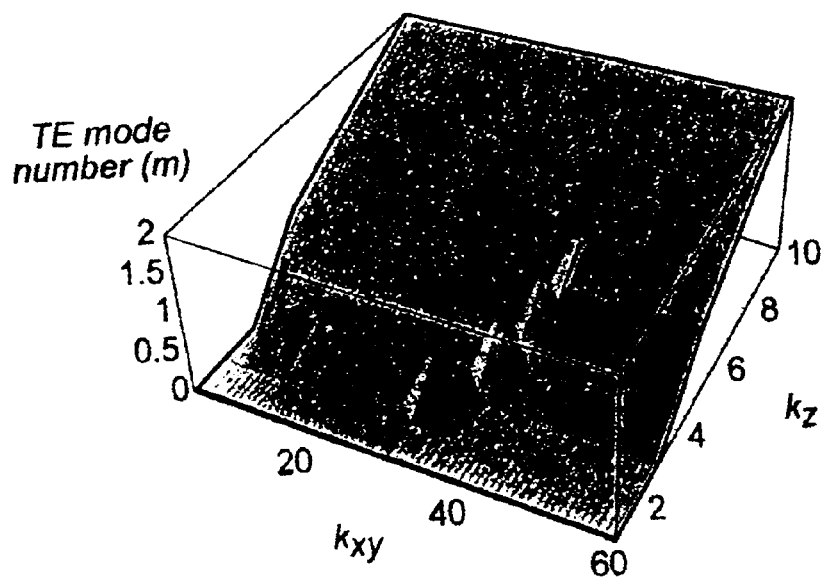
Figure 54:
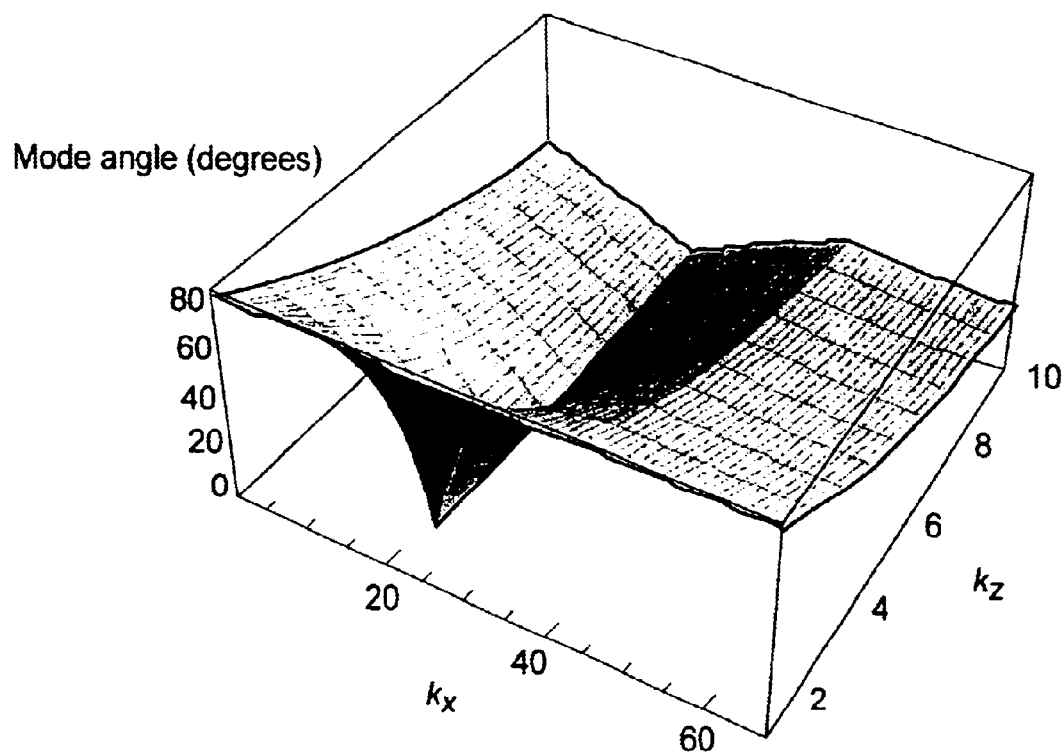
Figure 55:
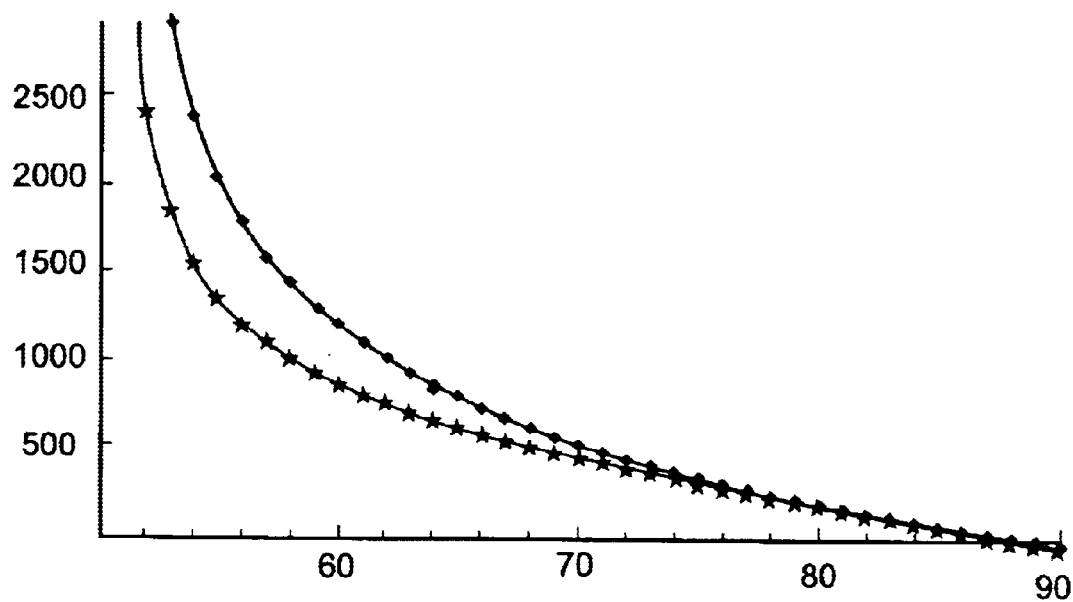
Figure 56:
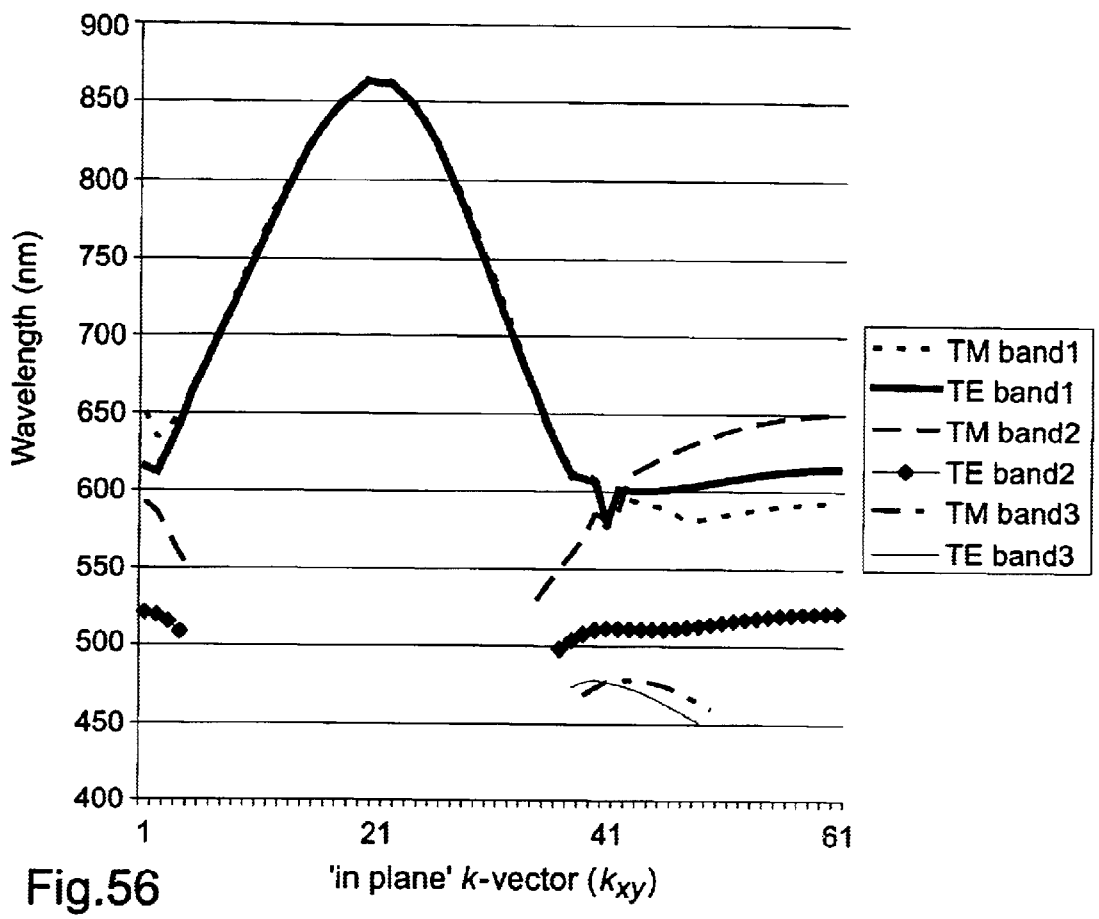
Figure 57:
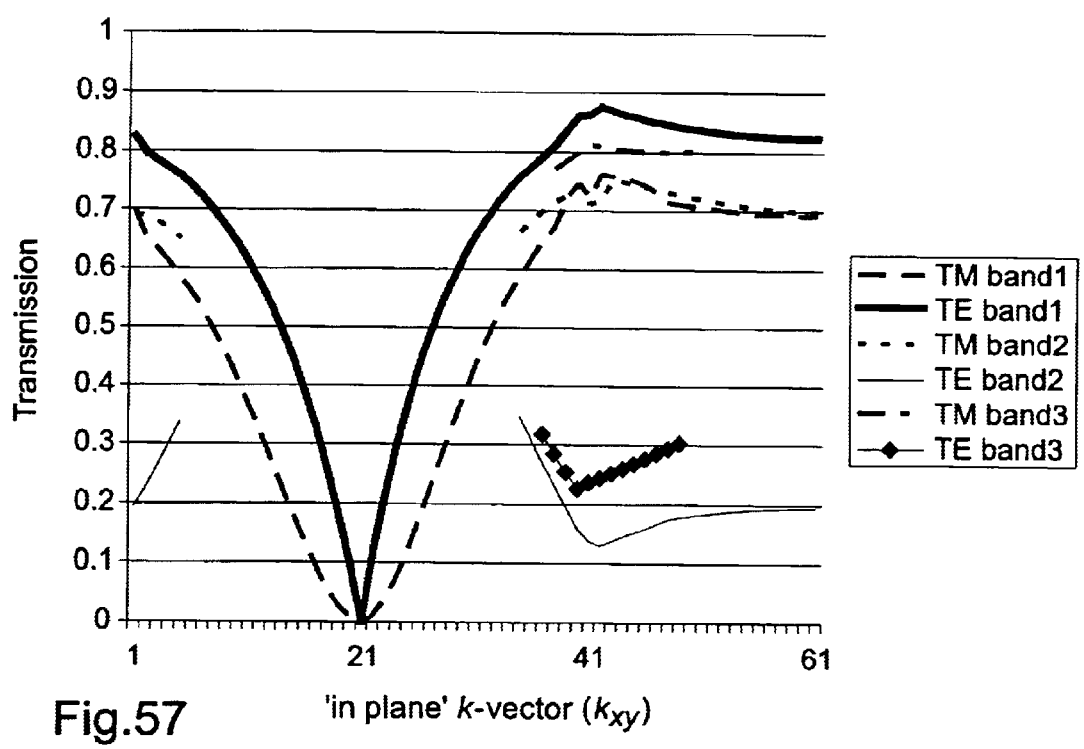

A simulation was carried out for a waveguide structure consisting of a thick silicon dioxide buffer layer, a 250 nm silicon nitride core and a thick silicon cladding layer. The band structure was calculated using the plane wave method, evaluating the eigensystem over a grid of 25 lattice points. FIG. 50 is a three-dimensional surface plot corresponding to the fourth dispersion band. The range of $k_z$ sample vectors were chosen to correspond to the mode number range 0→2 (e.g. 0=mode 0, 5=mode 1). FIG. 51 is a three-dimensional effective mode index surface corresponding to the fourth dispersion surface. Note that effective mode index values range between $n_{core}$ and 0. Modes with values less than $n_{clad}$ or $n_{buff}$ correspond to lossy radiation modes or substrate modes in the PBG structure. FIG. 52*a* is a TM phase angle map and FIG. 52*b* is a TE phase angle map corresponding to the first dispersion surface. FIG. 53*a* and *b* are TM and TE mode number maps. FIG. 54 is the mode angle associated with each k-vector sample point. (same for all dispersion surfaces). FIG. 55 is the wavelength of guided mode in input waveguide section as function of mode angle. The dotted line represents TM modes and the solid line, TE modes. FIG. 56 is the band diagram for waveguide mode 1 and FIG. 57 is the corresponding transmission coefficient.

Fabrication of a face plate, in accordance with a specific embodiment of the invention, will now be described in detail, by way of example of a process for producing deep holes.

Referring to FIG. 23 of the drawings, a substrate 10 comprises 3–5 Ω-cm n-type <100>orientation silicon wafer. Holes are formed in the substrate 10. A thin oxide layer 12 is grown by oxidising the wafer to substrate 10 in a dry oxygen environment. The surface of the layer 12 is coated in photoresist 14. The photoresist layer 14 is patterned with a regular lattice pattern using direct write e-beam lithography a technique well known by those skilled in the art and which is described by Lehrmann in the above referenced paper cited in the preamble. The photoresist layer 14 is developed and hard baked in an oven (not shown) leaving circular windows 16 at lattice sites on the surface. The surface of the silicon is exposed as silicon dioxide 18 is then removed by plasma etching and the photoresist stripped to leave a fully patterned silicon dioxide mask. Pyramidal notches 20 are created in the exposed silicon windows by a potassium hydroxide (KOH) etch. A weak solution of hydrofluoric acid (HF) in ethanol is then used as an electrolyte for the anodisation process. The ethanol acts as a wetting agent.

Examples of deep macro pores formed by the anodisation process are illustrated in FIG. 23. For sake of clarity, this shows a relatively large scale structure, however arrays of holes can be grown to depths of over 150 μm while maintaining a uniform diameter of the order of 200 nm.

After anodisation the holes may be enlarged by repeated oxidation and oxide stripping to form micro-structures suitable for photonic band structure applications.

If the macro pore structures are repeatedly oxidised, the holes will eventually break through to their neighbours, leaving free standing silicon pillars at the corner sites between holes. The diameter of the pillars can be reduced by further oxidation to form arrays of free-standing quantum wires. Using this process, diameters as small as 150 nm have so far been achieved.

Due to the extremely small lattice dimensions and the comparatively huge depth of air hole needed to create an optical band gap, it has, hitherto, proved extremely difficult to fabricate photonic band structures in the near or mid infra-red (NIR/MIR) region of the spectrum. In one embodiment of the present invention, a photo-assisted anodic etching process is applied to the fabrication of a two dimensional mid-infra-red photonic crystal based on a 0.81 µm triangular lattice of air rods in silicon. The 'through plane' transmission characteristics of a device grown to a depth of 40 µm with an estimated air filling fraction of 45% has been tested over a wide spectral range and for various angles of wave propagation using a specially modified Perkin-Elmer Fourier Transform Infra-Red (FTIR) spectrometer for the measurements.

The PBG sample was mounted on a rotating stage and light from the FTIR spectrometer focused on to the surface at the axis of rotation using a mirror and a reflecting microscope objective. Part of the transmitted light was then collected by an $As_2S_3$ fibre which couples the light back into the spectrometer. The fibre had an unusually large core diameter of 150 µm. The light emerging from the other fibre end was then reflected from a parabolic mirror and focused on to a Cadmium Mercury Telluride (CMT) detector within the FTIR spectrometer.

The 'through plane' transmission characteristics were measured over a wide spectral range for various external angles of incidence with respect to the plane of the structure. Spectral measurements were made with reference to a blank silicon spectra taken at each angle of measurement which removed the effect of absorption bands in the fibre link, and silicon substrate. For this particular sample, the photonic band gap was found to be closed at normal incidence so this spectrum may be used as a reference for measuring the level of attenuation. (FIG. 7). It should be noted that the large external angular probing range of 60° corresponds to an internal angular range of 14° due to refraction at the interface and accounting for the reduced refractive index of the device. Absorption bands within the fibre link appear as noise spikes on the spectra, the strongest of which appears at 2500 cm.

The PBG structure caused a strong attenuation in the range 1500 to approximately 4800 $cm^{-1}$ (2 µm to 6.7 µm) and that the level of attenuation increased almost linearly as the angle of incidence moves away from the normal to the plane of the lattice.

Comparing the spectra with the theoretically predicted 'in plane' band diagram (calculated following the plane wave method of Plihal et al ([M. Plihal, A. A. Maradudin, *Physical Review B*, 44, 8565, (1991)] using 255 plane waves), gives good agreement between the two. However, the detected band gap extends to a much lower wave number than that predicted by the band diagram. As the present optical arrangement actually launches uncollimated light into the device exciting all the wave propagation modes within the plane of the lattice simultaneously, in effect, the average band gap is measured for all angles of wave propagation within the plane of the lattice. This therefore compares the detected band edges with the average wave-number of the lower two bands. The 'average' band gap extends from 1752 $cm^{-1}$ to 4760 $cm^{-1}$. The detected band gap extends from 1500–4800 $cm^{-1}$. Bearing in mind the ambiguity of the lower band edge due to spectral noise, there is extremely good agreement between the detected and predicted band edges.

Conventionally, microchannel plates are fabricated by stacking bundles of glass capillary tubes together, then drawing them out to reduce the pitch of the resultant lattice to a few micrometres. The tubes are then coated with a photo-emissive material. The fabrication process is extremely labour intensive and the maximum resolution (determined by the final lattice pitch) is limited by technological difficulty in drawing the fibre bundle out without causing collapse of the capillary tubes or introducing extra stacking faults. These problems also limit the maximum diameter of the microchannel plate. Dimensions of these existing plates are typically limited to ~7 mm lattice pitch, and overall diameter ~2 cm.

Microchannel plates may advantageously be fabricated using a modification of the process outlined with respect to FIG. 23. An image intensifier including such a plate is depicted diagrammatically in FIG. 24. This includes a lens I positioned to project radiation from an object O on to one surface S1 of a microchannel plate MP produced by the above method. A potential difference is applied with respect to the other surface S2 causing electrons to impinge on a phosphorescent screen S. Devices according to this particular aspect of the invention offer significantly improved resolution (lattice pitches down to 500 nm or less have been made), are cheap and easy to fabricate, and can have any overall diameter which is of the order of tens of centimetres and is only limited by the diameter of wafers used to produce the semiconductor substrate.

In accordance with a particular embodiment of the invention, a microchannel plate is constructed using an initial substrate consisting of an n-doped low resistivity (3–5 Ω-cm) <100> silicon wafer. The substrate is oxidised creating a 200 nm thick silicon-dioxide masking layer. (Alternatively a silicon nitride masking layer may be deposited by LPCVD). Resist is spun on to the masking layer and exposed by direct-write electron beam lithography to create a desired lattice pattern. The resist is developed and hard-baked creating circular windows at the lattice sites. The windows may be of an arbitrary size, provided they are smaller than the final required pore diameter. The wafer is then dry-etched and the resist stripped to leave a fully patterned oxide (or nitride) masking layer. A KOH etch creates pyramidal notches at the sites of the unprotected oxide windows.

Ohmic contact is then made to the rear of the wafer using gallium-indium eutectic, in preparation for an anodic etching process. The pores are then grown to a required depth (or indeed right through the wafer) by anodic etching. The devices are oxidised in a dry oxygen environment and the oxide is stripped in hydrofluoric acid, increasing the diameter of the pores. These stages are repeated to obtain the desired pore diameter. The final oxidised layer is not removed, thus leaving a highly insulating coating.

The wafer may be etched through from the rear surface using potassium hydroxide to cause the pores to break through to the rear surface, after which the wafer is oxidised again to form an insulating layer on the rear surface. The device is coated with a photo-emissive material and electrical contact made to the front and rear surfaces by evaporating a metal (such as aluminium) through a mask.

Each tube in the micro-channel plate acts as a photo-multiplier. Photons which are directed down the tubes by the lens cause emission of a multitude of electrons in the photo-emissive coating. These electrons then propagate down the tubes towards the phosphorescent screen where they cause visible scintillations on the screen. An enhanced image of the dimly illuminated object appears on the screen.

Several factors affect the properties of a photonic band gap. These include: lattice shape, dielectric contrast, pore radius and wave polarisation state. A triangular lattice provides the widest band gap, and also offers the possibility of creating a full PBG for both TE and TM polarised waves simultaneously. However, in order to create a TM polarised band gap, a large dielectric contrast is required. For this reason, semiconductor materials such as silicon, germanium or gallium arsenide, have hitherto been the natural choice for the fabrication of PBGs. However, these materials become transparent in the Near Infra-Red (NIR). We have fabricated waveguide devices from a relatively low index material (silicon nitride), which is transparent in the visible, but can only support a TE polarised band gap.

One application for PBGs is the control of spontaneous emission in active opto-electronic devices such as LEDs and lasers. For this application, it has been considered desirable to create a three-dimensional PBG which will channel all emissions into a single narrow bandwidth laser mode. Since most micro-cavities, support an equal number of TE and TM polarised modes, both must be suppressed otherwise power will simply be redirected into the unaffected polarisation state, and there will be little improvement in laser efficiency. Polarisation selectivity is, however, of benefit in many passive applications. For example, the capacity of an optical communication system may be doubled by incorporating polarisation selectivity into all the switching components. Polarisation selectivity will also permit an increase in the integration level of an integrated opto-electronic circuit (IOEC). It is also useful as a diagnostic tool. Using TM polarised light as a control, it is possible to attribute unusual optical behaviour such as guided mode suppression to the PBG, rather than more common optical effects such as scattering or diffraction.

Many real applications will also require low loss transmission at wavelengths away from the stop band.

In the embodiment depicted in FIG. 25, several rows of air pores are arranged on a triangular lattice, plasma etched through the oxide cover layer 121 and the silicon nitride core 122 of a waveguide structure formed on a silicon dioxide buffer layer 123 on a silicon substrate 124. The lattice pitch was either 300 nm or 260 nm. Light was end-fire coupled into the waveguide and the transmission properties of the lattice region examined. In the design of the devices, we use a three-dimensional plane-wave analysis in combination with conventional waveguide theory to ensure the existence of guided Bloch modes at wavelengths either side of the band gap.

The waveguide consists of a thermally grown, 1.8 $\mu$m thick silicon dioxide substrate buffer layer (n=1.46), a 250 nm thick silicon nitride core (n=2.02), and a 75 nm thick silicon dioxide cladding layer. The core and cladding layers were both deposited by Low Pressure Chemical Vapour Deposition (LPCVD). The wafers were patterned by direct write electron beam lithography using UVIII resist, which was then plasma etched to create narrow isotropic pores (FIG. 1). Surprisingly, very small pores arranged on a triangular lattice of pitch 260 nm, with diameters in the range 50–120 nm may be created by controlling the lithography alone. However, this is still too small to create a reasonably big photonic band gap. By direct-writing wider pores, surface tension in the resist causes the pattern to be obliterated upon development.

The solution to this problem is initially to etch very narrow pores, then expand them up in the nitride core layer, using a nitride selective etch. This also permits the fine tuning of the photonic band gap after initial fabrication. (FIG. 26).

Unlike a conventional diffraction grating, the dimensions of the pores are below the Rayleigh resolution limit at wavelengths close to the stop band, and so cannot be properly resolved by the propagating waves. Consequently, an average index approach can be used to give a good approximation of the general waveguide characteristics. In a conventional waveguide, light is confined within a high index dielectric region surrounded by a low index dielectric cladding by total internal reflection. To permit transmission across a PBG device at wavelengths outside the bandgap, the effective index of the core must remain greater than that of the cladding and buffer layers. This limits the radius of the pores which, in turn, limits the air filling fraction (f) and the bandwidth of the PBG. One solution is to etch the holes deep into the substrate buffer layer. This reduces the effective index of all the waveguide layers in the same ratio, maintaining a well confined mode for large pore diameters. This structure is fabricated by selectively expanding a narrow capillary tube part etched into the oxide buffer layer. With careful control, a very porous silicon dioxide honeycomb which provides good supports for the PBG lattice (SEM FIG. 17) can be created.

Alternatively, the waveguide core may be completely undercut to form an air cavity below the lattice region. This creates a completely isolated bridge waveguide structure which supports a guided mode even for close packed pores (SEM3 FIG. 27). This device has the major advantage that there are identical mediums on both sides of the PBG lattice. However, bridge waveguide structures can be extremely fragile for more than a few lattice periods. We have successfully created devices with over 20 lattice periods and an air filling fraction of 60%.

Figure 28:
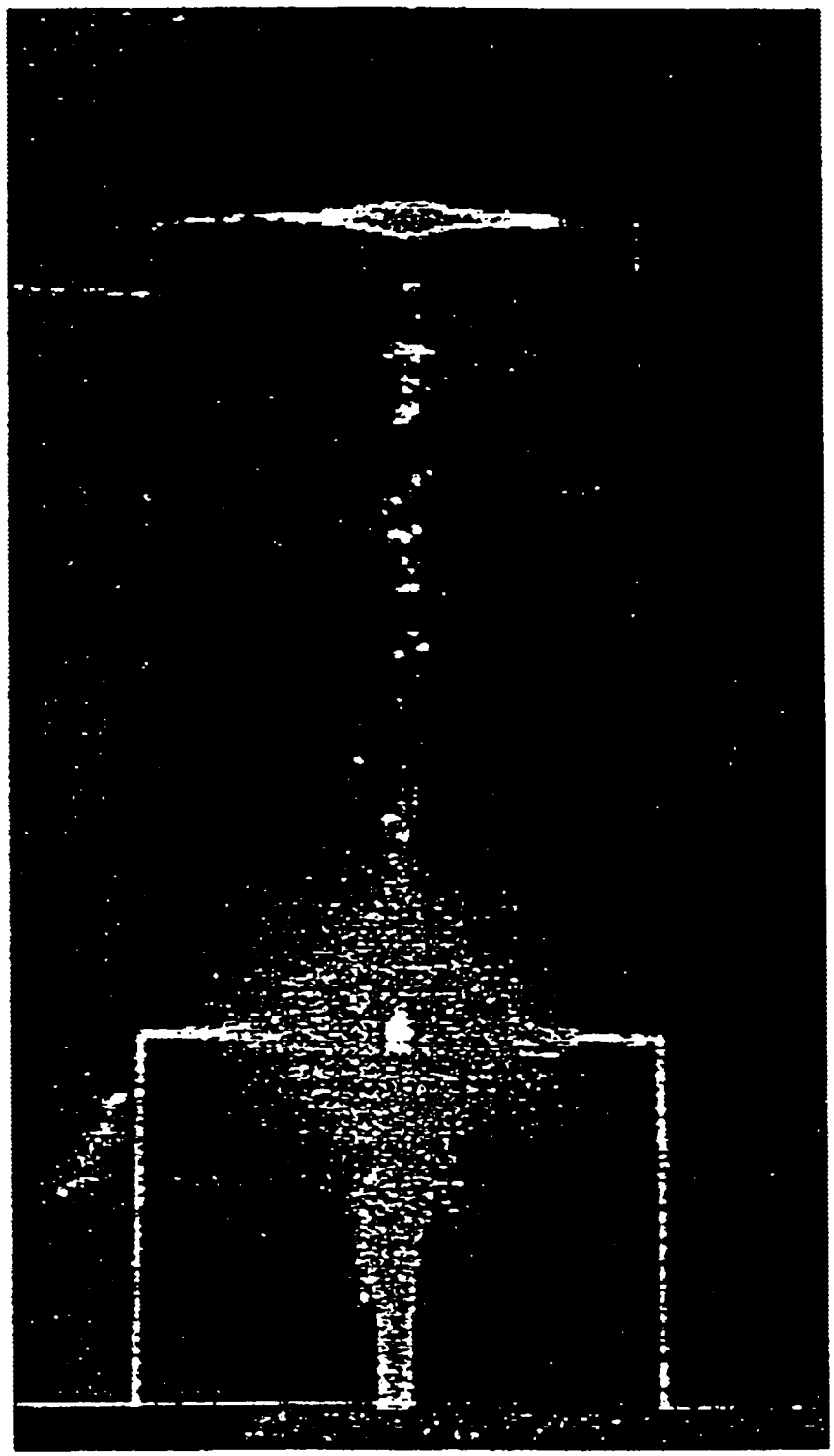

A device consisting of 2730 rows of air pores (radius 200 nm), with an air filling fraction of 40%, arranged on a triangular lattice (pitch 300 nm), written as a strip across a monomode silicon nitride waveguide (core thickness 250 nm), demonstrates the existence of a polarisation dependent band gap in the visible region of the spectrum. Photograph FIG. 28 shows this device directly from above. Red light from a He—Ne laser (632.8 nm) is end fire coupled into the device, and is incident perpendicular to the PBG strip (left to right of photo) propagating along the T-J lattice symmetry direction.

Figure 29:
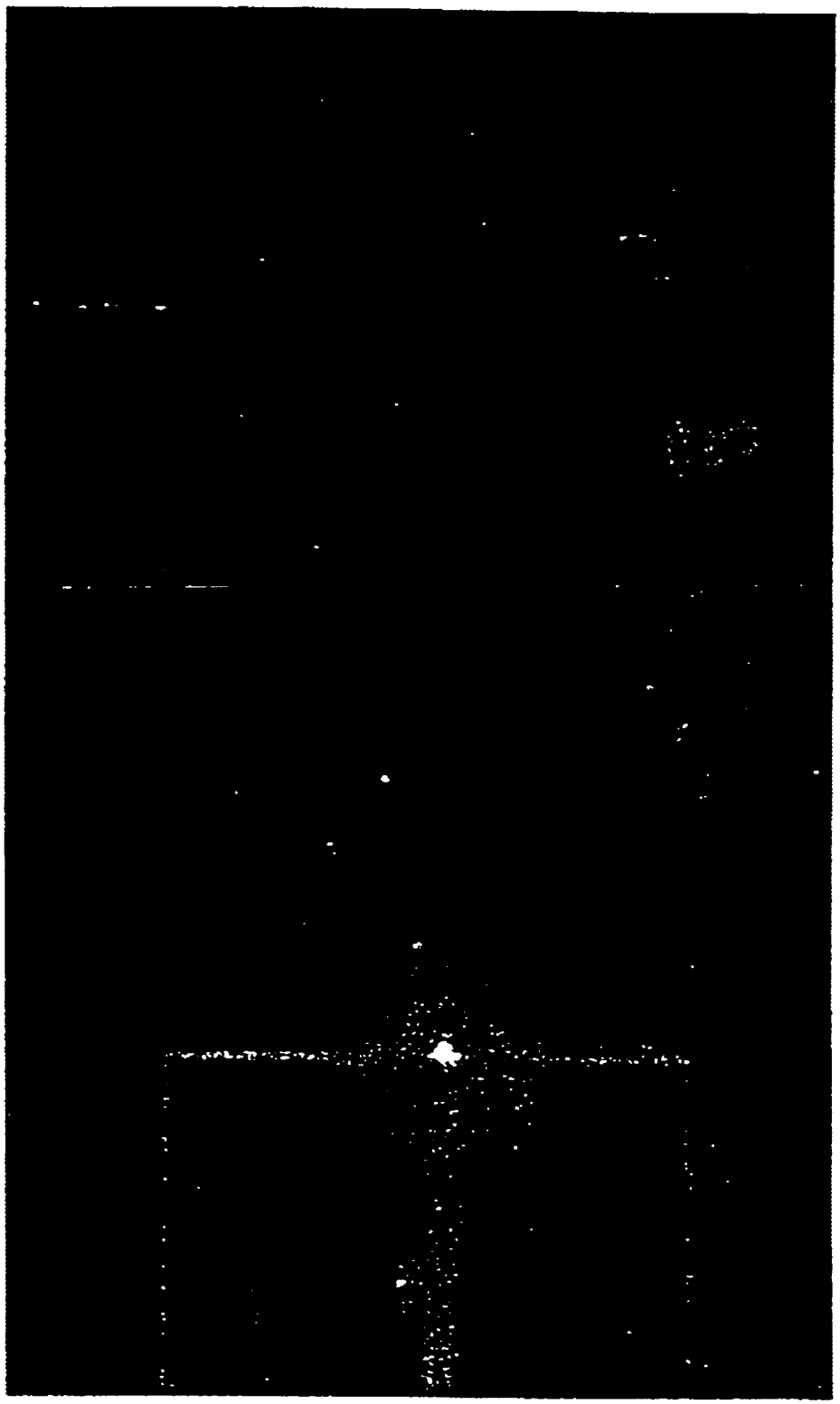
Figure 30:
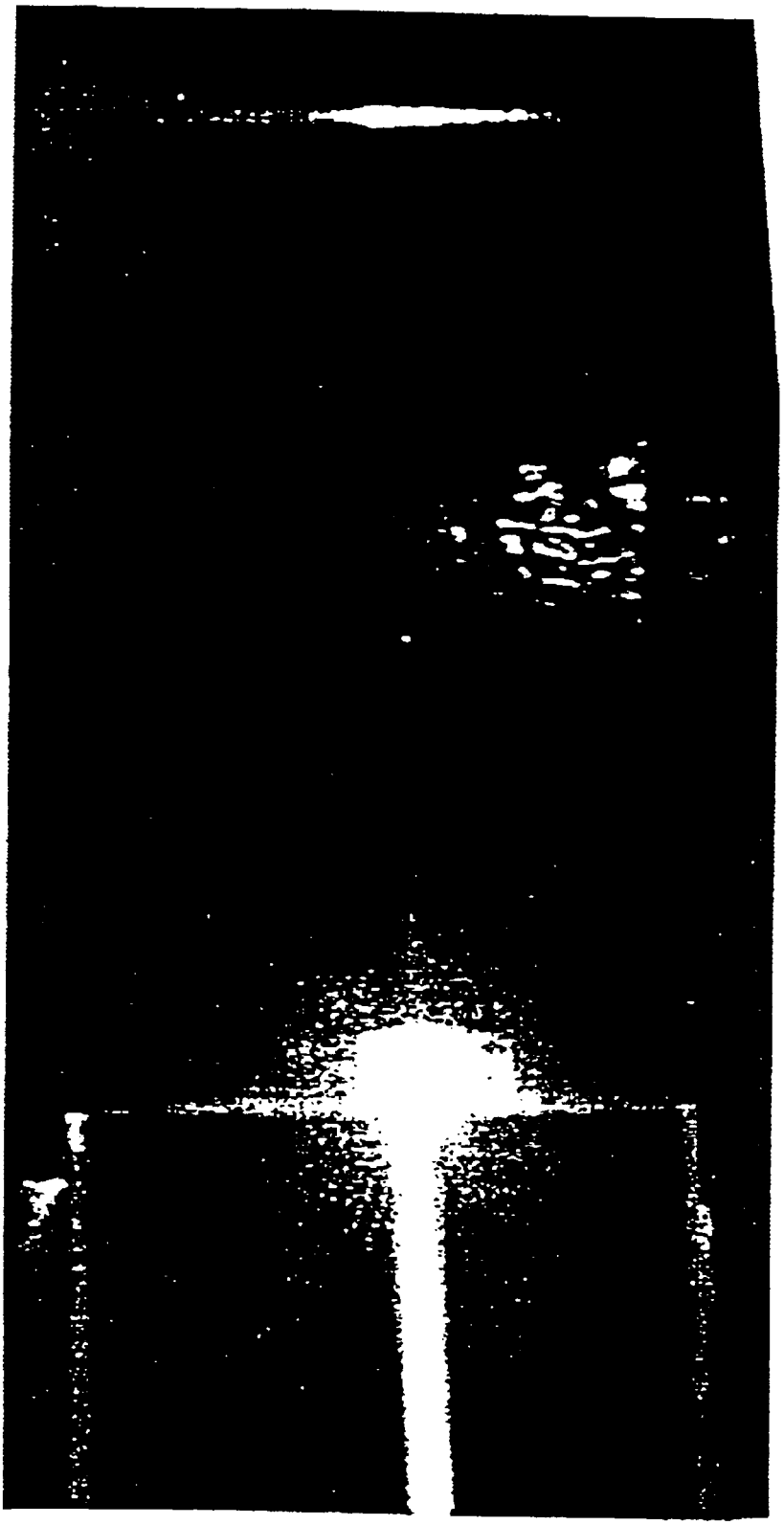
Figure 31:
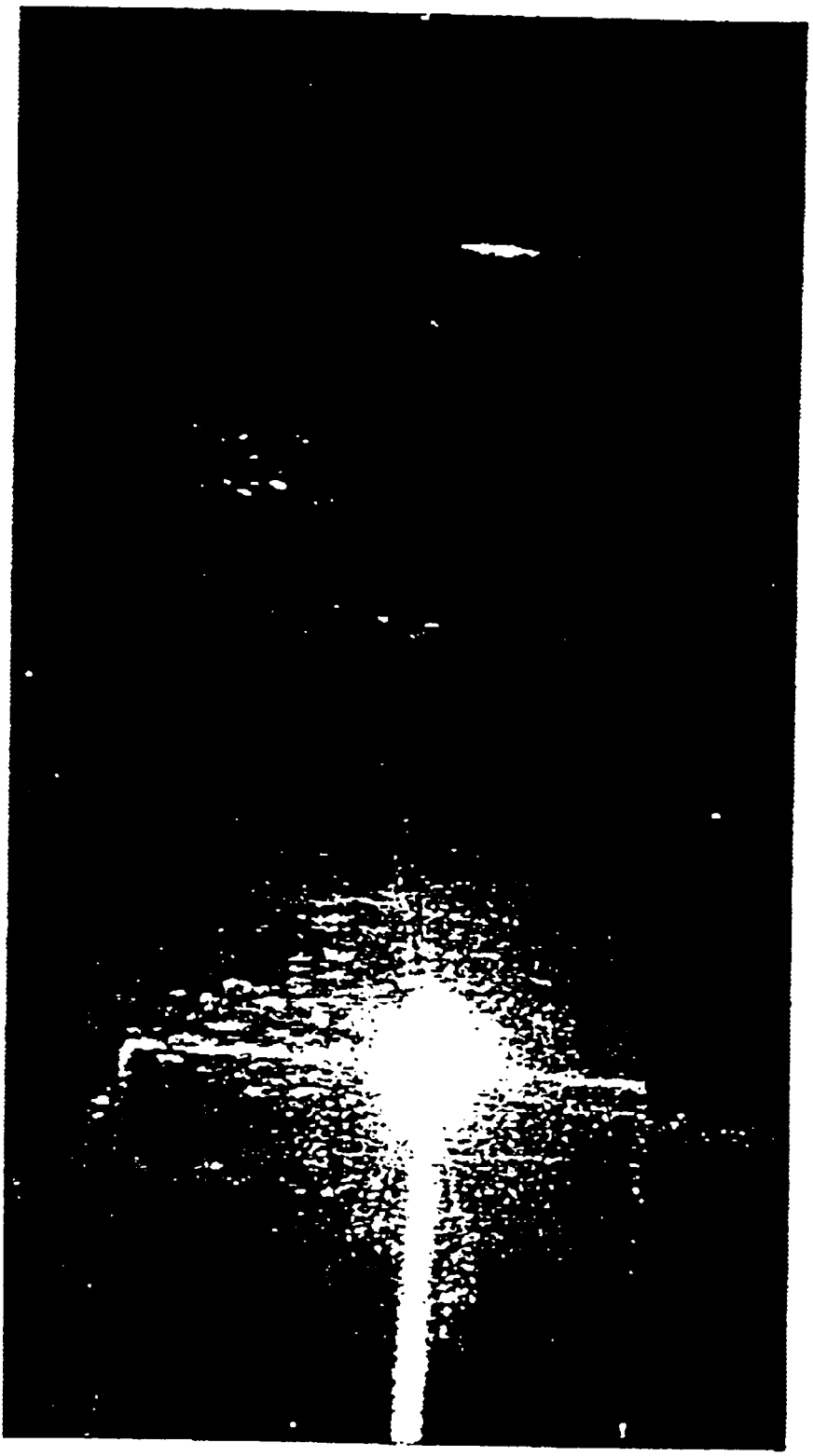

The light path is revealed due to micro-scattering in the waveguide. It is clear that TM polarised red light is strongly transmitted as a single beam (FIG. 28), but TE polarised red light is completely blocked by the device (FIG. 29). FIGS. 30 and 31 are the corresponding photographs for green light. TE polarised light is either scattered vertically out of the wave-guide, or reflected back along the incident beam path. There is no visible increase in up-scattering. Replacing the He—Ne laser source with a tuneable dye laser, demonstrates the lower band edge to be 620 nm. Strong single beam transmission was maintained over the remainder of the tuneable range down to 575 nm, proving that scattering is not responsible for the effect.

Figure 32:
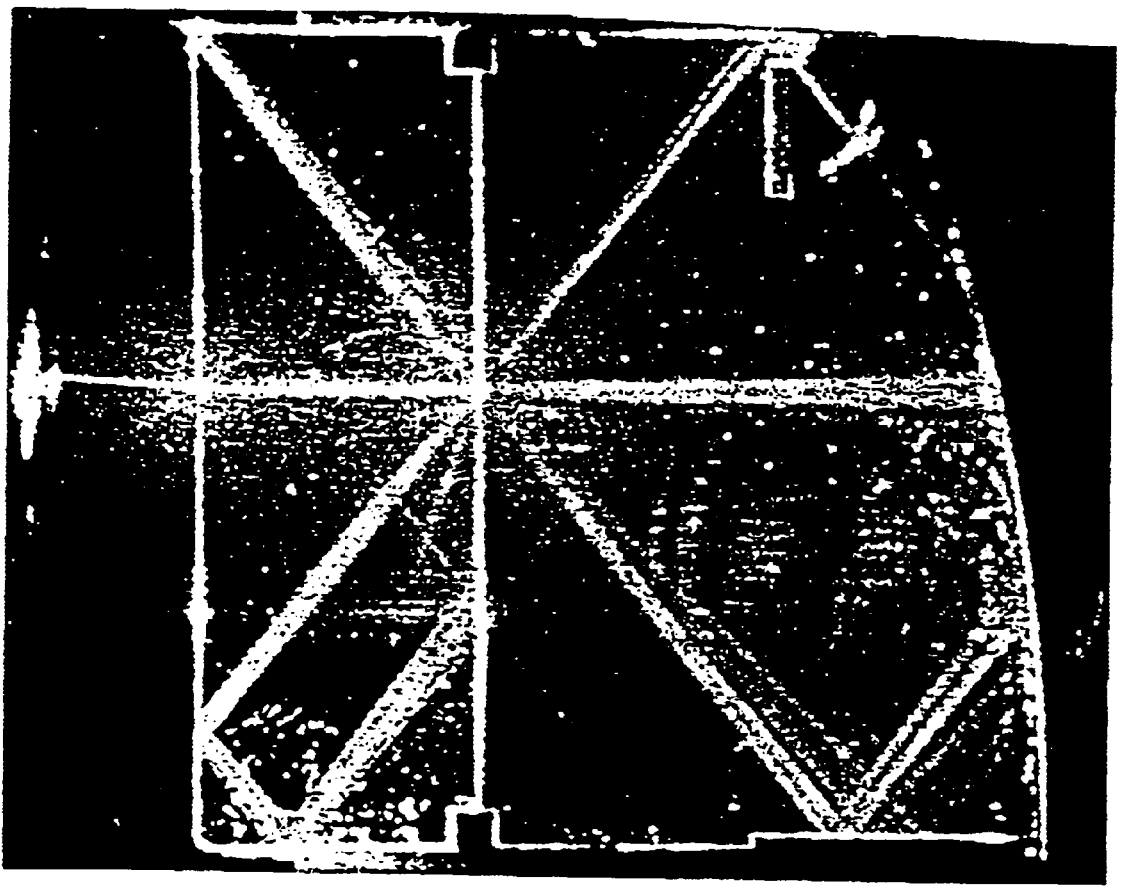

Although strong single beam transmission across many thousands of lattice periods is observed in FIGS. 28–31, unusual beam splitting effects come into play if the number of periods is significantly reduced. A device consisting of 60 rows of air holes (radius 150 nm), arranged on a 260 nm pitch triangular lattice, with an air filling fraction of 26% demonstrates this most clearly. FIG. 32 shows light passing through this device directly from above. The curved edge of the wafer is seen to the right, and the PBG strip goes from top to bottom of the photo bounded by two square marker blocks. A laser is focussed onto the cleaved waveguide facet by a microscope objective, which launches light along the T-J symmetry direction. (FIGS. 33, 34).

Photograph FIG. 32 shows the behaviour of TE polarised red light at 632.8 nm (above the upper band edge), as it traverses the PBG structure. The input beam is split into six beams upon incidence to the device. Three beams are transmitted across the device, two beams are reflected backwards at 410 (measured with respect to the PBG strip), and the third is reflected back along the input beam path. Observation of the trajectory of the back-reflected beams shows that one is reflected from the wafer edges back onto the device where it is again split into six beams. By launching light along the direction of any of the other beam paths exactly the same pattern is obtained. This effect is due to zero order two-dimensional diffraction from lattice symmetry planes.

Yellow light at 594 nm is completely blocked by the device, and there are two sets of back-reflected beams. Behaviour is even more unusual well below the lower band edge for green light at 545 nm (photo FIG. 35). Although there are two sets of back-reflected beams, there is only a single transmitted beam. Using a tunable dye laser, the upper band edge was determined to be 607 nm. The band gap extended over the remaining tunable range down to 575 nm, establishing a lower band edge in the range 545–575 nm. TM polarised light gave single beam transmission over the entire tuning range. Reducing the number of lattice periods to 30, increases the intensity of the back reflected beams, but the transmitted beams are severely attenuated. On reducing the number of periods below 20, the band gap almost disappears, although beam splitting is still observed.

A device similar to that shown in FIG. 28 demonstrates broadband polarisation selection. The device is set at an angle, and the input beam is incident close to the end of the PBG strip, right on the edge of the wafer. TM polarised green light is clearly refracted out of the wafer by the PBG (FIG. 36), whereas TE polarised green light is reflected back by the PBG (FIG. 37), It is then reflected from the cleaved wafer edge almost back along the input beam path. This is a broadband effect working across the visible spectrum beyond 632.8 nm. This demonstrates a new passive application for PBGs as an integrated-optic polarisation selective element.

A PBG device based on a triangular lattice can with careful design give efficient single beam transmission at wavelengths away from the band gap. A narrow pass-band device may also be created by introducing defects into the regular lattice. This has the effect of creating a very narrow defect mode within the band gap wavelength range. An array of such PBG devices each with a slightly differently tuned defect mode could form the basis of a monolithically integrated demultiplexer for WDM communications.

By reducing the number of lattice periods, a PBG device which splits the input beam into several output beams over a large wavelength range can be designed. Since this effect is attributed to two-dimensional zero-order diffraction, the number of output beams is dependent upon the number of lattice symmetry planes. By cascading several structures, a new type of bi-directional multiplexer may be constructed.

Furthermore, by incorporating defect modes into the device, a narrow band wavelength selective cross-connect port may be made. Polarisation dependence of the band gap may be employed to create a PBG device which acts as an integrated optical polarisation selector.

FIG. 37 illustrates the principle of the introduction of defects into lattice structures to produce a desired frequency characteristics. FIG. 37a shows a PBG lattice with an array of holes 130 in a triangular packing arrangement. In FIG. 37b, certain of these holes are missing leaving gaps 131 in the lattice, whilst in FIG. 37c these holes of larger size 132 are substituted for these gaps.

FIG. 38 shows an array where the spacing of rows of holes is progressively increased. The spacing d increases linearly from row to row. Such an arrangement may be incorporated in a wavelength division multiplexer (FIG. 39). This is illustrated schematically in the form of an integrated optical chip with radiation from an input radiation guide 135 being separated by WDMs 134 and passed to separate output guides 136. FIG. 40a–c shows another embodiment in which these components are incorporated in a network arrangement.

The construction of two frequency-dependent optical components is shown schematically in FIGS. 41a and 41b. FIG. 41a illustrates a 90° bend in which gaps 131 in a lattice 130 guide light around the bend, whilst FIG. 41b shows a Y-splitter.

FIGS. 42a to d shows the frequency characteristics of filters with different PBG structures. The arrangements of FIGS. 42a and 42b have a broad stop band 140 arranged above and below a characteristic frequency $f_0$ respectively to give a low-pass and high-pass filter. A staggered gap arrangement gives a narrow stop band 141 whilst a defect mode 142 gives a narrow pass band. The upper and lower band edges are shown at 143 and 144.

Photons lying near the edge of the band gap in energy will be considerably reduced in velocity through the PBG structure (within the band gap itself they stop, they are standing waves). By fabricating a PBG region which is close to the transmitted (information carrying) photon energy, the photon stream may be slowed down. This permits signal processing of the data to occur in more reasonable time scales (in exactly the same way that delay lines are used in electrical signal processing).

The polarisation dependence of the 'in-plane' photonic band gap may be extended to three dimensions. Although TE and TM polarisation states are mixed as far as the calculations are concerned, each dispersion curve in a 'three dimensional' band diagram can be firmly associated with a particular polarisation state. Extending this principal further, the three-dimensional polarisation dependence of the band gap, permits a useful TE polarised band gap to be created in a low refractive index material.

When coupling optical waveguides there will be an element of loss due to back reflection at the interface between media of different refractive index. The level of back reflection is proportional to the contrast in refractive indices between the two media. Since an important attribute of a photonic band gap structure is a high refractive index, there may be a significant back reflection of a wave incident at the input face. The actual level of back reflection will be dependent on the effective mode index of the guided Bloch mode in the PBG structure. One method of overcoming this problem is to grade the effective mode index near the boundary between the waveguide and the photonic band gap structure by introducing a set of holes, the diameter of which is significantly less than the wavelength of the propagating Bloch modes within the PBG structure. This creates a region which presents a reduced refractive index to the propagating waves.

Figure 44B:
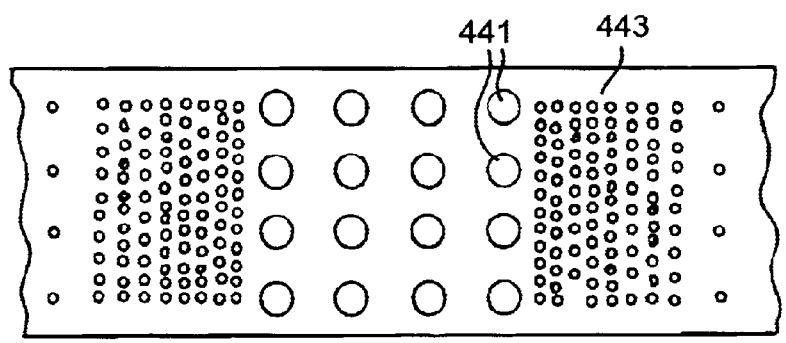

In FIG. 43 an input wave I enters a waveguide W and is partially reflected by a region R of different refractive index. The remainder of the radiation T is transmitted. FIG. 44a illustrates one embodiment in which a main photonic band gap region PBG comprises uniformly space pores 441 of uniform size. At the boundary of this region pores 442 of progressively smaller size occupy lattice positions corresponding to those of the main band gap structure. In an alternative embodiment (FIG. 44b) these index matching pores 443 are of much smaller, but uniform size and their packing density decreases as the distance from the band gap region increases.

In order to compensate for edge effects and to provide other optical transmission characteristics it is sometimes desirable to provide holes of different size at different locations in the PBG lattice.

FIG. 45 is an SEM showing a PBG isolated waveguide section where the pore radius has been corrected at the guide edges to give a uniform pore radius across the whole lattice. The bright uniform rectangular features at the top of the SEM are mesa-isolated waveguide sections which direct light into the PBG device.

FIG. 46 is an example of a PBG lattice where the diameter of the pores in the 1st two rows of lattice has been increased slightly. (Diameter of first row clearly larger than rest of the lattice. The SEM is grainy due to the very high resolution required to see pore features.

FIG. 47 is a clearer example of pore grading in the first two rows of PBG lattice (closest to the waveguide edge). This SEM also clearly shows a waveguide bend.

FIG. 48 is a schematic view of an optical bus for use in an electronic device. A silicon nitride waveguide WG is defined by means of a photonic band gap on the surface of a silicon substrate SC of a semiconductor integrated circuit. An electro-optical transducer $T_{EO}$, which may for example be a region of erbium-doped silica converts electrical signals to optical signals, which then propagate through the waveguide to an opto-electronic transducer $T_{OE}$ which may, for example, be a PBG with a 90° bend in association with an avalanche diode.

An optical bus, for use in association with a microprocessor or a communications system, for example, comprises a plurality of optical waveguides $Z_1$–$Z_{10}$ each coupled to individual electro-optical or opto-electronic transducers Rx,Tx The transducers are provided with electrical contacts C. Each pair of transducers has different frequency bandpass characteristics to serves as components in a WDM system.

Although the described embodiments operate in the visible region of the spectrum, our nano-fabrication processes and material system are suitable for use in the infra red, covering all the major optical communications windows. It is a relatively simple matter for one skilled in the art to scale up the dimensions to operate at these wavelengths.

Optical filters may be fabricated by employing an a periodic hole lattice. The frequency-selective filter characteristics of waveguides produced by the methods herein described have made possible the development of single mode LEDs and high efficiency, narrow line width lasers. Passive filters make possible optical components including a single frequency laser, a single-frequency optical clock and a WDM beam splitter.

Certain lattice structures, such as the triangular lattice or the graphite lattice, are the only ones which are operative for both polarisation states. A square lattice structure may therefore be used to produce a polarisation dependent filter. The lattice structure may be tailored to fabricate a comb laser or a comb filter to give uniform WDM channel response. An optical delay line may be constructed using the lattice shape to control the PBG structure. This may utilise a combination of hole shapes to create a quasi-periodic structure or combination of two lattices

What is claimed is:

1. An active optical device having a waveguide comprising a region of optically—transmissive material bounded by a photonic band gap and containing a dopant adapted to induce a non-linear optical characteristic in said material.

2. An active optical device having a waveguide comprising a region of optically—transmissive material bounded by a photonic band gap and containing a dopant adapted to induce quasi-stable energy levels in said material.

3. A hybrid opto-electronic signal translation device having a first region adapted to transfer a signal by means of movement of electrical charge carriers and a second region adapted to transfer a corresponding signal by means of electromagnetic radiation and electro-optic transducer means disposed between said first and second regions to convert said signal from or to said corresponding signal wherein said second region includes a third region at least partially bounded by a photonic band gap.

4. A coupler to a waveguide at least partially defined by a photonic band gap having an input or output port for the transfer of radiation to or from said waveguide wherein said input or output port includes a region having a graded refractive index to enhance the transfer of radiation to or from said waveguide.

5. An optical device comprising a lasing cavity which includes a material possessing energy levels capable of stimulated emission at a plurality of wavelengths, wherein at least a portion of the material within the lasing cavity is patterned to form a 2-dimensional array that gives rise to a photonic band gap structure which has the effect of selecting a predetermined one or ones of said wavelengths.

6. An optical device supporting an optical path, including:
   an optical input;
   an optical output; and
   an optical filter comprising a planar waveguide structure having a 2-dimensional patterned array that gives rise to a photonic band structure, the optical filter being positioned within the optical path such that light travelling from the optical input to the optical output propagates through the patterned array, the response of the filter being dependent on the configuration of the patterned planar waveguide structure.

7. An optical device including a photonic band gap region having a quasiperiodic lattice structure.

8. A sensor comprising an optical device including a region having a photonic band gap adapted to be exposed to substance to be tested wherein the optical characteristics of said photonic band gap are different according to whether or not said region is exposed to said substance.

9. An optical device according to claim 6, wherein the patterned planar waveguide structure comprises a first region formed from a first material having a first refractive index, and an array of sub-regions within the first region, each of the sub-regions having a refractive index different to the first refractive index.

10. An optical device according to claim 9, wherein defects are present in the sub-array of regions, the defects resulting in a narrow pass band within a bandgap wavelength range.

11. An optical device according to claim 11, wherein the defects are irregularities in the size of the sub-regions within the first material.

12. An optical device according to claim 11, wherein the defects are irregularities in the spacing of the array of sub-regions within the first material.

13. An optical device according to claim 10, wherein the spacing of the sub-regions in the array increases across at least a portion of the array.

14. An optical device according to claim 9, wherein the size of the sub-regions is graded across at least a portion of the array.

15. An optical device according to claim 6, wherein the patterned planar waveguide structure contains a dopant adapted to induce a non-linear characteristic in the filter.

16. An optical device according to claim 6, wherein the patterned planar waveguide structure contains a dopant adapted to induce quasi-stable energy levels within a bandgap.

17. An optical device according to claim 9, wherein the first material is silicon nitride.

18. An optical device according to claim 9, wherein the first material is a fluorescent material.

19. An optical device according to claim 18, wherein the fluorescent material is a lasing glass, and a photonic bandgap formed as a result of the array of sub-regions prevents the fluorescence of predetermined transition wavelengths of the lasing glass.

20. An optical device according to claim 9, wherein the array of sub-regions is exposed to an environment and the refractive index of the sub-regions, and hence the response of the filter, is altered in response to changes in the environment.

21. An optical device according to claim 6, comprising a quasi-periodic array of sub regions.

22. An optical device according to claim 6, further comprising a region having a photonic band structure which exhibits diffractive properties.

23. An optical demultiplexer including an array of device according to claim 6, wherein each of the array of devices has a different pass band.

24. An optical device according to claim 6, wherein the device includes a cladding layer and a core layer, and the 2-dimensional patterned array extends through the cladding layer and through the core layer.

25. An optical device according to claim 9, wherein the array of sub-regions is an array of holes.

26. An optical device according to claim 6, wherein light propagating through the patterned array is slowed to a group velocity which is dependent upon its wavelength.

* * * * *